United States Patent
Wada et al.

(10) Patent No.: US 9,507,284 B2
(45) Date of Patent: Nov. 29, 2016

(54) ELECTROPHOTOGRAPHIC PHOTORECEPTOR, ELECTROPHOTOGRAPHIC PHOTORECEPTOR CARTRIDGE, IMAGE-FORMING APPARATUS, AND TRIARYLAMINE COMPOUND

(71) Applicant: MITSUBISHI CHEMICAL CORPORATION, Chiyoda-ku (JP)

(72) Inventors: Mitsuo Wada, Kanagawa (JP); Hiroe Fuchigami, Kanagawa (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 14/609,543

(22) Filed: Jan. 30, 2015

(65) Prior Publication Data

US 2015/0205217 A1    Jul. 23, 2015

Related U.S. Application Data

(63) Continuation of application No. PCT/JP2013/070648, filed on Jul. 30, 2013.

(30) Foreign Application Priority Data

Jul. 31, 2012 (JP) .................. 2012-170115
Sep. 27, 2012 (JP) .................. 2012-215002

(51) Int. Cl.

| G03G 5/043 | (2006.01) |
|---|---|
| G03G 5/06 | (2006.01) |
| C07C 217/92 | (2006.01) |
| C07C 217/94 | (2006.01) |
| G03G 5/05 | (2006.01) |
| G03G 5/147 | (2006.01) |
| C07C 211/54 | (2006.01) |

(52) U.S. Cl.
CPC .......... *G03G 5/0618* (2013.01); *C07C 211/54* (2013.01); *C07C 217/92* (2013.01); *C07C 217/94* (2013.01); *G03G 5/0564* (2013.01); *G03G 5/0614* (2013.01); *G03G 5/0666* (2013.01); *G03G 5/14708* (2013.01); *G03G 5/14756* (2013.01)

(58) Field of Classification Search
CPC .................. G03G 5/04; G03G 5/043
See application file for complete search history.

(56) References Cited

U.S. PATENT DOCUMENTS

| 5,298,353 | A | * | 3/1994 | Ohmori ............. C09B 67/0016 399/159 |
|---|---|---|---|---|
| 5,686,212 | A | | 11/1997 | Tomiuchi et al. |
| 5,733,697 | A | | 3/1998 | Endoh et al. |
| 5,831,084 | A | * | 11/1998 | Toguchi ............. C09B 67/0014 430/78 |
| 6,022,997 | A | | 2/2000 | Endoh et al. |
| 6,258,499 | B1 | | 7/2001 | Itami |
| 2008/0063963 | A1 | | 3/2008 | Tajima et al. |
| 2009/0047589 | A1 | | 2/2009 | Tajima et al. |
| 2011/0013934 | A1 | | 1/2011 | Tajima et al. |

FOREIGN PATENT DOCUMENTS

| JP | 6-118674 | 4/1994 |
|---|---|---|
| JP | 7-036203 | 2/1995 |
| JP | 9-304952 | 11/1997 |
| JP | 2940502 | 6/1999 |
| JP | 2000-162791 | 6/2000 |
| JP | 2002-080432 | 3/2002 |
| JP | 2006-008670 | 1/2006 |
| JP | 2006-53549 | 2/2006 |
| JP | 2006-139268 | 6/2006 |
| JP | 2008-70591 | 3/2008 |
| JP | 2009-93024 | 4/2009 |

OTHER PUBLICATIONS

Extended Search Report issued Jun. 19, 2015 in European Patent Application No. 13826271.2.
International Search Report issued in PCT/JP2013/070648, dated Oct. 1, 2013.
U.S. Appl. No. 14/609,543, filed Jan. 30, 2015, Wada et al.
U.S. Appl. No. 14/608,839, filed Jan. 29, 2015, Fujii et al.

* cited by examiner

*Primary Examiner* — Hoa V Le
(74) *Attorney, Agent, or Firm* — Oblon, McClelland, Maier & Neustadt, L.L.P.

(57) ABSTRACT

The present invention relates to an electrophotographic photoreceptor comprising an electroconductive support and at least a photosensitive layer formed on the support, wherein the photosensitive layer contains a specific charge transport substance.

9 Claims, 5 Drawing Sheets

ELECTROPHOTOGRAPHIC PHOTORECEPTOR, ELECTROPHOTOGRAPHIC PHOTORECEPTOR CARTRIDGE, IMAGE-FORMING APPARATUS, AND TRIARYLAMINE COMPOUND

TECHNICAL FIELD

The present invention relates to an electrophotographic photoreceptor having excellent electrical properties and mechanical properties, an electrophotographic photoreceptor cartridge produced using the electrophotographic photoreceptor, and an image-forming apparatus. Furthermore, the invention relates to a triarylamine compound useful as the electrophotographic photoreceptor.

BACKGROUND ART

Electrophotographic technology has been widely used for copiers, printers, printing machines and the like since high-quality images are instantaneously obtained. As electrophotographic photoreceptors (hereinafter optionally referred to as "photoreceptor") which lie in the core technology of the electrophotographic technology, there have been widely used photoreceptors using organic photoconductive materials having advantages such as non-pollution, ease in film formation and ease in manufacture.

Recently, owing to the requirement for high-quality images, a toner size has been miniaturized and particularly, in a chemical toner, since the shape frequently takes a form close to a sphere, toner-passing-through is prone to occur at the time when a toner remaining on the photoreceptor is cleaned by means of a blade and, as a result, there is a high possibility of causing image defects such as scumming. Therefore, there is frequently taken a countermeasure that the cleaning blade is abutted to the photoreceptor with a strong pressure to prevent the toner from passing through.

When the abutting pressure of the cleaning blade to the photoreceptor increases, the bade causes chattering owing to repeated sticking/slipping on the uppermost surface of the photoreceptor, a so-called stick/slip phenomenon and, as a result, there increases a risk of occurrence of insufficient cleaning and abnormal noise. Moreover, by rotation in a state where an external additive and a toner carrier that are toner components are strongly pressed against the photoreceptor through a nip part by the cleaning blade, a decrease in the life of the photoreceptor life due to increased wear of the photosensitive layer and image defects due to the occurrence of the circumferential scratches are prone to occur. Furthermore, a so-called filming phenomenon that the external additive and wax as toner components are fixed to the surface of the photoreceptor and the removal becomes difficult tends to occur, so that a risk of generation of sustained image defects also increases.

As such, it is desired for the photoreceptor to have surface mechanical properties so as to minimize the image defects, abnormal noise, and the decrease in the life attributable to the filming even under more severe use conditions. As a method for improving the surface mechanical properties, such as filming, a method of improving the surface mechanical properties by providing a protective layer on the uppermost surface layer of the photoreceptor has been investigated. However, the productivity is lowered and the cost increases, so that it is difficult to apply the method in many cases other than high-end machine applications.

On the other hand, the photoreceptor is reduced in diameter on the trend of miniaturization and increase in speed of an electrophotographic device, and more improved electrical response (quick decrease in the surface potential of the photoreceptor after exposure) has been demanded. In order to provide an electrophotographic photoreceptor satisfying the characteristics, it is necessary to develop a highly functional charge transport substance showing high mobility and sufficiently low residual potential at the time of exposure. In order to solve the problems, many studies of charge transport substances in which n-electron system is extended by a styryl group or the like with a triphenylamine skeleton or a tetraphenyl benzidine skeleton (Patent Documents 1 to 6).

Incidentally, a photosensitive layer of the electrophotographic photoreceptor using an organic material is obtained by dissolving a charge transport substance, a binder resin and the like in a coating solvent and applying and drying the resulting coating fluid. The points required for the charge transport substance in manufacturing the electrophotographic photoreceptor are solubility in the coating solvent used at the manufacture of the coating fluid and compatibility with the binder resin. When the solubility and compatibility are low, it may not be able to dissolve a desired amount of the charge transport substance in the coating solvent, and degradation of the coating fluid, such as deposition, is prone to occur after the charge transport substance is dissolved to manufacture the coating fluid. Furthermore, crystals may be precipitated in the coated film after the photosensitive layer is coated, thereby inviting reduction of the manufacturing efficiency of the coating fluid and the photoreceptor.

In general, a compound having an extended $\pi$-electron system in the molecule shows increased intermolecular interactions as the molecular size increases and the solubility tends to decrease. The tetraphenylbenzidine skeleton described above has a large molecular size and tends to show low solubility and, when a styryl group or the like is substituted in the tetraphenylbenzidine skeleton to extend the $\pi$-electron system in the molecule, the molecular size further increases and the solubility in the coating solvent becomes even lower. In some of the reports previously mentioned, in order to ensure the solubility, there has been made a contrivance of handling as a geometric isomer mixture (Patent Document 6).

PRIOR ART DOCUMENTS

Patent Documents

Patent Document 1: JP-A-7-36203
Patent Document 2: JP-A-2006-8670
Patent Document 3: JP-A-6-118674
Patent Document 4: Japanese Patent No. 2940502
Patent Document 5: JP-A-2008-70591
Patent Document 6: JP-A-2002-80432

SUMMARY OF THE INVENTION

Problems that the Invention is to Solve

As described above, even when known charge transport materials having fast charge mobility, many of them show excellent response but decrease in the residual potential is insufficient. Therefore, it is necessary to use a relatively large amount of the binder resin and, as a result, it is inferior in terms of abrasion resistance in many cases.

On the other hand, according to the study of the inventors, in the backbone of the charge transport material such as one described in Patent Document 4, the residual potential is low enough but, in a high-speed process, the skeleton does not have sufficient characteristics such as durability to filming and wear. Furthermore, it is inferior in image memory properties and storage stability and, in a high-speed process, there are cases where it cannot be used since fine defects resulting from crystallization and scratches significantly influence even when the residual potential and the response are satisfactory.

The present invention has been made in view of the above background art, and an object thereof is to provide a triarylamine compound showing rapid response and low enough potential at the exposed part and having good transfer memory and excellent storage stability. Moreover, another object thereof is to provide an electrophotographic photoreceptor, an image-forming apparatus and an electrophotographic cartridge hardly causing filming and insufficient cleaning, having excellent abrasion resistance and showing high electrical properties, in view of mechanical physical properties even in a high-speed process.

Means for Solving the Problems

As a result of intensive studies, the present inventors have found a triarylamine compound showing rapid response and low enough potential at the exposed part and having good transfer memory and excellent storage stability. Also, they have found that it is possible to provide an electrophotographic photoreceptor hardly causing filming or image defects owing to wear at the time of long-term printing and capable of exhibiting excellent performance in view of the mechanical properties while exhibiting sufficiently low residual potential at the time of exposure, by incorporating the triarylamine compound having the specific structure into the photosensitive layer of the electrophotographic photoreceptor, and thus they have completed the present invention.

The gist of the invention lies in the following <1> to <9>.
<1> An electrophotographic photoreceptor comprising an electroconductive support and at least a photosensitive layer formed on the support, wherein the photosensitive layer contains a charge transport substance represented by the following formula (1):

[Chem 1]

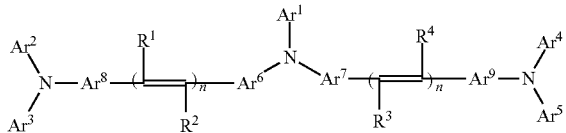

wherein $Ar^1$ represents an aryl group having an alkoxy group, an aryloxy group, or an aralkyloxy group as a substituent, $Ar^2$ to $Ar^5$ each independently represent an aryl group which may have a substituent, $Ar^6$ to $Ar^9$ each independently represent a 1,4-phenylene group which may have a substituent; $R^1$ to $R^4$ each independently represent a hydrogen atom or an alkyl group; m and n each independently represent an integer of 1 or more and 3 or less; in the case where m or n is 2 or more, plurally existing $R^1$s to $R^4$s each may be the same or different from each other.

<2> The electrophotographic photoreceptor according to the <1> above, wherein the photosensitive layer contains oxytitanium phthalocyanine of crystal form which shows a diffraction peak at Bragg angles (2θ±0.2°) of at least 24.1° and 27.2° in a powder X-ray diffraction spectrum with a CuKα characteristic X-ray.

<3> The electrophotographic photoreceptor according to the <1> or <2> above, wherein the photosensitive layer further contains at least either one of a polyarylate resin and a polycarbonate resin.

<4> The electrophotographic photoreceptor according to any one of the <1> to <3> above, wherein the photosensitive layer comprises a charge transport layer and a charge generation layer and the charge transport layer contains a charge transport substance represented by the above formula (1) and at least either one of a polyarylate resin having a structural unit represented by the formula (α) and a polycarbonate resin having a structural unit represented by the formula (β):

[Chem 2]

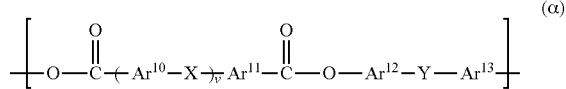

wherein $Ar^{10}$ to $Ar^{13}$ each independently represent an arylene group which may have a substituent, X represents a single bond, an oxygen atom, a sulfur atom, or an alkylene group; v represents an integer of 0 or more and 2 or less; and Y represents a single bond, an oxygen atom, a sulfur atom, or an alkylene group,

[Chem 3]

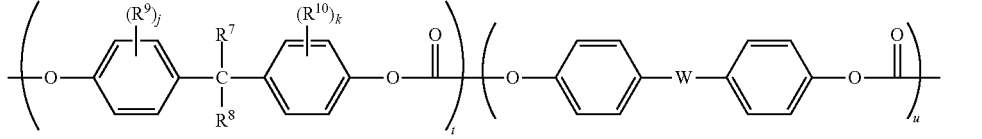

wherein $R^7$ and $R^8$ each independently represent a hydrogen atom, an aryl group, or an alkyl group having 1 to 10 carbon atoms and the $R^7$ and $R^8$ groups may be combined to form a ring; $R^9$ and $R^{10}$ each independently represent a hydrogen atom or an alkyl group having 1 to 10 carbon atoms and j and k each independently represent an integer of 0 to 4; W represents a single bond, an oxygen atom, or $-CR^{11}R^{12}-$ and the $R^{11}$ and $R^{12}$ groups each independently represent a hydrogen atom, an alkyl group having 1 to 10 carbon atoms, or a phenyl group; t and u each independently represent a numeral of 0 to 100; provided that the units represented by t and u have different structures and there is no case of t=u=0.

<5> An electrophotographic photoreceptor cartridge comprising: the electrophotographic photoreceptor according to any one of the <1> to <4> above; and at least one device selected from the group consisting of a charging device which charges the electrophotographic photoreceptor, an exposure device which exposes the charged electrophotographic photoreceptor to form an electrostatic latent image, and a developing device which develops the electrostatic latent image formed on the electrophotographic photoreceptor.

<6> An image-forming apparatus comprising: the electrophotographic photoreceptor according to any one of the <1> to <4> above; a charging device which charges the electrophotographic photoreceptor; an exposure device which exposes the charged electrophotographic photoreceptor to form an electrostatic latent image; and a developing device which develops the electrostatic latent image formed on the electrophotographic photoreceptor.

<7> A compound represented by the formula (1):

[Chem 4]

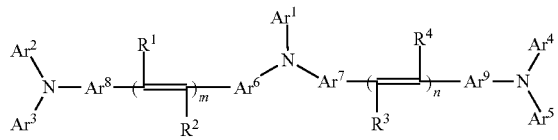

wherein $Ar^1$ represents an aryl group having an alkoxy group, an aryloxy group, or an aralkyloxy group as a substituent, $Ar^2$ to $Ar^5$ each independently represent an aryl group which may have a substituent, $Ar^6$ to $Ar^9$ each independently represent a 1,4-phenylene group which may have a substituent; $R^1$ to $R^4$ each independently represent a hydrogen atom or an alkyl group; m and n each independently represent an integer of 1 or more and 3 or less; in the case where m or n is 2 or more, plurally existing $R^1$s to $R^4$s each may be the same or different from each other.

<8> The compound according to the <7> above, wherein, in the above formula (1), $Ar^1$ is a phenyl group having an alkoxy group having 8 or less carbon atoms, $Ar^2$ to $Ar^5$ each independently are a phenyl group which may have an alkyl group having 1 to 6 carbon atoms or an alkoxy group having 1 to 6 carbon atoms as a substituent, $Ar^6$ to $Ar^9$ each independently are a 1,4-phenylene group which may have an alkyl group having 1 to 6 carbon atoms, $R^1$ to $R^4$ are a hydrogen atom, and m and n are both 1.

<9> The compound according to the <8> above, wherein, in the above formula (1), $Ar^2$ to $Ar^5$ each independently are a phenyl group which may have an alkyl group having 1 to 6 carbon atoms and $Ar^6$ to $Ar^9$ are a 1,4-phenylene group.

Advantage of the Invention

The present invention makes it possible to provide a triarylamine compound having excellent storage stability and showing high electrical properties as a charge transport substance of an electrophotographic photoreceptor. In addition, the invention makes it possible to provide an electrophotographic photoreceptor, an electrophotographic cartridge, and an image-forming apparatus hardly causing filming, insufficient cleaning and the like, having excellent abrasion resistance, showing rapid response and low enough potential at the exposed part in view of electrical properties, and further having excellent transfer memory and good storage stability. In particular, the invention makes it possible to provide an electrophotographic photoreceptor and the like hardly causing filming, insufficient cleaning and the like in the case of using a polyarylate resin as a binder resin and an electrophotographic photoreceptor and the like having excellent abrasion resistance in the case of using a polycarbonate.

MODES FOR CARRYING OUT THE INVENTION

Figure 1:
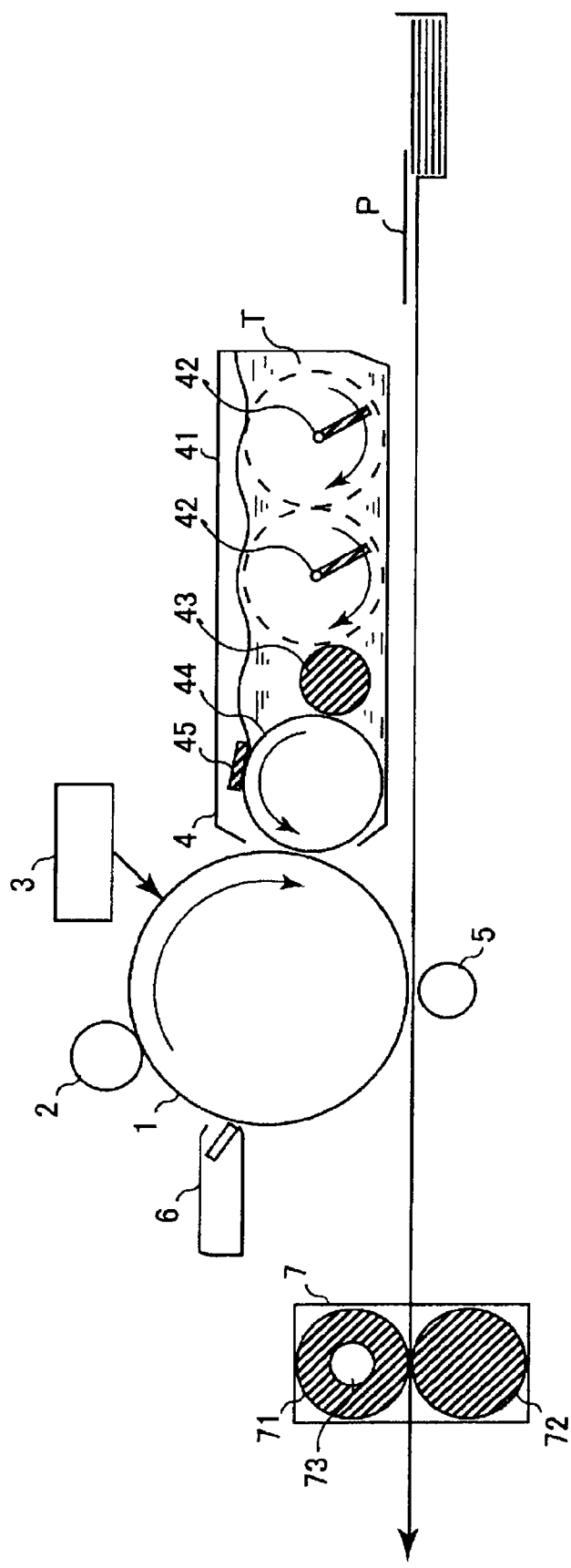
FIG. 1 is a schematic view which illustrates the configuration of important parts of one embodiment of the image-forming apparatus of the invention.

Modes for carrying out the invention are explained below in detail. However, the following explanations on constituent elements are representative examples of embodiments of the invention, and the embodiments can be suitably modified unless the modifications depart from the spirit of the invention.

Here, "% by weight", "parts by weight" and "ratio by weight" have the same meaning as "% by mass", "parts by mass" and "ratio by mass", respectively.

<<Electrophotographic Photoreceptor>>
<Charge Transport Substance>

The invention is an electrophotographic photoreceptor comprising an electroconductive support and at least a photosensitive layer formed on the support, wherein the photosensitive layer contains a charge transport substance represented by the following formula (1):

[Chem 25]

Formula (1)

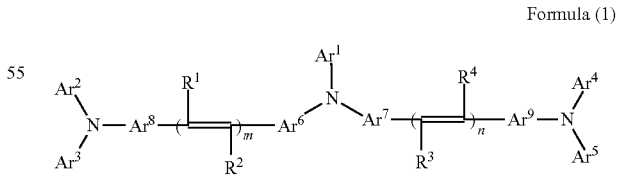

wherein $Ar^1$ represents an aryl group having an alkoxy group, an aryloxy group, or an aralkyloxy group, $Ar^2$ to $Ar^5$ each independently represent an aryl group which may have a substituent, $Ar^6$ to $Ar^9$ each independently represent a 1,4-phenylene group which may have a substituent; $R^1$ to $R^4$ each independently represent a hydrogen atom or an alkyl group; m and n each independently represent an integer of 1 or more and 3 or less; in the case where m or n is 2 or more, plurally existing $R^1$ to $R^4$ may be the same or different from one another.

In the above formula (1), $Ar^1$ represents an aryl group having an alkoxy group, an aryloxy group, or an aralkyloxy group as a substituent.

As the aryl group, there may be mentioned a phenyl group, a naphthyl group, a biphenyl group, an anthryl group, a phenanthryl group, and the like. In view of the charge-transporting capability, a phenyl group and a naphthyl group are preferable and, in terms of the raw material versatility, a phenyl group is more preferable.

As the alkoxy group, there may be mentioned liner alkoxy groups such as a methoxy group, an ethoxy group, an n-propoxy group, and an n-butoxy group; branched alkoxy groups such as an isopropoxy group and an ethylhexyloxy group; cyclic alkoxy groups such as a cyclohexyloxy group; alkoxy groups having a fluorine atom, such as a trifluoromethoxy group, a pentafluoroethoxy group, and a 1,1,1-trifluoroethoxy group.

As the aryloxy group, there may be mentioned an aryloxy group which may have a substituent such as a phenoxy group, a 4-methylphenoxy group, a 1-naphthoxy group, and a 2-naphthoxy group.

As the aralkyloxy group, there may be mentioned a benzyloxy group, a 4-methylbenzyl group, and the like.

Of these substituents, an alkoxy group having 20 or less carbon atoms is preferable in view of the charge-transporting capability, an alkoxy group having 12 or less carbon atoms is more preferable in view of the raw material versatility, and alkoxy group having 8 or less carbon atoms is more preferable in view of the characteristics of the electrophotographic photoreceptor.

$Ar^1$ may have a substituent other than an alkoxy group, an aryloxy group, and an aralkyloxy group. As the substituent which may be present, an alkyl group, an aryl group, a halogen atom, and the like and, specifically, the same substituents as the substituents which $Ar^2$ to $Ar^5$ to be described later may have can be mentioned.

In the case where $Ar^1$ has a substituent which it may have, from the viewpoint of light attenuation characteristics as an electrophotographic photoreceptor, an alkyl group having 1 to 6 carbon atoms is preferable. As the number of the substituents, 1 to 5 are possible, 1 to 3 is preferable from the raw material versatility and, from the viewpoint of the characteristics of the electrophotographic photoreceptor, 1 to 2 is more preferable and 1 is further preferable.

From the viewpoint of compatibility and the electrical properties of the photoreceptor, $Ar^1$ preferably has at least one substituent in the ortho- or para-position to the nitrogen atom and more preferably has a substituent at the para-position.

When $Ar^1$ has a substituent containing an oxygen atom, such as an alkoxy group, an aryloxy group, or an aralkyloxy group, $Ar^1$ becomes an electron donating group and the movement of the charge is facilitated. Moreover, since the polarity is increased, interactions between molecules are moderately reduced and the compatibility with the binder resin and the coating fluid is increased, so that the dispersibility is improved and the crystallization is suppressed. Furthermore, it also contributes to the adhesiveness to the adjacent layers.

In the above formula (1), $Ar^2$ to $Ar^5$ each independently represent an aryl group which may have a substituent. Specifically, as the aryl group, there may be mentioned a phenyl group, a naphthyl group, a biphenyl group, an anthryl group, a phenanthryl group, and the like. In view of the charge-transporting capability, a phenyl group and a naphthyl group are preferable and, in view of the raw material versatility, a phenyl group is more preferable.

As the substituent which $Ar^2$ to $Ar^5$ may have, an alkyl group, an aryl group, an alkoxy group, a halogen atom, and the like may be mentioned.

As the alkyl group, there may be mentioned linear alkyl groups such as a methyl group, an ethyl group, an n-propyl group, and an n-butyl group; branched alkyl groups such as an isopropyl group and an ethylhexyl group; and cyclic alkyl groups such as a cyclohexyl group.

As the aryl group, there may be mentioned a phenyl group, a naphthyl group, a biphenyl group, an anthryl group, a phenanthryl group, and the like.

As the alkoxy group, there may be mentioned linear alkoxy groups such as a methoxy group, an ethoxy group, an n-propoxy group, and an n-butoxy group; branched alkoxy groups such as an isopropoxy group and an ethylhexyloxy group; cyclic alkoxy groups such as a cyclohexyloxy group; and alkoxy groups having a fluorine atom such as a trifluoromethoxy group, a pentafluoroethoxy group, and a 1,1,1-trifluoroethoxy group.

As the halogen atom, there may be mentioned a fluorine atom, a chlorine atom, a bromine atom, and the like.

Of these, an alkyl group having 1 to 20 carbon atoms or an alkoxy group having 1 to 20 carbon atoms is preferable from the raw material versatility, an alkyl group having 1 to 12 carbon atoms or an alkoxy group having 1 to 12 carbon atoms is more preferable in view of handling during manufacture, and an alkyl group having 1 to 6 carbon atoms or an alkoxy group having 1 to 6 carbon atoms is further preferable in view of the light attenuation characteristics as an electrophotographic photoreceptor.

In the case where $Ar^2$ to $Ar^5$ are a phenyl group, they preferably have a substituent in view of charge-transporting capability. As the number of the substituents, from 1 to 5 are possible and, from the raw material versatility, from 1 to 3 is preferable, and from the viewpoint of the characteristics of the electrophotographic photoreceptor, from 1 to 2 is more preferable.

Moreover, in the case where $Ar^2$ to $Ar^5$ are a naphthyl group, from the raw material versatility, the number of the substituents is preferably 2 or less and the number of the substituents is more preferably 1 or less.

From the viewpoint of the compatibility and the electrical properties of the photoreceptor, $Ar^2$ to $Ar^5$ preferably have at least one substituent in the ortho- or para-position to the nitrogen atom and more preferably has a substituent at the para-position.

$Ar^6$ to $Ar^9$ each independently represent a 1,4-phenylene group which may have a substituent. As the substituent which they may have, it is possible to mention substituents similar to the substituents which the above $Ar^2$ to $Ar^5$ may have. Of these, a hydrogen atom or an alkyl group having 1 to 6 carbon atoms is preferable from the raw material versatility, a hydrogen atom or a methyl group is more preferable from the viewpoint of the light attenuation characteristics of the electrophotographic photoreceptor, and a hydrogen atom is still more preferable since there is a possibility that intramolecular π-conjugation extension is interfered and the electron-transporting capability is decreased when twisting occurs in the molecular structure.

In the above formula (1), $R^1$ to $R^4$ each independently represent a hydrogen atom or an alkyl group. Specifically, as the alkyl group, it is possible to mention groups similar to the groups described as the alkyl groups which $Ar^2$ to $Ar^5$ may have. Of these, a hydrogen atom or an alkyl group having 1 to 6 carbon atoms is preferable from the raw material versatility, a hydrogen atom or a methyl group is more preferable from the viewpoint of the light attenuation characteristics of the electrophotographic photoreceptor, and a hydrogen atom is still more preferable since there is a possibility that intramolecular π-conjugation extension is interfered and the electron-transporting capability is decreased when twisting occurs in the molecular structure.

m and n each independently represent an integer of 1 or more and 3 or less. Since there is a tendency that solubility in a coating solvent lowers when m or n becomes larger, they are preferably 2 or less and, in terms of the charge-transporting ability as a charge transport substance, it is more preferably 1.

In the case where at least one of m and n is 1, the case represents an ethenyl group and geometrical isomers are present but, from the viewpoint of the electrophotographic photoreceptor characteristics, a trans-structure is preferable. In the case where at least one of m and n is 2, the case represents a butadienyl group, and geometrical isomers are also present in this case but, from the viewpoint of the coating fluid storage stability, a mixture of two or more geometrical isomers is preferable.

Moreover, the electrophotographic photoreceptor of the invention may contain a compound represented by the formula (1) as a single ingredient in the photosensitive layer or it is possible to contain compounds represented by the formula (1) as a mixture thereof.

Of the compounds represented by the formula (1), a compound is more preferable, wherein $Ar^1$ is a phenyl group having an alkoxy group having 8 or less carbon atoms, $Ar^2$ to $Ar^5$ each independently are a phenyl group which may have an alkyl having 1 to 6 carbon atoms or an alkoxy group having 1 to 6 carbon atoms as a substituent, $Ar^6$ to $Ar^9$ each independently are a 1,4-phenylene group which may have an alkyl having 1 to 6 carbon atoms, $R^1$ to $R^4$ are a hydrogen atom, and m and n are both 1, in terms of the raw material versatility.

Of these, it is preferable that $Ar^2$ to $Ar^5$ each independently are a phenyl group which may have an alkyl having 1 to 6 carbon atoms and $Ar^6$ to $Ar^9$ are a 1,4-phenylene group.

From the viewpoint of the electrical properties of the photoreceptor, a compound represented by the following formula (1a) is particularly preferable. In the formula (1a), $Ar^1$ is a phenyl group having an alkoxy group having 8 or less carbon atoms, $Ar^2$ to $Ar^5$ each independently are a phenyl group which may have an alkyl group having 1 to 6 carbon atoms as a substituent, $Ar^6$ to $Ar^9$ all are an unsubstituted 1,4-phenylene group, $R^1$ to $R^4$ all are a hydrogen atom, and m and n are both 1 in the formula (1).

[Chem 6]

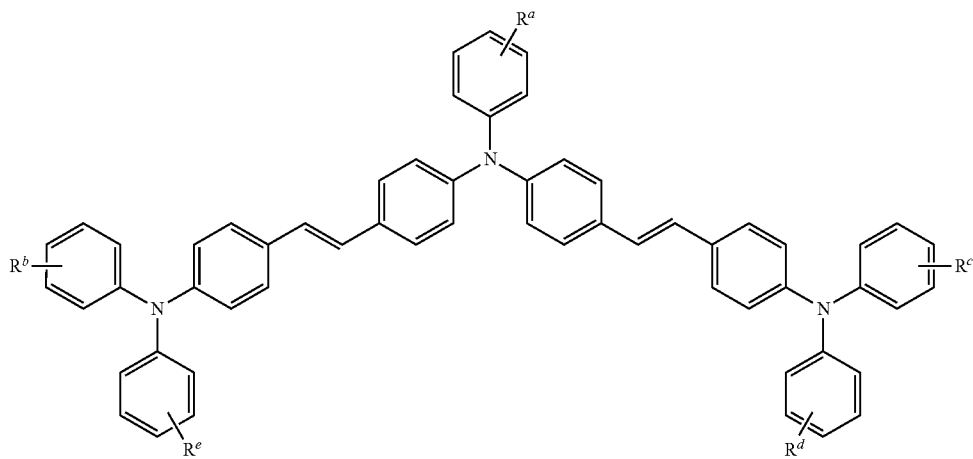

Formula (1a)

wherein Ra represents an alkoxy group having 8 or less carbon atoms and $R^b$ to $R^e$ each independently represent an alkyl having 1 to 6 carbon atoms or a hydrogen atom.

Of the compounds represented by the formula (1), the following will illustrate the structures of suitable compounds as charge transport substances in the electrophotographic photoreceptor of the invention. The following structures are illustrative ones for more specifically describe the invention, and the invention is not limited to the following structures unless they depart from the concept of the invention.

In the formula, Me represents a methyl group, Et represents an ethyl group, tBu represents a tertiary butyl group, nBu represents a normal butyl group.

[Chem 7]
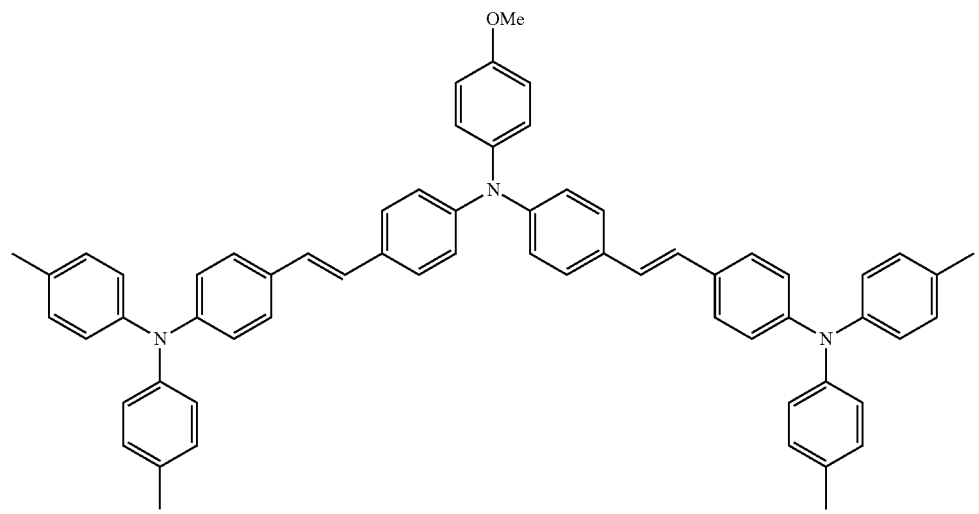
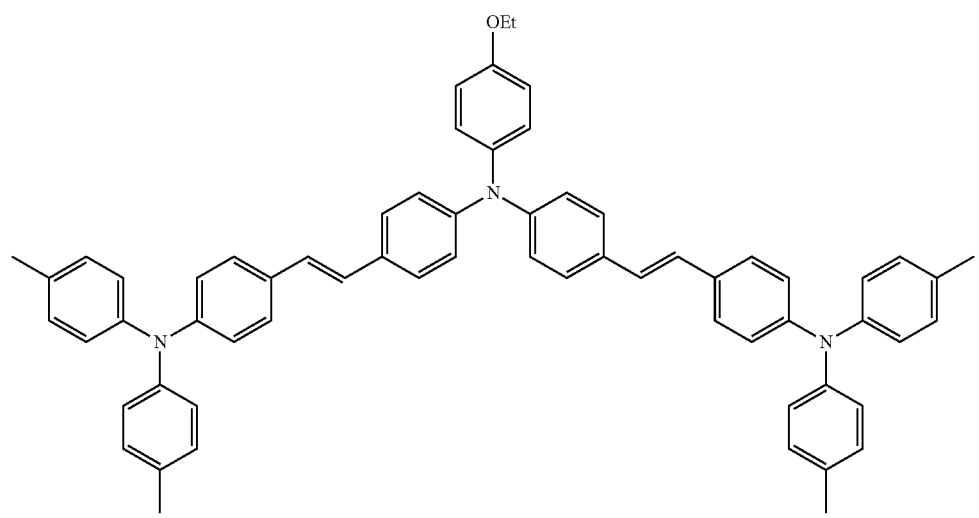
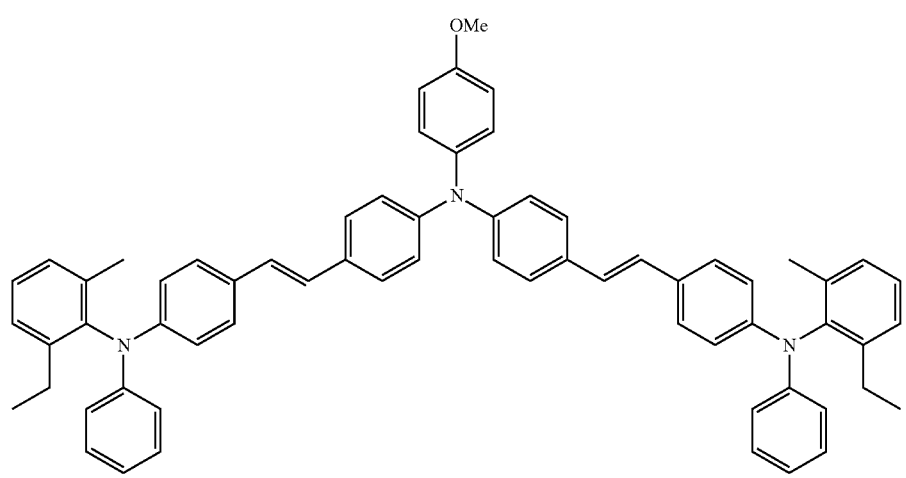

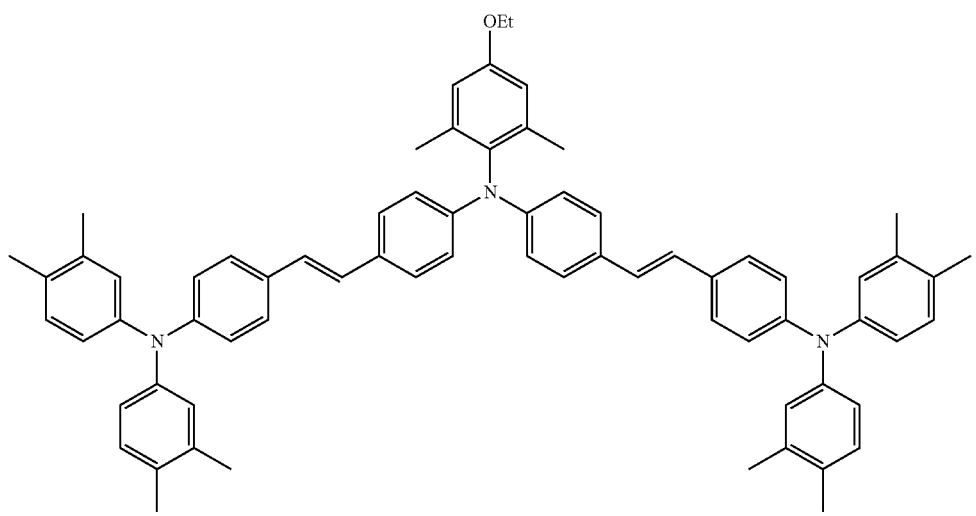
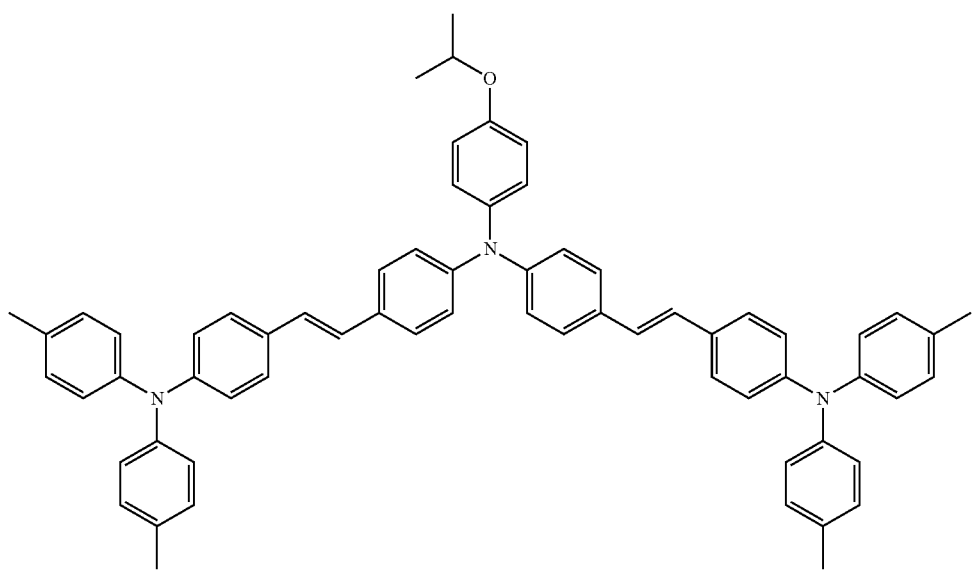
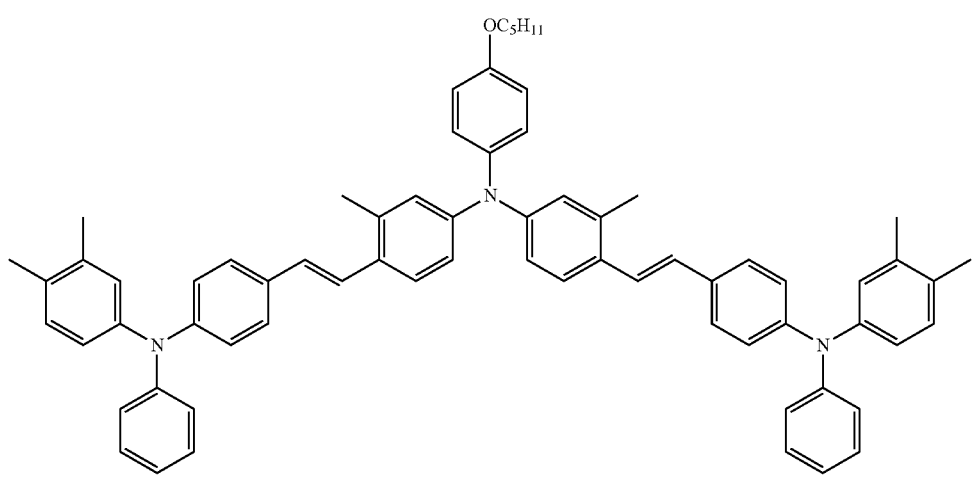

-continued
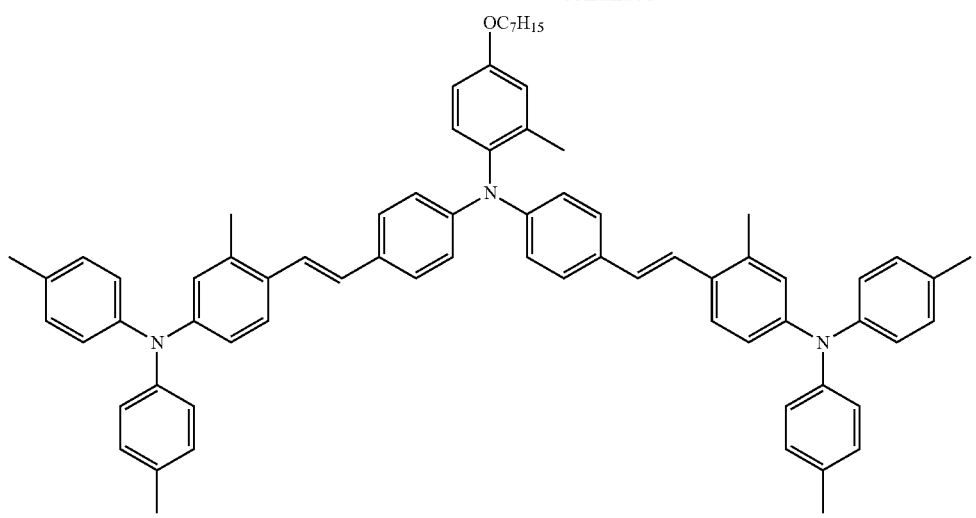
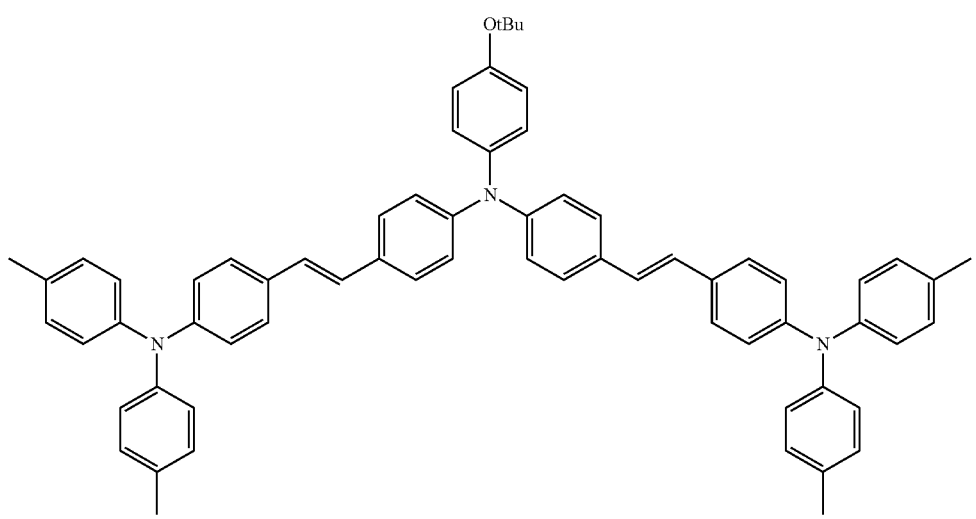
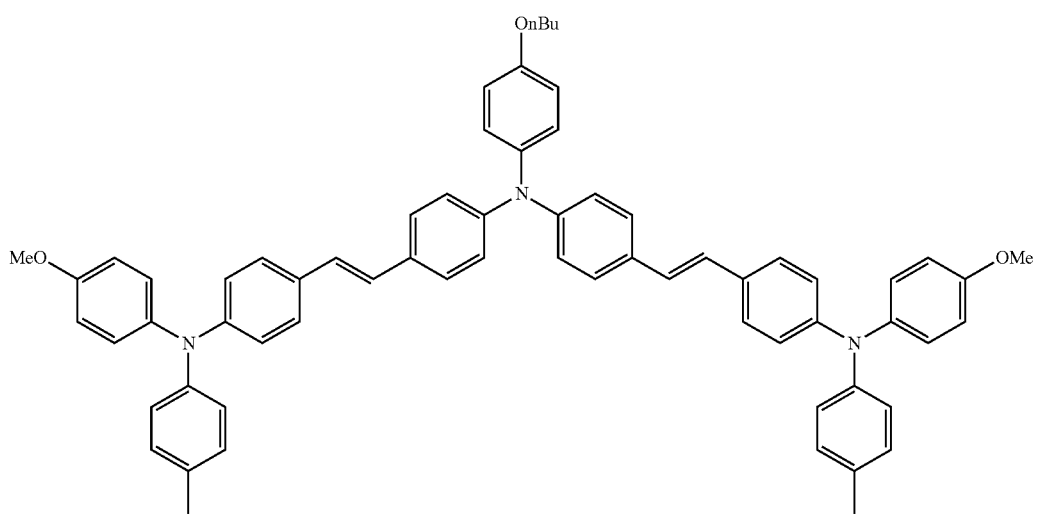

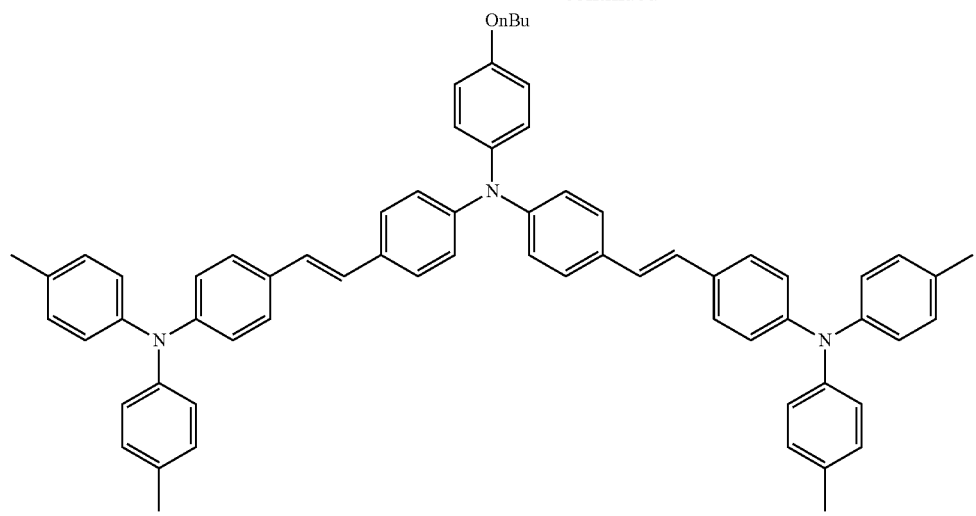
[Chem 8]
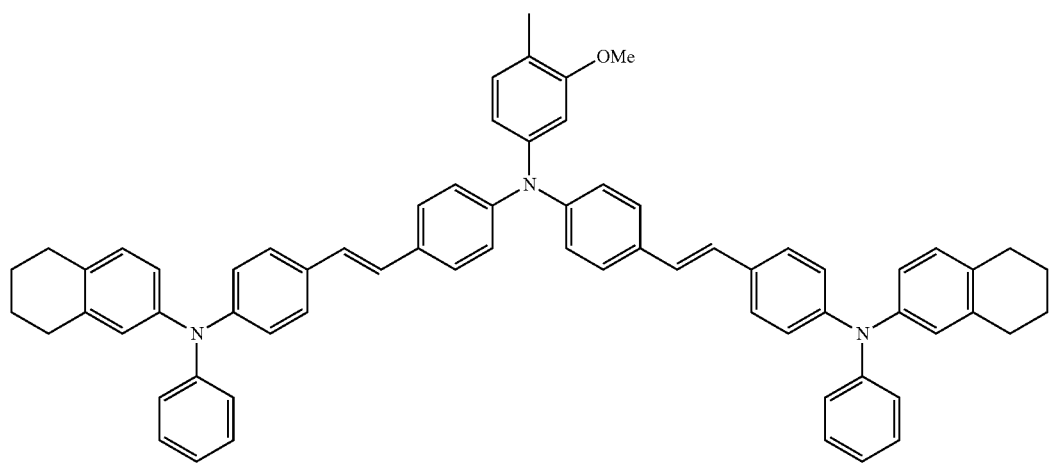
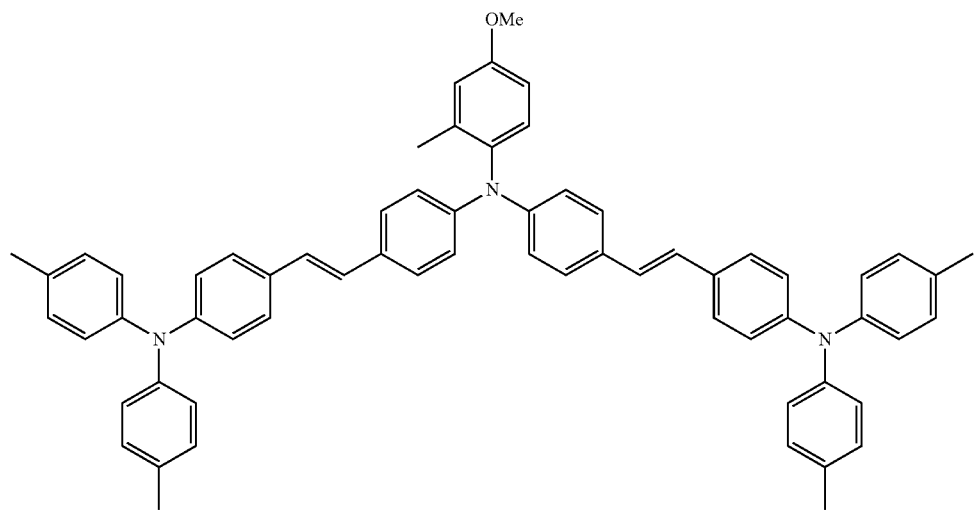

-continued
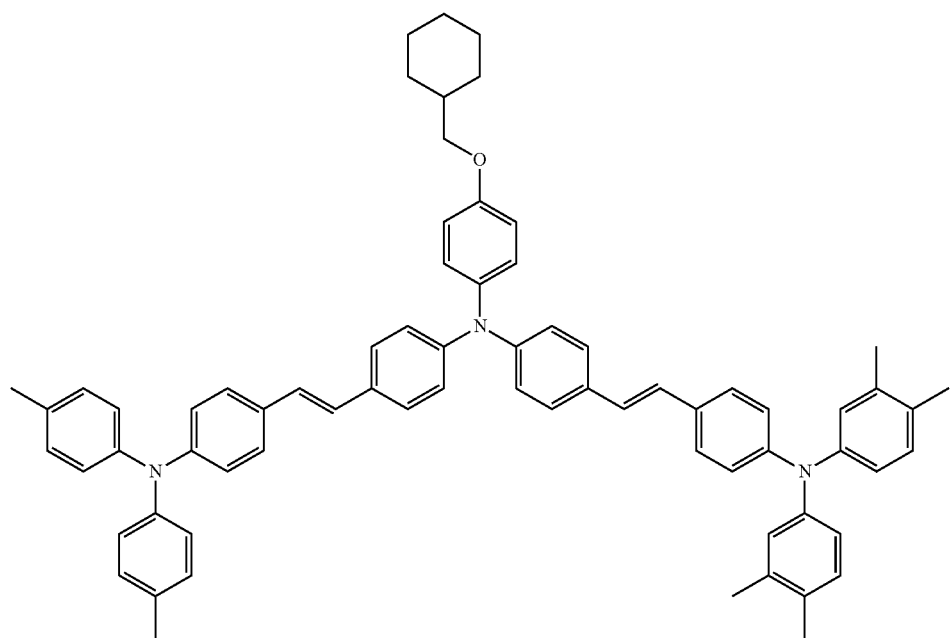
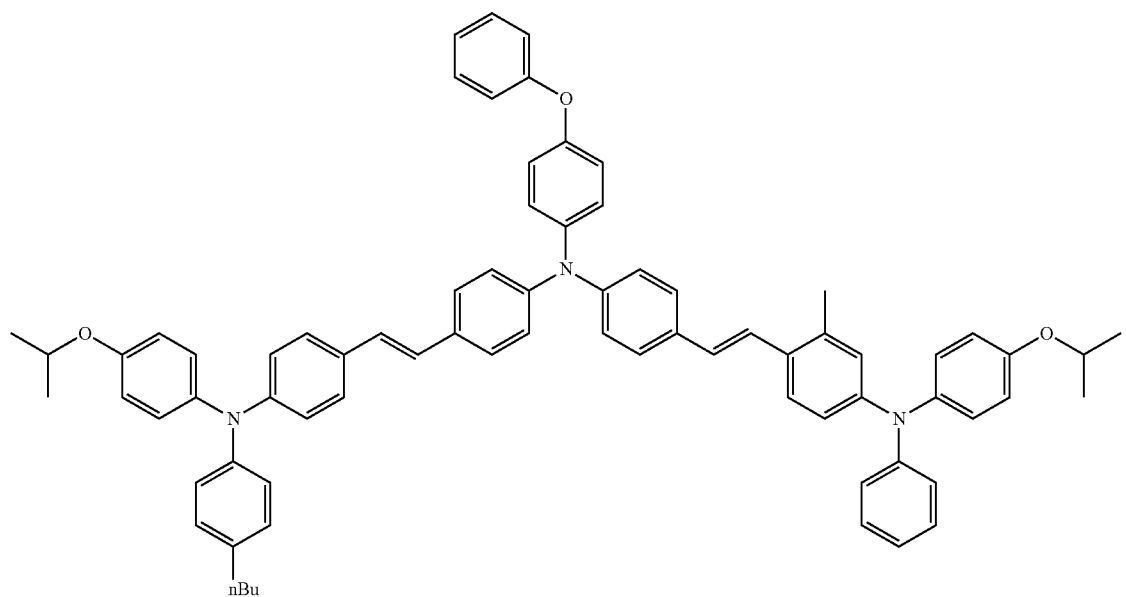

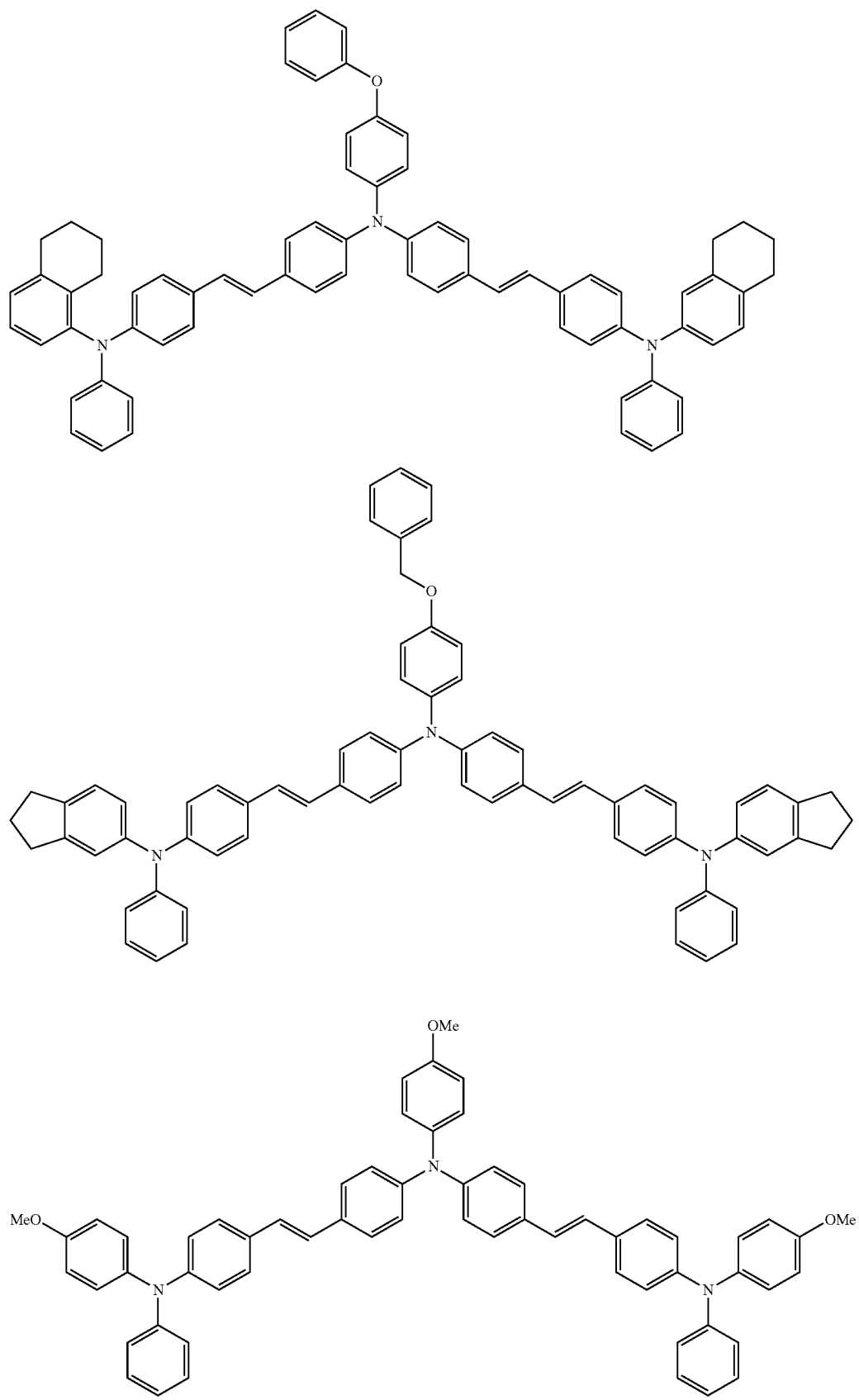

-continued
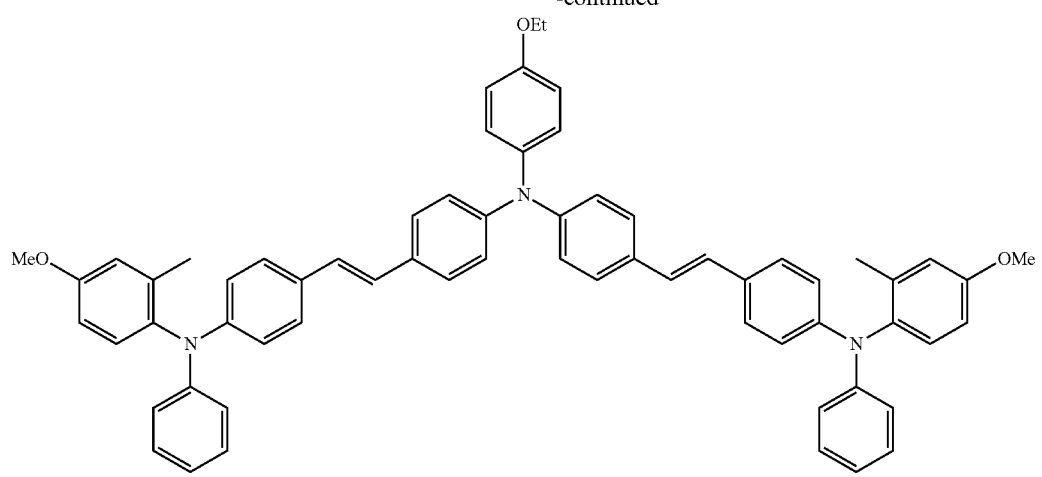
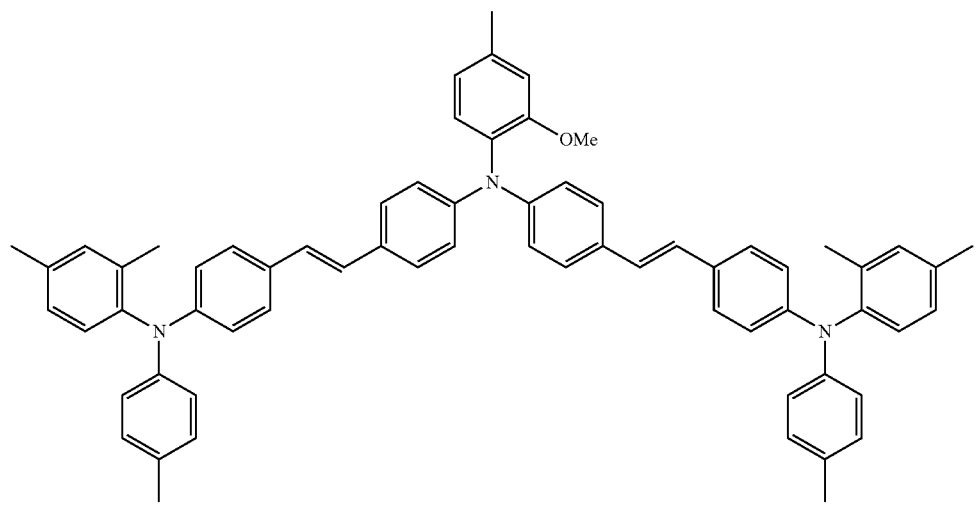
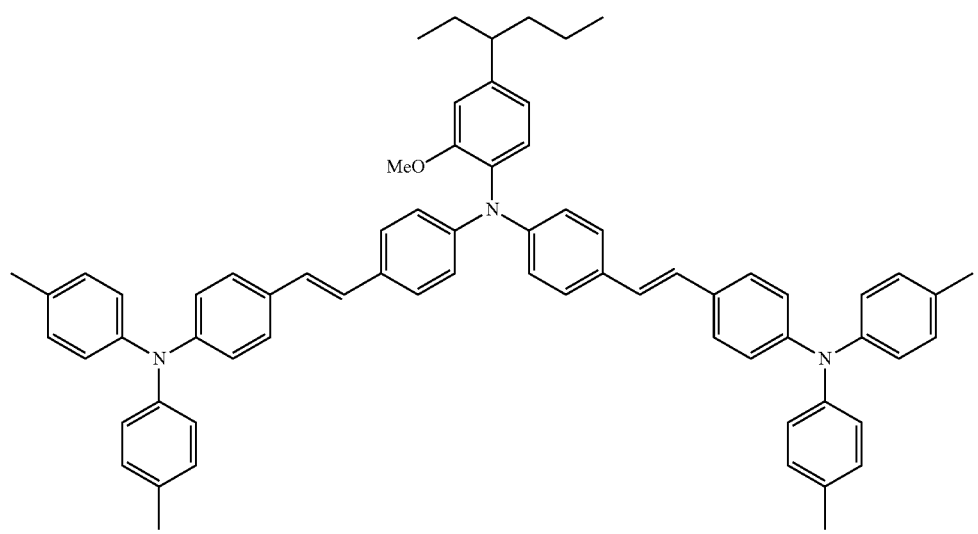

-continued
[Chem 9]
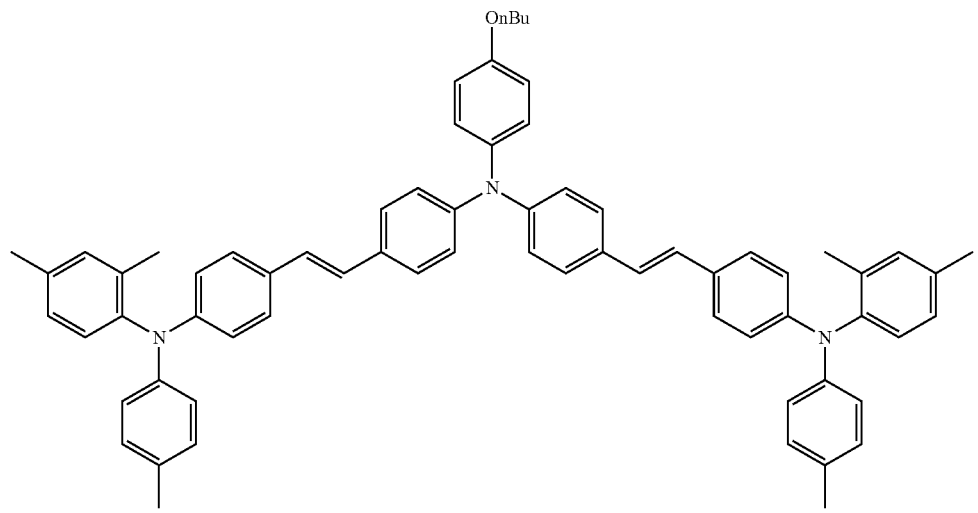
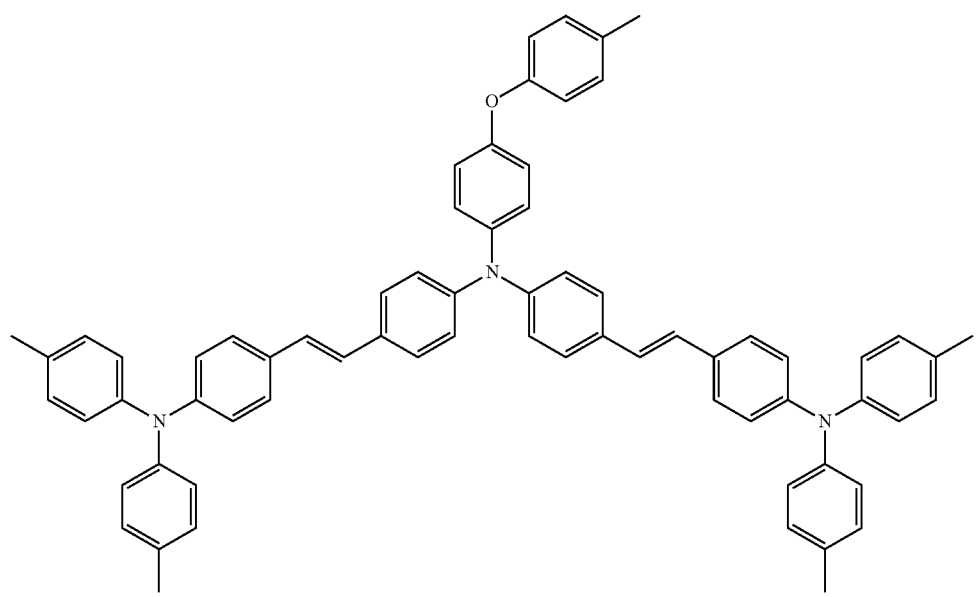
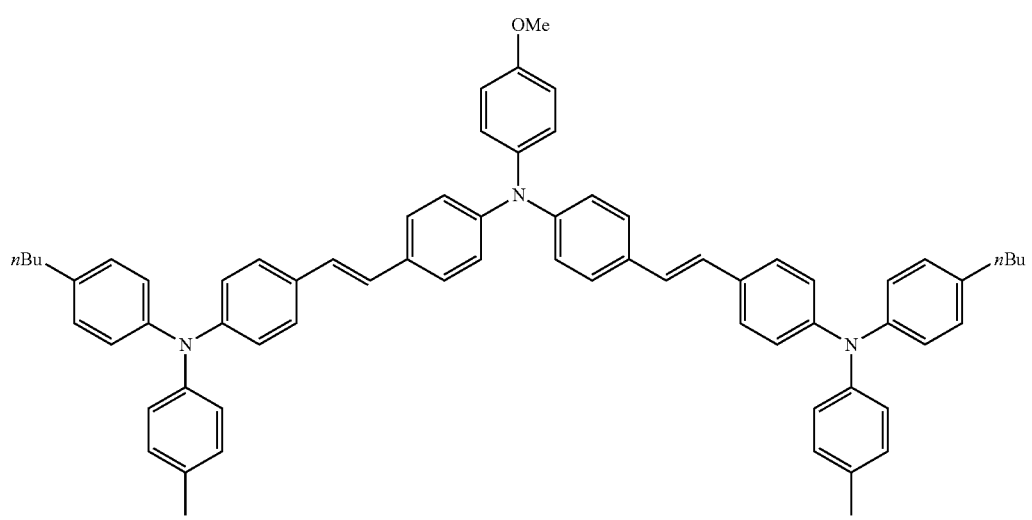

-continued
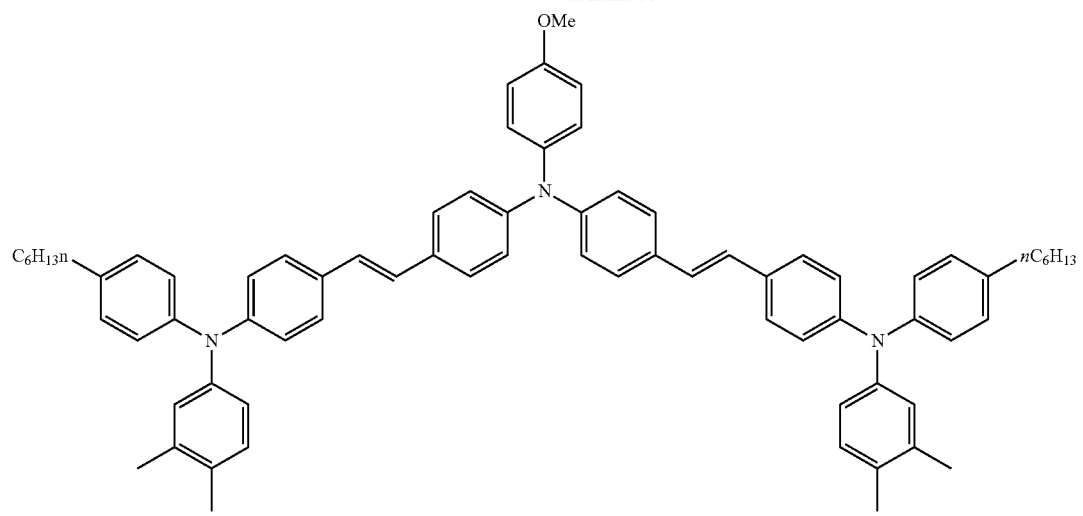
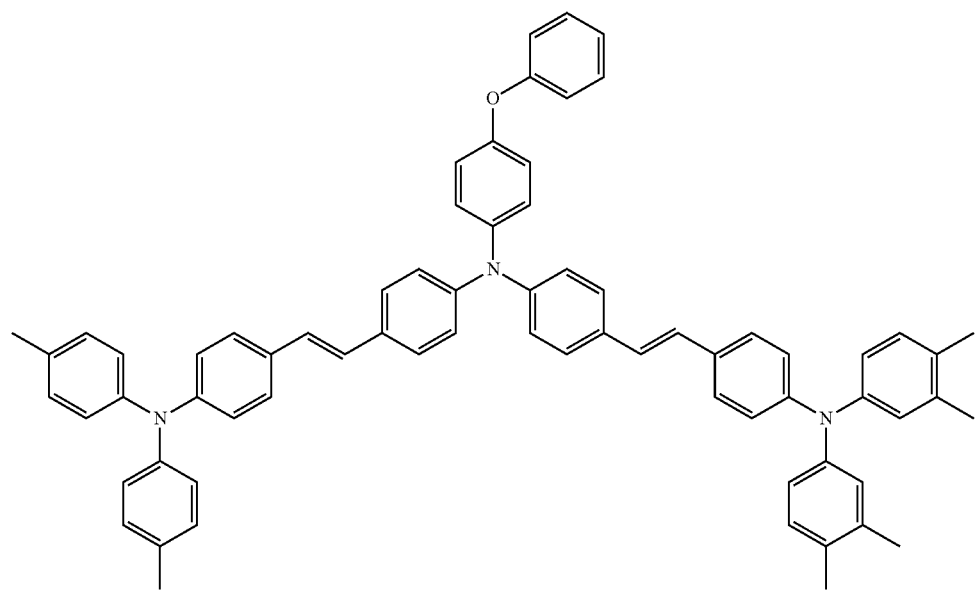
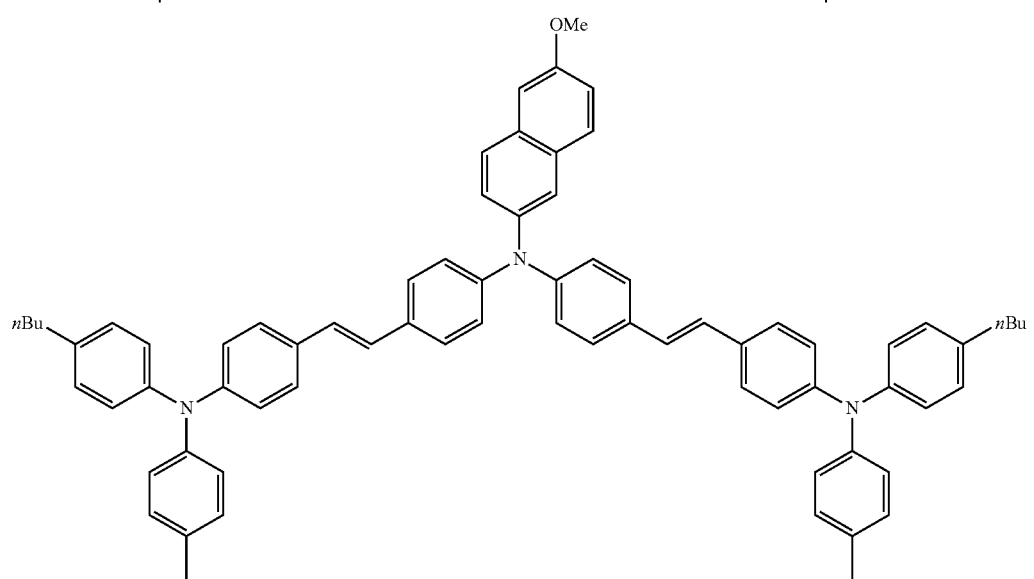

[Chem 10]
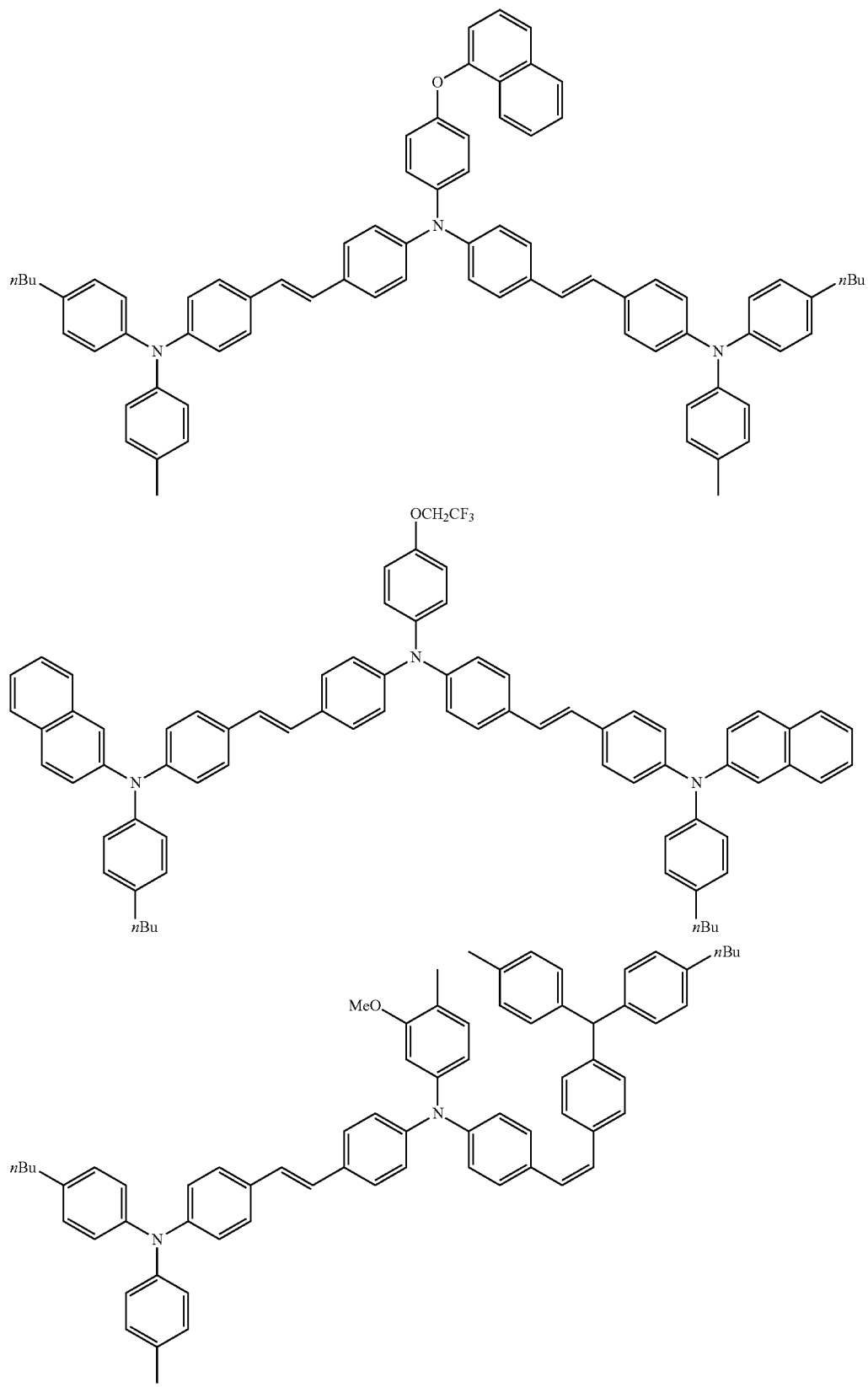

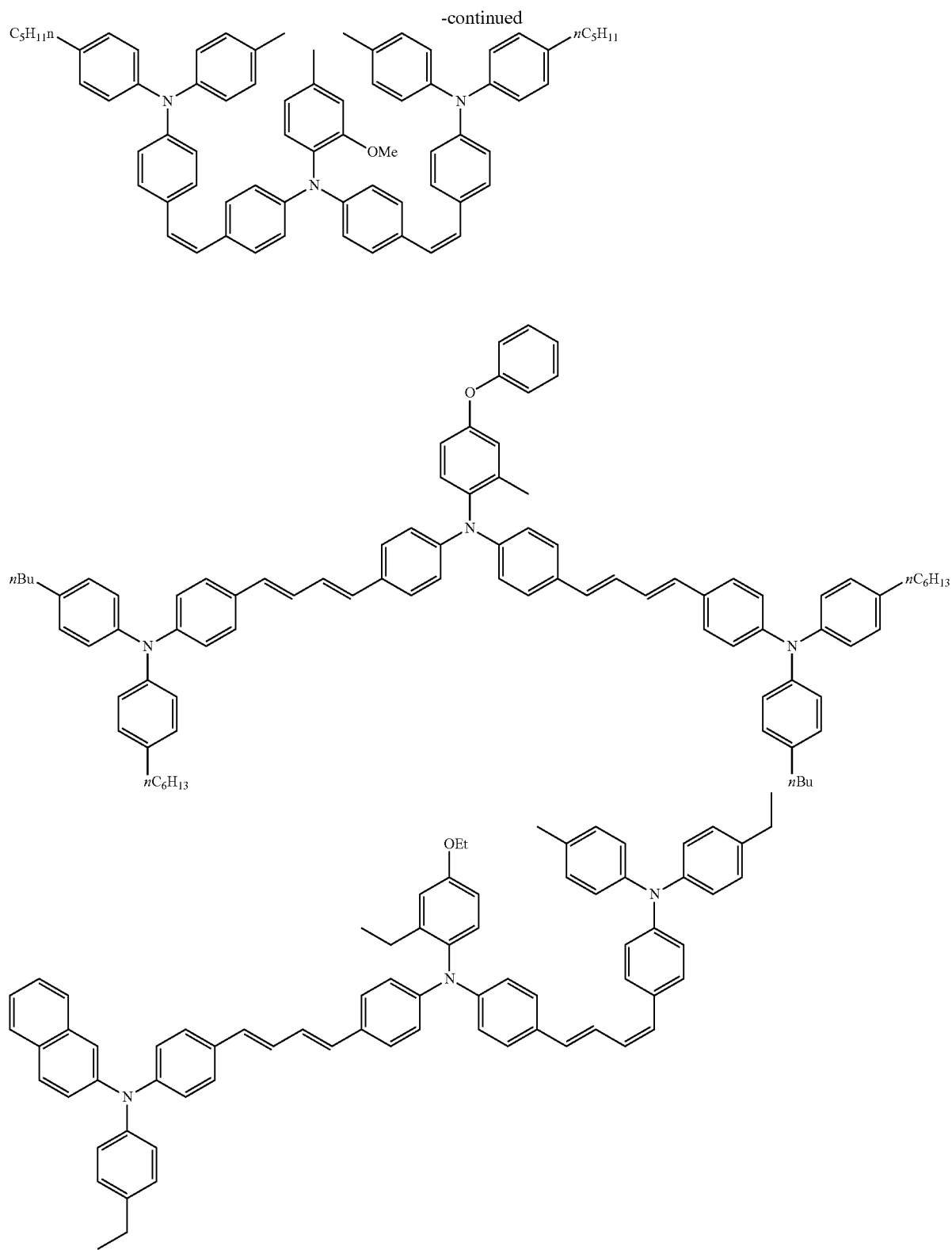

-continued

<Method for Manufacturing Charge Transport Substance of the Invention>

The charge transport substances illustrated above can be manufactured according to the scheme described below.

Using the compounds described above as examples, for example, they can be manufactured by reacting a compound having a triphenylamine skeleton having a formyl group with a phosphoric acid ester compound having a triphenylamine skeleton. (Scheme 1)

(Scheme 1)
[Chem 11]
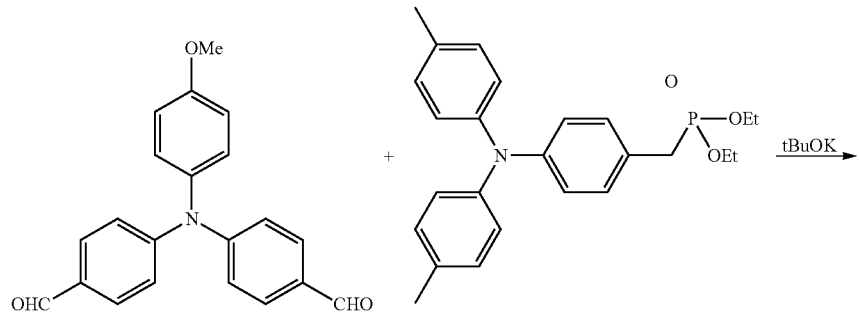
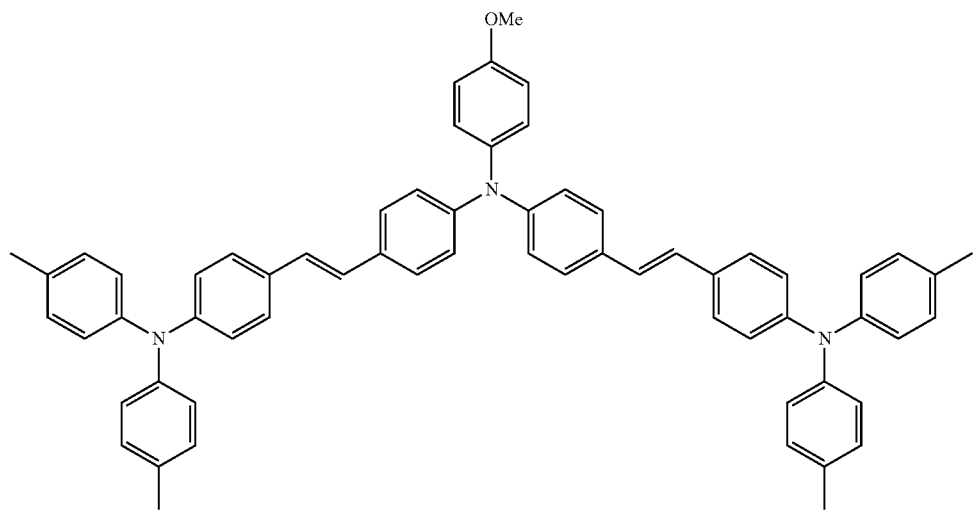
Furthermore, as another manufacturing method, it is possible to manufacture the compounds by subjecting a triphenylamine derivative having a halogen atom and an aniline compound as described below to a coupling reaction. (Scheme 2)
(Scheme 2)
[Chem 12]
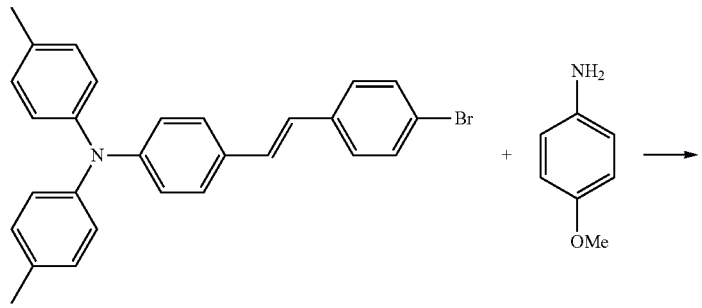

-continued

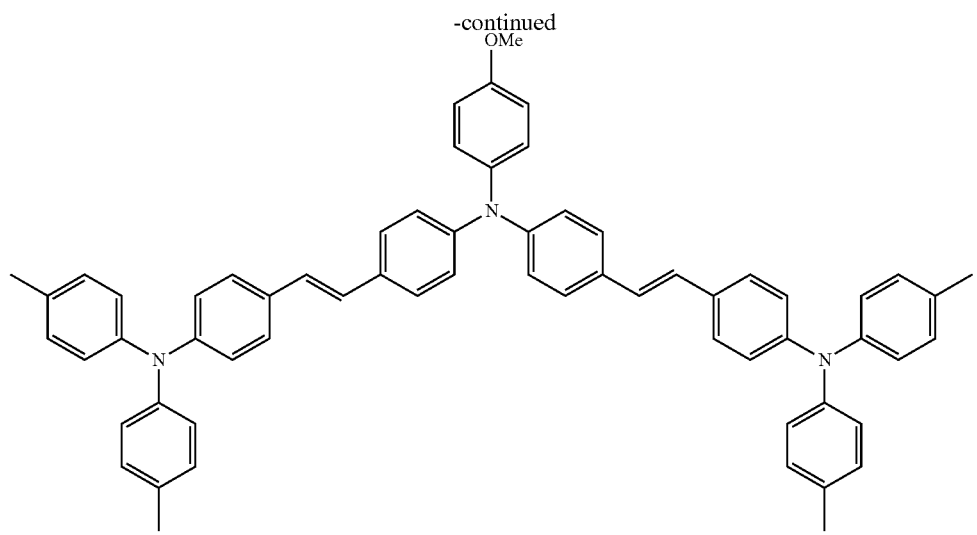

The above compounds can be identified by NMR, IR, mass spectrum, and the like.

The photosensitive layer of the electrophotographic photoreceptor typically contains a binder resin in addition to the charge transport substance. The ratio of the binder resin to the charge transport substance represented by the formula (1) in the photosensitive layer is usually 5 parts by mass or more based on 100 parts by mass of the binder resin in the same layer. Particularly, the ratio is preferably 10 parts by mass or more from the viewpoint of reducing the residual potential and more preferably 15 parts by mass or more from the viewpoint of the stability and charge mobility at the time of repeated use. On the other hand, from the viewpoint of thermal stability of the photosensitive layer, it is usually used in a ratio of 120 parts by mass or less. Particularly, the ratio is preferably 100 parts by mass or less from the viewpoint of compatibility between the charge transport substance and the binder resin, more preferably 90 parts by mass or less from the viewpoint of heat resistance, preferably 80 parts by mass or less from the viewpoint of scratch resistance, and particularly preferably 50 parts by mass or less from the viewpoint of abrasion resistance.

<Electroconductive Support>

There are no particular limitations on the electroconductive support constituting the electrophotographic photoreceptor. For example, there may be mainly used a metallic material such as aluminum, an aluminum alloy, stainless steel, copper, or nickel; a resinous material to which electrical conductivity has been imparted by adding thereto a conductive powder of a metal, carbon, tin oxide, or the like; or a resin, glass, paper, or the like having a surface on which a conductive material such as aluminum, nickel, or ITO (indium tin oxide) has been deposited by vapor deposition or application. One of these materials may be used alone, or any desired combination of two or more thereof may be used in any desired proportion.

The shape of the electroconductive support may be a drum, sheet, or belt form or another form. Furthermore, there may be used one obtained by applying, on an electroconductive support made of a metallic material, a conductive material having an appropriate resistivity for the purpose of regulating conductivity, surface properties, etc. or for the purpose of covering defects.

In the case where a metallic material such as an aluminum alloy is used as the electroconductive support, an anodized coating film may be formed thereon before the support is used. In the case where the anodized coating film has been formed, it is desirable to conduct a pore-filling treatment by a known method.

The surface of the electroconductive support may be smooth, or may have been roughened by using a special cutting technique or by conducting grinding. The electroconductive support may have a roughened surface obtained by incorporating particles having an appropriate particle diameter into the material constituting the electroconductive support. From the viewpoint of cost reduction, a drawn tube can be used as such without being subjected to cutting.

<Undercoat Layer>

An undercoat layer may be disposed between the electroconductive support and the photosensitive layer to be described later, in order to improve adhesiveness, non-blocking properties, etc. As the undercoat layer, there may be used, for example, a resin or a mixture of a resin and particles of a metal oxide or the like dispersed therein. The undercoat layer may be a layer constituted of a single layer, or may be a layer composed of a plurality of layers.

Examples of the metal oxide particles for use in the undercoat layer include particles of metal oxides containing one metallic element, such as titanium oxide, aluminum oxide, silicon oxide, zirconium oxide, zinc oxide, and iron oxide; particles of metal oxides containing a plurality of metallic elements, such as calcium titanate, strontium titanate, and barium titanate; and the like. One kind of the particles among these may be used alone, or a mixture of multiple kinds of the particles may be used.

Preferred of these particulate metal oxides are titanium oxide and aluminum oxide. Particularly preferred is titanium oxide. The surface of the titanium oxide particles may have undergone a treatment with an inorganic substance such as tin oxide, aluminum oxide, antimony oxide, zirconium oxide, or silicon oxide or with an organic substance such as stearic acid, a polyol, or a silicon. With respect to the crystal form of the titanium oxide particles, any of rutile, anatase, brookite, and amorphous ones can be used. Furthermore, the particles may include ones having a plurality of crystal states.

With respect to the particle diameter of the metal oxide particles, particles having various particle diameters can be utilized. Especially from the viewpoints of properties and the stability of the fluid, the average primary particle diameter thereof is preferably 10 nm or more and 100 nm or less, particularly preferably 10 nm or more and 50 nm or less. This average particle diameter can be obtained, for example, from a TEM photograph.

It is desirable that the undercoat layer should be formed as a layer in which particles of a metal oxide have been dispersed in a binder resin.

As the binder resin usable for the undercoat layer, there may be mentioned known binder resins such as epoxy resins, polyethylene resins, polypropylene resins, acrylic resins, methacrylic resins, polyamide resins, vinyl chloride resins, vinyl acetate resins, phenolic resins, polycarbonate resins, polyurethane resins, polyimide resins, vinylidene chloride resins, polyvinyl acetal resins, vinyl chloride/vinyl acetate copolymers, polyvinyl alcohol resins, polyacrylic resins, polyacrylamide resins, polyvinylpyrrolidone resins, polyvinylpyridine resins, water-soluble polyester resins, cellulose ester resins including nitro cellulose and the like, cellulose ether resins, casein, gelatin, polyglutamic acid, starch, starch acetate, aminostarch, organozirconium compounds including zirconium chelate compounds, zirconium alkoxide compounds, and the like, organic titanyl compounds including titanyl chelate compounds, titanium alkoxide compounds, and the like, and silane coupling agents. One of these binder resins may be used alone, or any desired combination of two or more thereof may be used in any desired proportion. A binder resin may be incorporated together with a curing agent to use the resin in a cured state. Especially, alcohol-soluble copolyamides, modified polyamides, and the like are preferable because they show satisfactory dispersibility and applicability.

The ratio of the inorganic particles to be used, to the binder resin to be used for the undercoat layer, can be arbitrarily selected but, in view of the stability and applicability of the dispersion, it is preferred to use the particles in a ratio usually ranging from 10% by mass or more and 500% by mass or less based on the binder resin.

The undercoat layer may have any desired thickness unless the effects of the invention are considerably impaired. However, from the viewpoint of improving the electrical properties, suitability for intense exposure, image-forming properties, and repeatability of the electrophotographic photoreceptor and applicability during manufacture, the thickness thereof is usually 0.01 µm or more, preferably 0.1 µm or more, and is usually 30 µm or less, preferably 20 µm or less.

A known antioxidant and the like may be incorporated into the undercoat layer. Pigment particles, resin particles, or the like may be used for the purpose of, for example, preventing image defects.

<Photosensitive Layer>

The photosensitive layer is formed on the electroconductive support described above (when the undercoat layer described above has been disposed, the photosensitive layer is formed on the undercoat layer). The photosensitive layer is a layer which contains a charge transport substance represented by the general formula (1) described above. As the type thereof, there may be mentioned a photosensitive layer of a single-layer structure in which a charge generation material and a charge transport material (including the charge transport substance of the invention) are present in the same layer and these materials have been dispersed in a binder resin (hereinafter suitably referred to as "single-layer type photosensitive layer"); and a photosensitive layer of the function-separated type having a multilayer structure composed of two or more layers including a charge generation layer in which a charge generation material has been dispersed in a binder resin and a charge transport layer in which a charge transport material (including the charge transport substance of the invention) has been dispersed in a binder resin (hereinafter suitably referred to as "multilayer type photosensitive layer"). The photosensitive layer may be either of these types.

As the multilayer type photosensitive layer, there may be mentioned a normal-lamination type photosensitive layer obtained by laminating a charge generation layer and a charge transport layer in this order from the electroconductive support side and a reverse-lamination type photosensitive layer obtained by laminating the two layers in the reverse order, i.e., in the order of a charge transport layer and a charge generation layer from the electroconductive support side. Although either of these photosensitive layers can be employed, the normal-lamination type photosensitive layer, which is capable of exhibiting most balanced photoconductivity, is preferred.

<Multilayer Type Photosensitive Layer>

[Charge Generation Layer]

The charge generation layer of the multilayer type photosensitive layer (function-separated type photosensitive layer) contains a charge generation material and usually further contains a binder resin and other ingredients which are used according to need. Such a charge generation layer can be obtained, for example, by dissolving or dispersing a charge generation material and a binder resin in a solvent or dispersion medium to produce a coating fluid, applying this coating fluid on a electroconductive support (or on an undercoat layer when the undercoat layer has been disposed) in the case of a normal-lamination type photosensitive layer or applying the coating fluid on a charge transport layer in the case of a reverse-lamination type photosensitive layer, and drying the coating fluid applied.

As the charge generation material, there may be mentioned inorganic photoconductive materials such as selenium, alloys thereof, and cadmium sulfide and organic photoconductive materials such as organic pigments. However, organic photoconductive materials are preferred, and organic pigments are especially preferred of these.

Examples of the organic pigments include phthalocyanine pigments, azo pigments, dithioketopyrrolopyrrole pigments, squalene (squarylium) pigments, quinacridone pigments, indigo pigments, perylene pigments, polycyclic quinone pigments, anthanthrone pigments, benzimidazole pigments, and the like. Especially preferred of these are phthalocyanine pigments or azo pigments.

In the case where an organic pigment is used as a charge generation material, any of these organic pigments is used usually in the form of a dispersion layer in which fine particles of the pigment have been bound with any of various binder resins.

In the case where a phthalocyanine pigment is used as a charge generation material, there may be specifically used phthalocyanines having different crystal forms such as metal-free phthalocyanine and phthalocyanine compounds to which a metal, e.g., copper, indium, gallium, tin, titanium, zinc, vanadium, silicon, germanium, or aluminum, or an oxide, halide, hydroxide, alkoxide, or another form of the metal has coordinated; and phthalocyanine dimmers or the like in which an oxygen atom or the like is used as a crosslinking atom. Especially, suitable are X-form and t-form metal-free phthalocyanines, which are crystal forms having high sensitivity, A-form (also called β-form), B-form (also called α-form), D-form (also called Y-form), and other titanyl phthalocyanines (another name: oxytitanium phthalocyanines), vanadyl phthalocyanines, chloroindium phthalocyanines, hydroxyindium phthalocyanines, II-form and other chlorogallium phthalocyanines, V-form and other hydroxygallium phthalocyanines, G-form, I-form, and other μ-oxogallium phthalocyanine dimers, and II-form and other μ-oxoaluminum phthalocyanine dimers.

Moreover, among these phthalocyanines, metal phthalocyanines are preferred, more preferred are A-form (also called β-form), B-form (also called α-form) and D-form (Y-form) titanyl phthalocyanine which shows a distinct peak at a diffraction angle 2θ (±0.2°) of 27.2° in powder X-ray diffractometry, II-form chlorogallium phthalocyanine, V-form hydroxygallium phthalocyanine, G-form μ-oxo-gallium phthalocyanine dimer, and the like. Further preferred is oxytitanium phthalocyanine in view of production stability.

Among the oxytitanium phthalocyanine crystals, preferred is a crystal having main diffraction peaks at Bragg angles (2θ±0.2°) of 24.1° and 27.2° for a CuKα characteristic X-ray (wavelength 1.541 Å). As the other diffraction peaks, since a crystal having a peak at around 26.2° is inferior in crystal stability at the time of dispersion, it is preferable not to have a peak in the vicinity of 26.2°. Especially, a crystal having main diffraction peaks at 7.3°, 9.6°, 11.6°, 14.2°, 18.0°, 24.1° and 27.2° or at 7.3°, 9.5°, 9.7°, 11.6°, 14.2°, 18.0°, 24.2° and 27.2° is preferred in view of the dark decay and the residual potential when used as an electrophotographic photoreceptor.

The powder X-ray diffraction spectrum with a CuKα characteristic X-ray in the invention will be measured based on the following method.

(Powder XRD Measurement Conditions)

As the measurement apparatus for measuring the powder X-ray diffraction spectrum, there was used PW1700 manufactured by PANalytical Company, which is a powder X-ray diffractometer of a concentrated optical system using a CuKa line as a radiation source. Measurement conditions are as follows: X-rays output: 40 kV, 30 mA, Scanning range (2θ): 3 to 40°, Scan step width: 0.05°, Scanning speed: 3.0°/min, Divergence slit: 1.0°, Scattering slit: 1.0°, and Receiving slit: 0.2 mm.

Furthermore, in the oxytitanium phthalocyanine crystal, the ratio of chlorinated oxytitanium phthalocyanine represented by the following formula [L] to non-substituted oxytitanium phthalocyanine represented by the following formula [M] is 0.070 or less in terms of a mass spectrum intensity ratio. Also, the mass spectrum intensity ratio is preferably 0.060 or less, more preferably 0.055 or less. At the time of manufacture, in the case of using a dry grinding method for amorphization, the ratio is preferably 0.02 or more and, in the case of using an acid paste method for amorphization, the ratio is preferably 0.03 or less. The amount of chlorine substitution is measured based on the method described in JP-A-2001-115054.

Incidentally, m/z described under the formula [M] and the formula [L] represents the ratio of mass m and the charge z to be obtained in a mass spectrum.

[Chem 13]

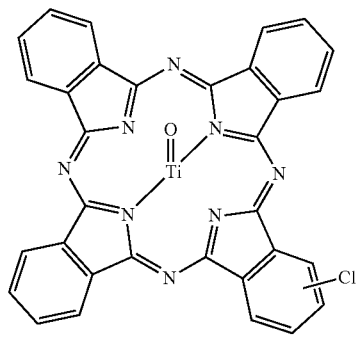

m/z: 610

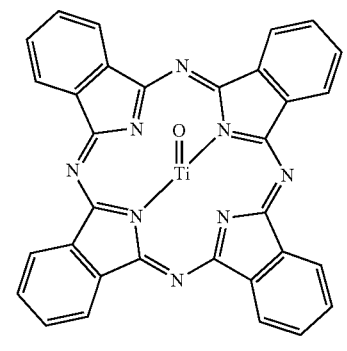

m/z: 576

As preparation methods of low crystalline phthalocyanine, amorphous phthalocyanine to be a precursor of oxytitanium phthalocyanine that have a major distinct diffraction peak at a Bragg angle (2θ±0.2°) of 27.2° in the powder X-ray diffraction spectrum with a CuKa characteristic X-ray, which is a suitable oxytitanium phthalocyanine for the invention, it is possible to use well-known preparation methods including chemical treatments such as the acid paste method and the acid slurry method and mechanical treatments such as pulverization and grinding.

In the case where a metal-free phthalocyanine compound or a metal-containing phthalocyanine compound is used as a charge generation material, a photoreceptor which is highly sensitive to relatively long-wavelength laser light, e.g., laser light having a wavelength of about 780 nm, is obtained. In the case where an azo pigment such as a monoazo, diazo, or trisazo pigment is used, it is possible to obtain a photoreceptor which has sufficient sensitivity to white light, laser light having a wavelength of about 660 nm, or laser light having a relatively short wavelength (e.g., laser light having a wavelength in the range of 380 nm to 500 nm).

A single phthalocyanine compound may be used alone, or a mixture of some phthalocyanine compounds or one in a mixed crystal state may be used. This mixed state of individual phthalocyanine compounds or of crystal states to be used here may be a mixture obtained by mixing the components prepared beforehand, or may be a mixture which came into the mixed state during phthalocyanine compound manufacture/treatment steps such as synthesis, pigment formation, crystallization, etc. Known as such treatment steps include an acid paste treatment, a grinding treatment, a solvent treatment, and the like.

For obtaining a mixed-crystal state, there may be mentioned a method in which two kinds of crystals are mixed, subsequently mechanically ground to render the crystals amorphous, and then subjected to a solvent treatment to perform conversion into specific crystal states, as described in JP-A-10-48859.

Meanwhile, in the case of using an azo pigment as a charge generation material, conventionally known various azo pigments can be used so long as the azo pigments have sensitivity to the light source for light input. However, various kinds of bisazo pigments and trisazo pigments are suitably used.

In the case where the organic pigments shown above as examples are used as a charge generation material, one of the azo pigments may be used alone but two or more pigments may be used as a mixture thereof. In this case, it is preferred that two or more charge generation materials which have spectral sensitivity characteristics in different spectral regions, i.e., the visible region and the near-infrared region, are used in combination. Especially, more preferred is to use a disazo pigment or trisazo pigment and a phthalocyanine pigment in combination.

The binder resin to be used for the charge generation layer as a component of the multilayer type photosensitive layer is not particularly limited. Examples thereof include insulating resins such as polyvinyl acetal resins, e.g., polyvinyl butyral resins, polyvinyl formal resins, and partly acetalized polyvinyl butyral resins in which the butyral moieties have been partly modified with formal, acetal, or the like, polyarylate resins, polycarbonate resins, polyester resins, modified ether-based polyester resins, phenoxy resins, polyvinyl chloride resins, polyvinylidene chloride resins, polyvinyl acetate resins, polystyrene resins, acrylic resins, methacrylic resins, polyacrylamide resins, polyamide resins, polyvinylpyridine resins, cellulosic resins, polyurethane resins, epoxy resins, silicone resins, polyvinyl alcohol resins, polyvinylpyrrolidone resins, casein, vinyl chloride-vinyl acetate-based copolymers, e.g., vinyl chloride/vinyl acetate copolymers, hydroxy-modified vinyl chloride/vinyl acetate copolymers, carboxyl-modified vinyl chloride/vinyl acetate copolymers, and vinyl chloride/vinyl acetate/maleic anhydride copolymers, styrene/butadiene copolymers, vinylidene chloride/acrylonitrile copolymers, styrene-alkyd resins, silicone-alkyd resins, and phenol-formaldehyde resins; organic photoconductive polymers such as poly-N-vinylcarbazole, polyvinylanthracene, and polyvinylperylene; and the like. Any one of these binder resins may be used alone, or any desired combination of two or more thereof may be used as a mixture thereof.

The charge generation layer is formed specifically by dissolving the binder resin described above in an organic solvent, dispersing a charge generation material in the resulting solution to prepare a coating fluid, and applying this coating fluid on a electroconductive support (or on an undercoat layer when the undercoat layer has been disposed).

The solvent to be used for producing the coating fluid is not particularly limited so long as the binder resin dissolves therein. Examples thereof include saturated aliphatic solvents such as pentane, hexane, octane, and nonane; aromatic solvents such as toluene, xylene, and anisole; halogenated aromatic solvents such as chlorobenzene, dichlorobenzene, and chloronaphthalene; amide solvents such as dimethylformamide and N-methyl-2-pyrrolidone; alcohol solvents such as methanol, ethanol, isopropanol, n-butanol, and benzyl alcohol; aliphatic polyhydric alcohols such as glycerol and polyethylene glycol; chain or cyclic ketone solvents such as acetone, cyclohexanone, methyl ethyl ketone, and 4-methoxy-4-methyl-2-pentanone; ester solvents such as methyl formate, ethyl acetate, and n-butyl acetate; halogenated hydrocarbon solvents such as methylene chloride, chloroform, and 1,2-dichloroethane; chain or cyclic ether solvents such as diethyl ether, dimethoxyethane, tetrahydrofuran, 1,4-dioxane, methyl cellosolve, and ethyl Cellosolve; aprotic polar solvents such as acetonitrile, dimethyl sulfoxide, sulfolane, and hexamethylphosphoric triamide; nitrogen-containing compounds such as n-butylamine, isopropanolamine, diethylamine, triethanolamine, ethylenediamine, triethylenediamine, and triethylamine; mineral oils such as ligroin; water; and the like. Any one of these solvents may be used alone, or two or more thereof may be used in combination. In the case where the undercoat layer described above is disposed, solvents in which this undercoat layer does not dissolve are preferred.

In the charge generation layer, the mixing ratio (mass ratio) of the binder resin to the charge generation material is in such a range that the amount of the charge generation material per 100 parts by mass of the binder resin is usually 10 parts by mass or more, preferably 30 parts by mass or more, and is usually 1,000 parts by mass or less, preferably 500 parts by mass or less.

The thickness of the charge generation layer is usually 0.1 μm or more, preferably 0.15 μm or more, and is usually 10 μm or less, preferably 0.6 μm or less. In the case where the proportion of the charge generation material is too high, there is a possibility that the coating fluid might have reduced stability due to e.g., the aggregation of the charge generation material. On the other hand, in the case where the proportion of the charge generation material is too low, there is a possibility of inviting a decrease in the sensitivity as a photoreceptor.

For dispersing the charge generation material, known dispersing methods can be used, such as a ball-mill dispersing method, an attritor dispersing method, and a sand-mill dispersing method. On this occasion, it is preferred to finely pulverize the particles to a particle size of 0.5 μm or less, preferably 0.3 μm or less, more preferably 0.15 μm or less.

<Charge Transport Layer>

The charge transport layer of the multilayer type photoreceptor contains a charge transport substance, a binder resin, and other ingredients which are used according to need. Such a charge transport layer can be obtained, specifically, by dissolving or dispersing a charge transport substance, etc. and a binder resin in a solvent to produce a coating fluid, applying this coating fluid on the charge generation layer in the case of a normal-lamination type photosensitive layer or applying the coating fluid on a electroconductive support (or on an undercoat layer when the undercoat layer has been disposed) in the case of a reverse-lamination type photosensitive layer, and drying the coating fluid applied.

Preferred as the charge transport substance is a charge transport substance represented by the formula (1) described above. A known other charge transport substance may be further used in combination with the charge transport substance represented by the formula (1) described above.

In the case of using the other charge transport substance in combination, the kind thereof is not particularly limited. However, preferred are, for example, carbazole derivatives, hydrazone compounds, aromatic amine derivatives, enamine derivatives, butadiene derivatives, and compounds each constituted of two or more of these derivatives bonded to each other.

The following show specific examples of suitable structures of the charge transport substances which can be used in combination in addition to the charge transport substance represented by the formula (1) described above. These specific examples are those given by way of illustration and it is possible to use any known charge transport substances unless they are contrary to the spirit of the invention.

[Chem 14]

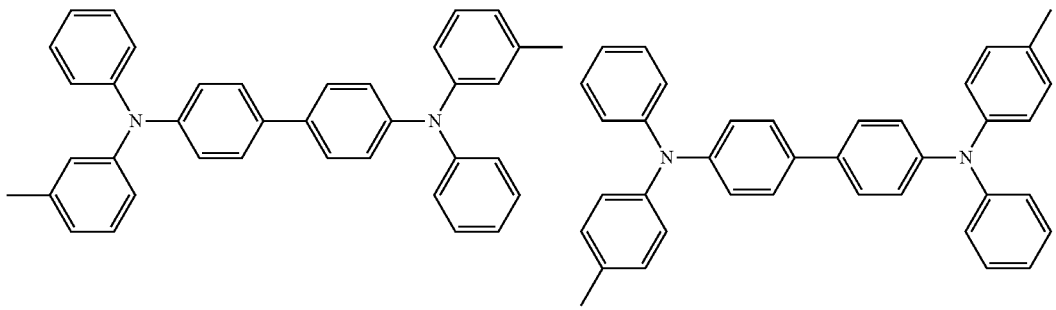

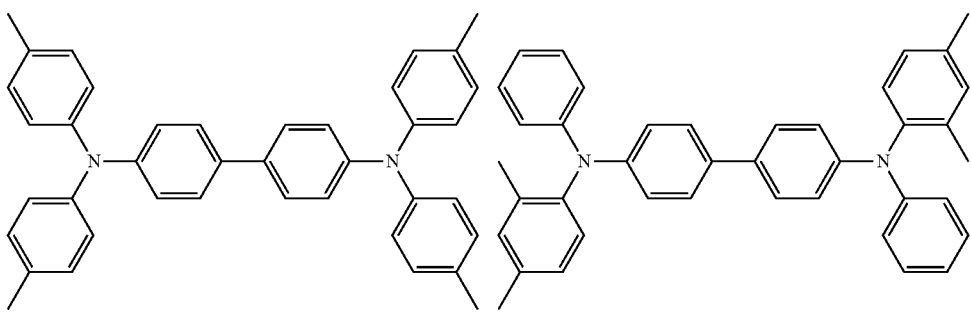

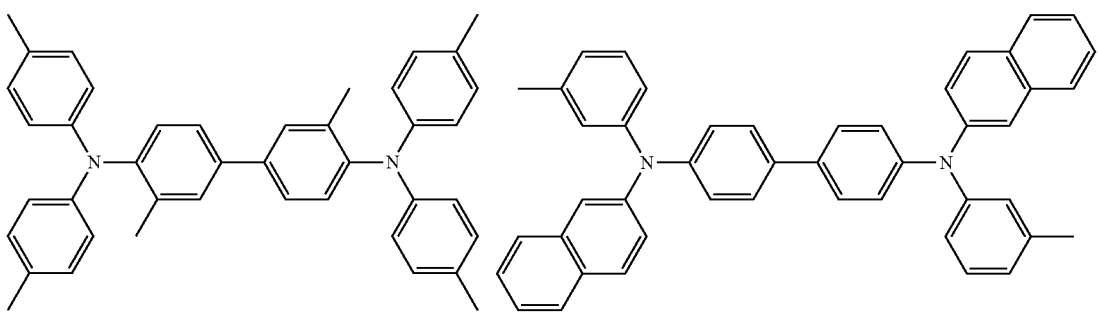

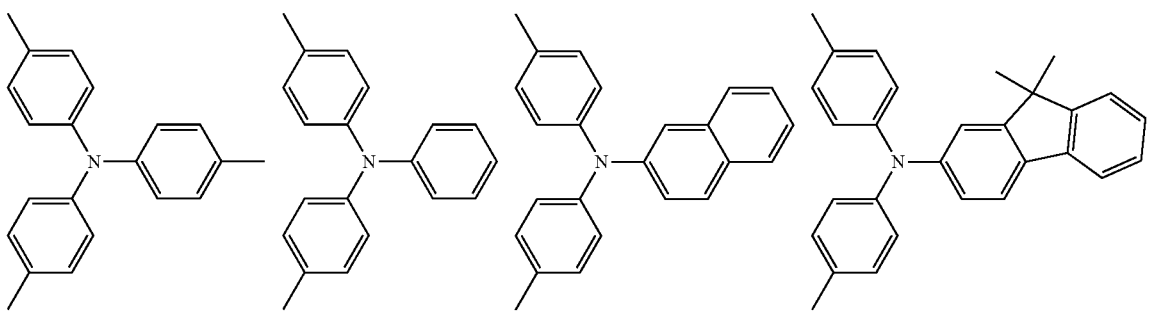

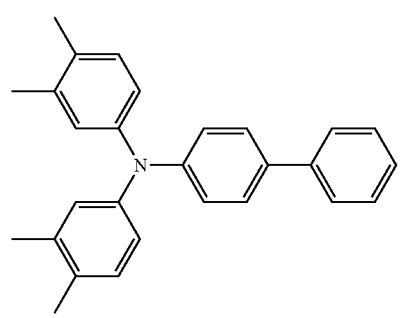
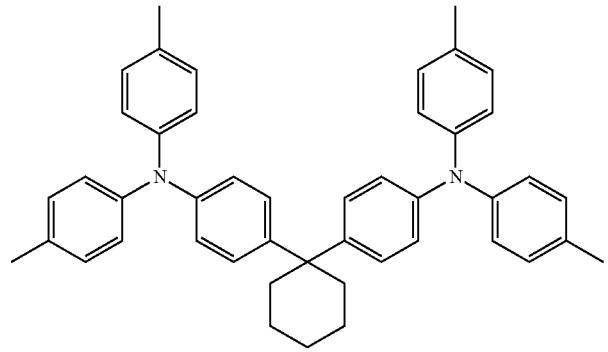
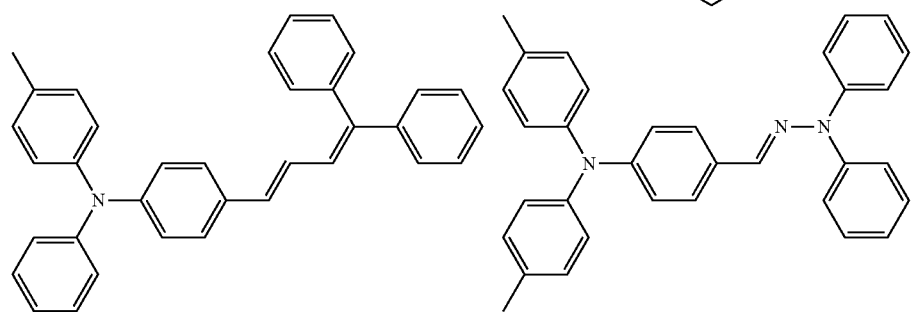
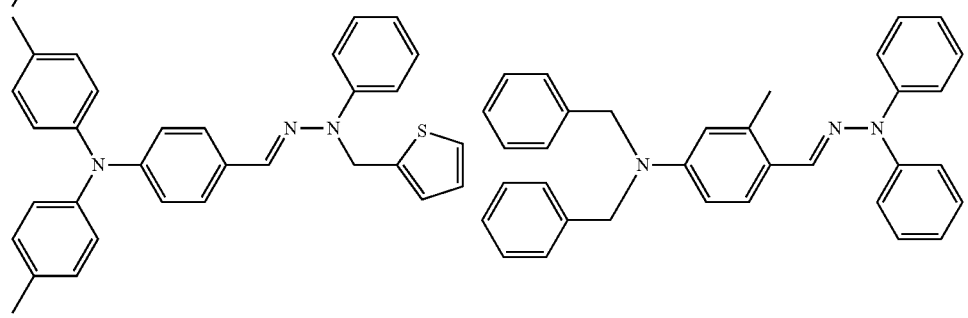
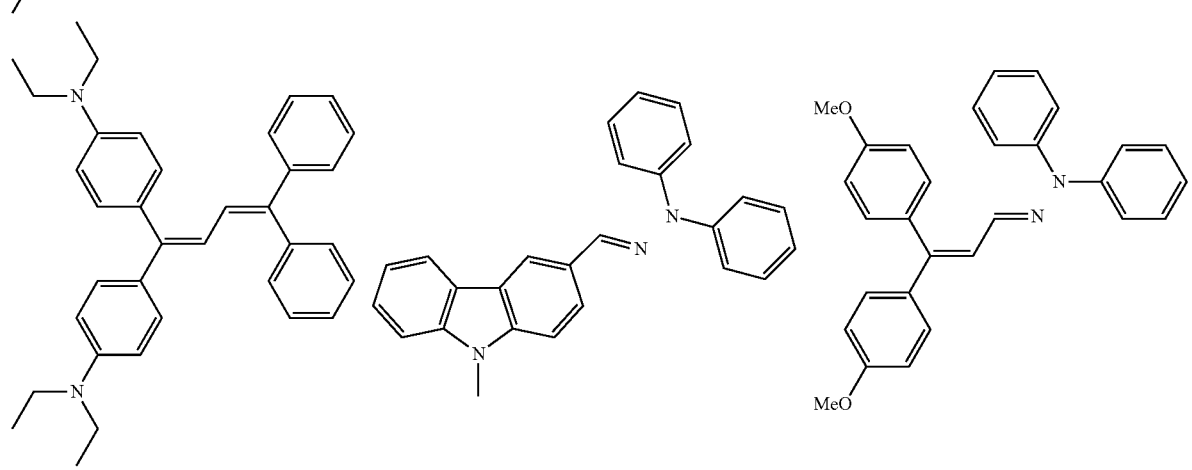
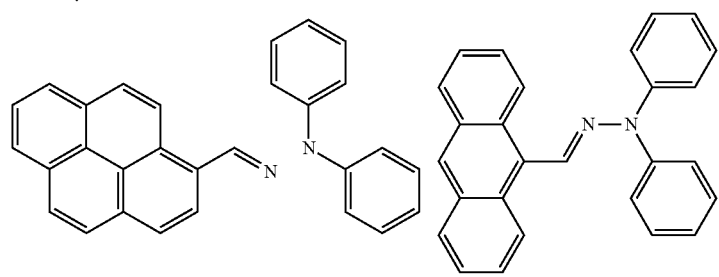

[Chem 15]
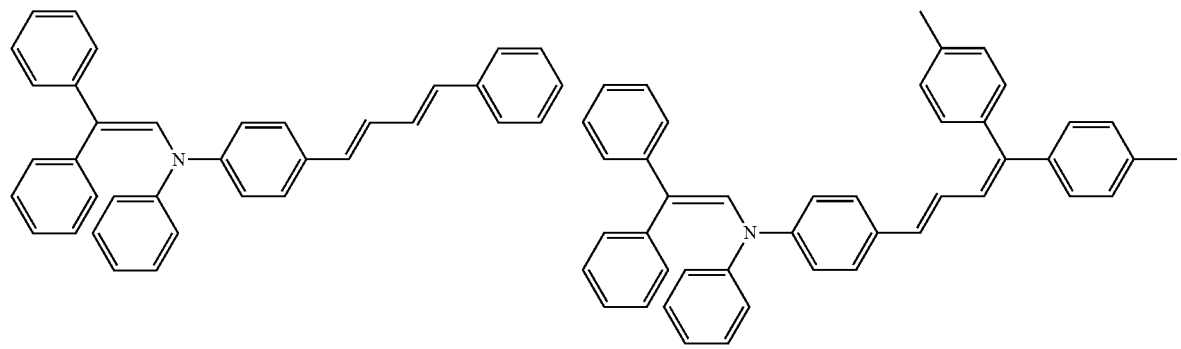
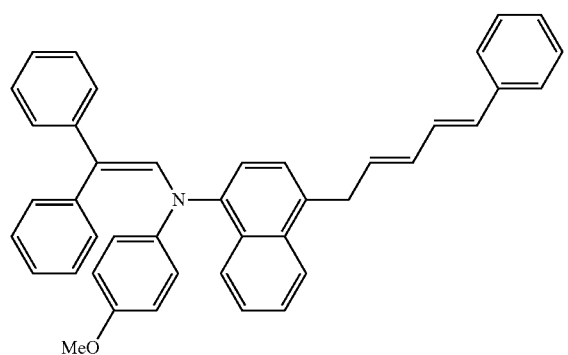
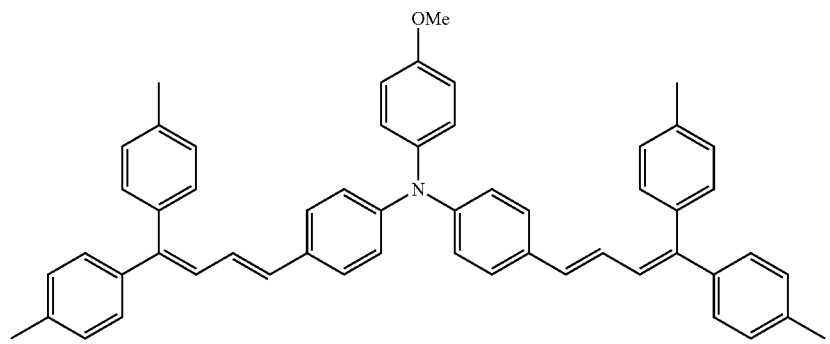
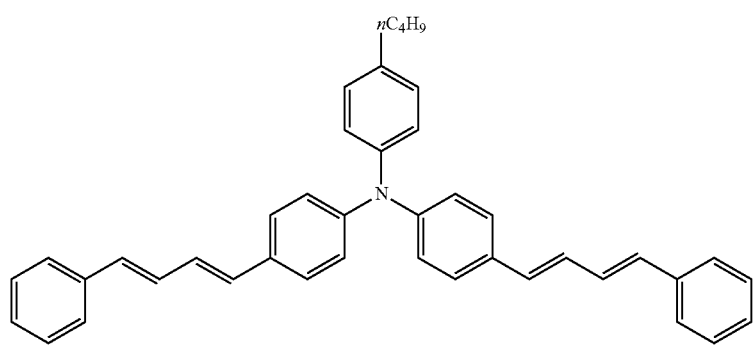

-continued
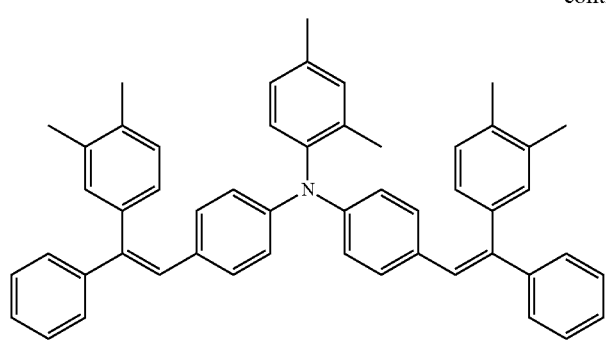
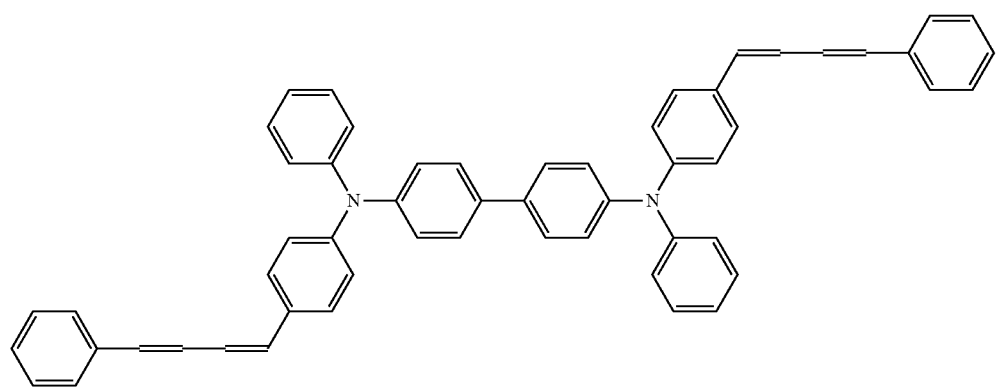
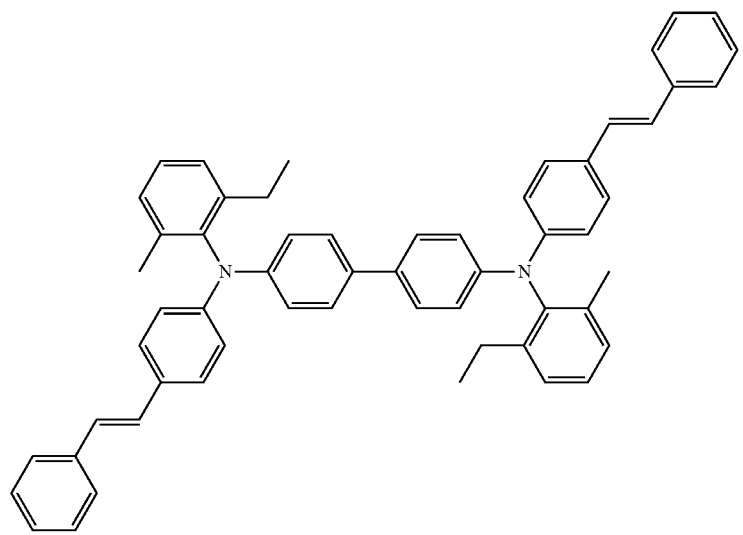

-continued
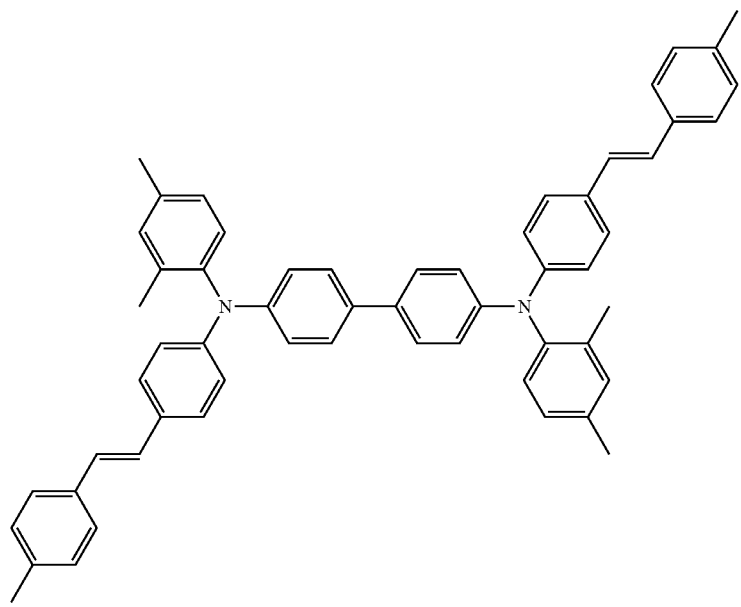
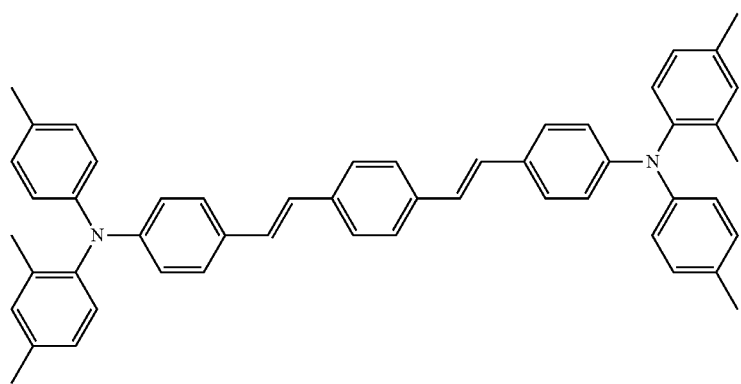
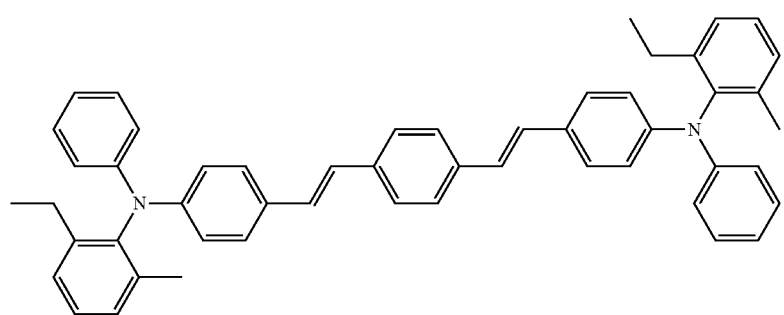
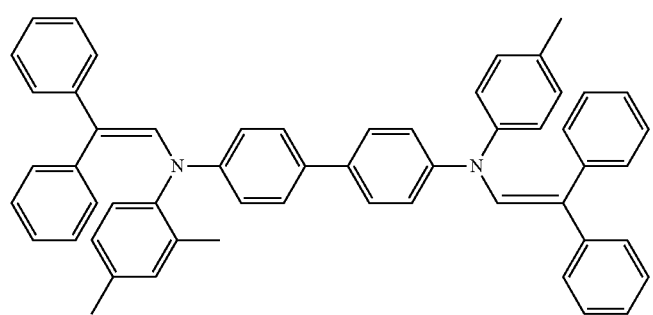

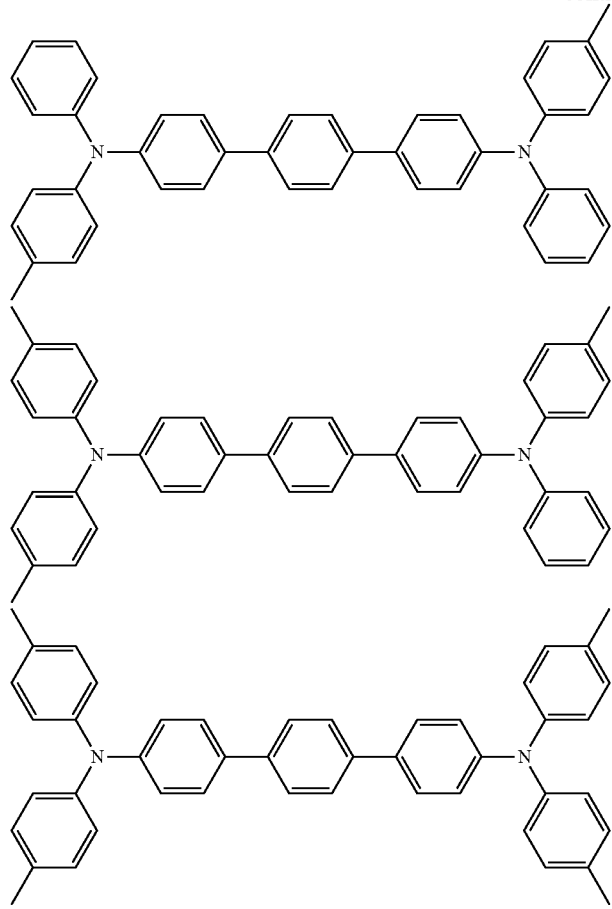

In order to enable the charge transport substance of the invention to exhibit the effects thereof, the lower limit of the ratio of the charge transport substance represented by formula (1) of the invention to all charge transport substances is usually 10% by mass or more, preferably 30% by mass or more in view of the optical attenuation characteristics of the electrophotographic photoreceptor, more preferably 50% by mass or more in view of the high-speed response of the electrophotographic photoreceptor, and especially preferably 70% by mass or more. The upper limit is usually 100% by mass or less, preferably 90% by mass or less in view of solubility, preferably 85% by mass or less in view of printing durability, and preferably 100% by mass in view of filming and abrasion resistance.

As the binder resin, there may be suitably used butadiene resins, styrene resins, vinyl acetate resins, vinyl chloride resins, acrylic ester resins, methacrylic ester resins, vinyl alcohol resins, polymers and copolymers of vinyl compounds, e.g., ethyl vinyl ether, polyvinyl butyral resins, polyvinyl formal resins, partly modified polyvinyl acetals, polyamide resins, polyurethane resins, cellulose ester resins, phenoxy resins, silicone resins, silicone-alkyd resins, poly-N-vinylcarbazole resins, polycarbonate resins, and polyester resins. Of these, polycarbonate resins and polyester resins are preferable from the viewpoint of the electrical properties. Of the polyester resins, a polyarylate resin that is a designation for a wholly aromatic polyester resin can increase an elastic deformation ratio, so that it is preferable from the viewpoint of the mechanical properties such as abrasion resistance, scratch resistance, and filming resistance. That is, it is preferred that the photosensitive layer of the invention contains at least one of a polyarylate resin and a polycarbonate resin.

In general, although the polyester resin is superior to polycarbonate resin from the viewpoint of mechanical physical properties, the polyester resin is inferior to the polycarbonate resin in view of the electrical properties and the light-induced fatigue. It is considered that this is attributable to the greater polarity of the ester bond than that of the carbonate bond and the strong acceptor character.

First, the polyester resin will be explained. In general, the polyester resin is obtained by polycondensation (condensation polymerization) of a polyhydric alcohol component and a polybasic carboxylic acid component such as a carboxylic acid, carboxylic acid anhydride, or a carboxylic acid ester as raw material monomers.

As the polyhydric alcohol component, there may be mentioned alkylene (2 to 3 carbon atoms) oxide adducts (1 to 10 average addition moles) of bisphenol A, such as polyoxypropylene(2.2)-2,2-bis(4-hydroxyphenyl)propane and polyoxyethylene(2.2)-2,2-bis(4-hydroxyphenyl)propane, ethylene glycol, propylene glycol, neopentyl glycol, glycerol, pentaerythritol, trimethylolpropane, hydrogenated bisphenol A, sorbitol, or alkylene (2 to 3 carbon atoms) oxide adducts (1 to 10 average addition moles) thereof, aromatic bisphenols, and the like. Those containing one or more thereof are preferred.

Moreover, as the polybasic carboxylic acid component, dicarboxylic acids such as phthalic acid, isophthalic acid, terephthalic acid, fumaric acid, maleic acid, biphenyldicarboxylic acid, and diphenyl-ether-dicarboxylic acid; succinic acids substituted with an alkyl group having 1 to 20 carbon atoms or an alkenyl group having 2 to 20 carbon atoms, such as dodecenylsuccinic acid and octylsuccinic acid; trimellitic acid, pyromellitic acid, anhydrides of these acids, and alkyl (1 to 3 carbon atoms) esters of these acids. Those containing one or more thereof are preferable.

Of these polyester resins, preferred is a wholly aromatic polyester resin (polyarylate resin) having a structural unit represented by the following formula (α).

[Chem 16]

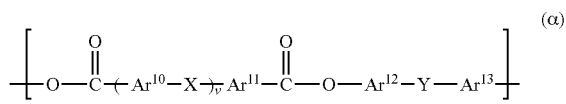

(α)

wherein $Ar^{10}$ to $Ar^{13}$ each independently represent an arylene group which may have a substituent, X represents a single bond, an oxygen atom, a sulfur atom, or an alkylene group; v represents an integer of 0 or more and 2 or less; and Y represents a single bond, an oxygen atom, a sulfur atom, or an alkylene group.

In the above formula (α), $Ar^{10}$ to $Ar^{13}$ each independently represent an arylene group which may have a substituent. The number of carbon atoms possessed by the arylene group is usually 6 or more, preferably 7 or more and usually 20 or less, preferably 10 or less, more preferably 8 or less. In the case where the number of carbon atoms is too large, there is a possibility that the production cost increases and the electrical properties also deteriorate.

Specific examples of $Ar^{10}$ to $Ar^{13}$ include a 1,2-phenylene group, a 1,3-phenylene group, a 1,4-phenylene group, a naphthylene group, an anthrylene group, a phenanthrylene group, and the like. Of these, from the viewpoint of electrical properties, a 1,4-phenylene group is preferable. One arylene group may be used alone or two or more thereof may be used in arbitrary ratio and combination.

Moreover, as the substituent group which $Ar^{10}$ to $Ar^{13}$ may have, an alkyl group, an aryl group, a halogen group, an alkoxy group, and the like may be mentioned. Of these, when considering the mechanical properties as the binder resin for the photosensitive layer and the solubility in the coating fluid for photosensitive layer formation, a methyl group, an ethyl group, a propyl group, or an isopropyl group is preferable as the alkyl group; a phenyl group or a naphthyl group is preferable as the aryl group; a fluorine atom, a chlorine atom, a bromine atom, or an iodine atom is preferable as the halogen group; and a methoxy group, an ethoxy group, a propoxy group, or a butoxy group is preferable as the alkoxy group.

In the case where the substituent is an alkyl group, the number of carbon atoms of the alkyl group is usually 1 or more and usually 10 or less, preferably 8 or less, and more preferably 2 or less.

More specifically, $Ar^{12}$ and $Ar^{13}$ each independently preferably have the number of substituents of 0 or more and 2 or less, and more preferably have a substituent from the viewpoint of adhesion. Especially, the number of substituents is particularly preferably 1 from the viewpoint of abrasion resistance. Furthermore, an alkyl group is preferable as the substituent and a methyl group is particularly preferable.

On the other hand, $Ar^{10}$ and $Ar^{11}$ each independently preferably have the number of substituents of 0 or more and 2 or less and more preferably does not have a substituent from the viewpoint of abrasion resistance.

Moreover, in the above formula (α), Y is a single bond, an oxygen atom, a sulfur atom, or an alkylene group. The alkylene group is preferably $-CH_2-$, $-CH(CH_3)-$, $-C(CH_3)_2-$, or cyclohexylene, and particularly preferably $-CH_2-$ or $-CH(CH_3)_2-$.

In the above formula (α), X is a single bond, an oxygen atom, a sulfur atom, or an alkylene group. Of these, X is preferably an oxygen atom. On that occasion, v is preferably 0 or 1 and particularly preferably 1.

Specific examples of the dicarboxylic acid residue in the case where v is 1 include diphenyl ether-2,2'-dicarboxylic acid residue, diphenyl ether-2,3'-dicarboxylic acid residue, diphenyl ether-2,4'-dicarboxylic acid residue, diphenyl ether-3,3'-dicarboxylic acid residue, diphenyl ether-3,4'-dicarboxylic acid residue, diphenyl ether-4,4'-dicarboxylic acid residue, and the like. Of these, in view of convenience of manufacturing the dicarboxylic acid component, diphenyl ether-2,2'-dicarboxylic acid residue, diphenyl ether-2,4'-dicarboxylic acid residue, and diphenyl ether-4,4'-dicarboxylic acid residue are more preferable, and diphenyl ether-4,4'-dicarboxylic acid residue is particularly preferable.

Specific examples of the dicarboxylic acid residue in the case where v is 0 include phthalic acid residue, isophthalic acid residue, terephthalic acid residue, toluene-2,5-dicarboxylic acid residue, p-xylene-2,5-dicarboxylic acid residue, naphthalene-1,4-dicarboxylic acid residue, naphthalene-2,3-dicarboxylic acid residue, naphthalene-2,6-dicarboxylic acid residue, biphenyl-2,2'-dicarboxylic acid residue, and biphenyl-4,4'-dicarboxylic acid residue. Preferred are phthalic acid residue, isophthalic acid residue, terephthalic acid residue, naphthalene-1,4-dicarboxylic acid residue, naphthalene-2,6-dicarboxylic acid residue, biphenyl-2,2'-dicarboxylic acid residue, and biphenyl-4,4'-dicarboxylic acid residue, and particularly preferred are isophthalic acid residue and terephthalic acid residues. It is also possible to use a plurality of these dicarboxylic acid residues in combination.

The following will show specific examples of suitable structures of the binder resin described above. These specific examples are those given by way of illustration, and it is possible to use any known binder resins unless they are contrary to the spirit of the invention.

[Chem 17]

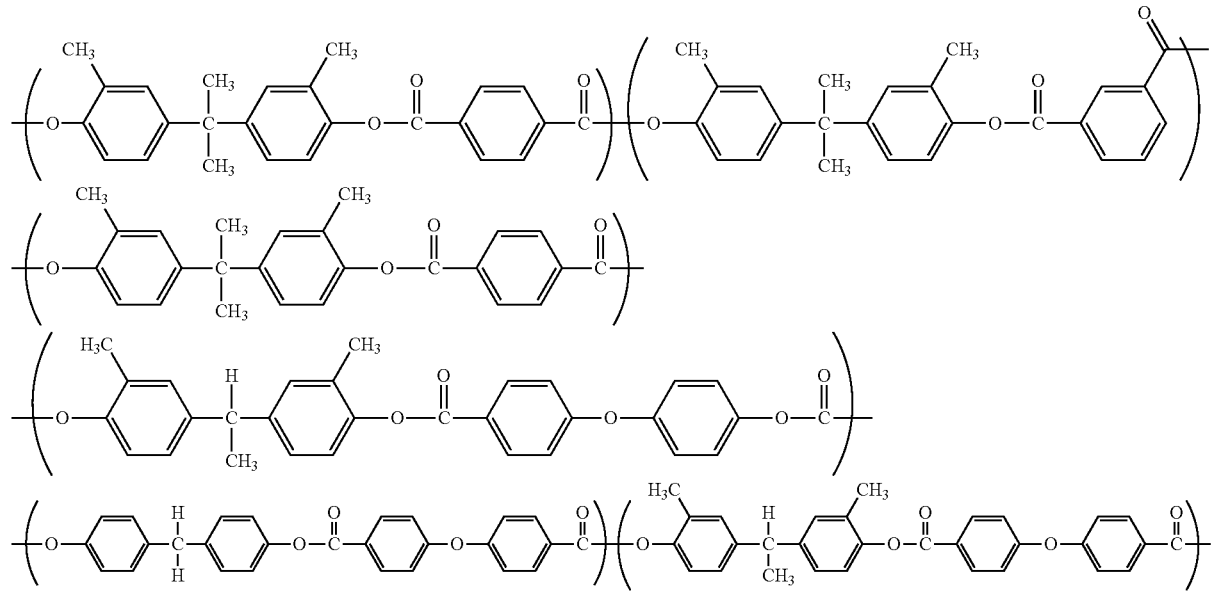

Then, the polycarbonate resin will be explained. In general, as the polycarbonate resin, one manufactured by a solvent process, such as an interfacial process (interfacial polycondensation) or a solution method in which a bisphenol and phosgene are reacted in a solution or a melting method in which a bisphenol and a carbonic acid diester are subjected to a polycondensation reaction through an ester exchange reaction is widely used as an inexpensive manufacturing method. As the bisphenol, the following compounds are preferably used. Incidentally, as the polycarbonate resin, not only a homopolymer consisting of one kind of bisphenol but also a copolymer manufactured by copolymerizing two or more kinds of bisphenols may be used.

[Chem 18]

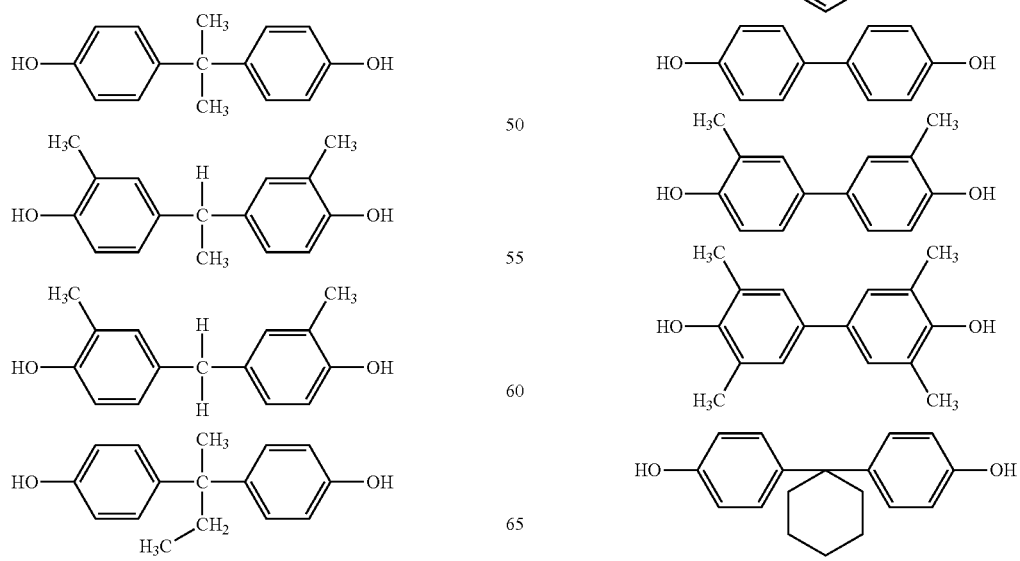

-continued
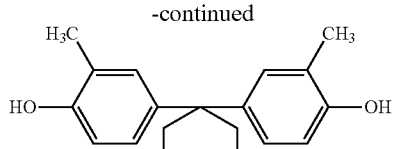
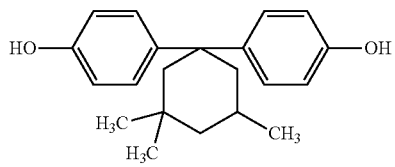
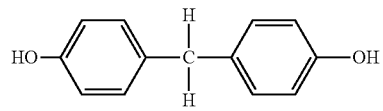
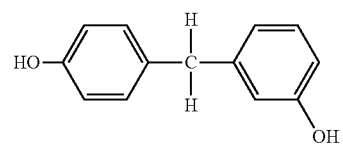
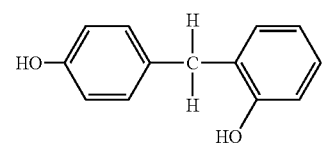
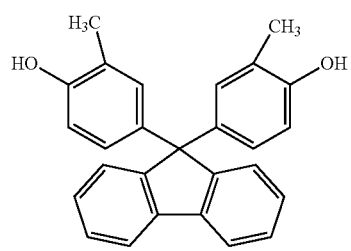
-continued
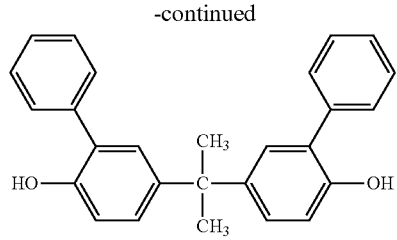
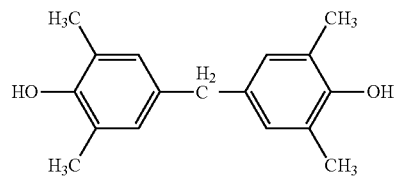
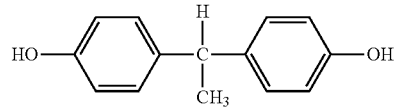
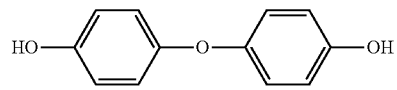
Of those described above, preferred is a polycarbonate resin having a structural unit represented by the following formula (β).
[Chem 19]
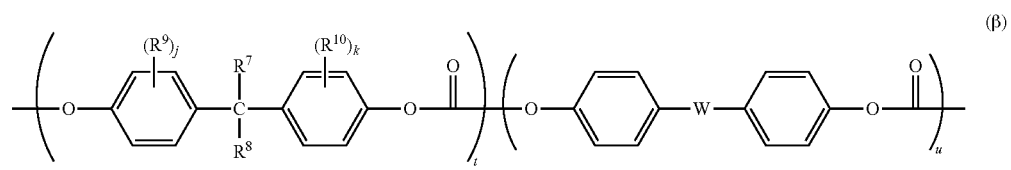

wherein $R^7$ and $R^8$ each independently represent a hydrogen atom, an aryl group, or an alkyl group having 1 to 10 carbon atoms and the $R^7$ and $R^8$ groups may be combined to form a ring; $R^9$ and $R^{10}$ each independently represents a hydrogen atom or an alkyl group having 1 to 10 carbon atoms and j and k each independently represent an integer of 0 to 4; W represents a single bond, an oxygen atom, or $—CR^{11}R^{12}—$ and the $R^{11}$ and $R^{12}$ groups each independently represent a hydrogen atom, an alkyl group having 1 to 10 carbon atoms, or a phenyl group; t and u each independently represent a numeral of 0 to 100; provided that the units represented by t and u have different structures and there is no case of t=u=0.

In the case where $R^7$ to $R^{12}$ are an alkyl group having 1 to 10 carbon atoms, the carbon number of the alkyl group is preferably 8 or less, more preferably 6 or less, and particularly preferably 3 or less. As the alkyl group, there may be specifically mentioned linear alkyl groups such as a methyl group, an ethyl group, and a propyl group; branched alkyl groups such as an isopropyl group, a tert-butyl group, and an isobutyl group; cyclic alkyl groups such as a cyclohexyl group and a cyclopentyl group. Of these, from the viewpoint of easiness of synthesis, a methyl group is particularly preferable. Furthermore, the substituents may be combined with each other to form a ring.

In the case where $R^7$ and $R^8$ are an aryl group, the number of carbon atoms of the aryl group is usually 30 or less, preferably 20 or less, and more preferably 15 or less. Specifically, a phenyl group, a naphthyl group, an anthranyl group, a pyrenyl group, and the like may be mentioned. From the viewpoint of easiness of synthesis, a phenyl group or a naphthyl group is preferable and a naphthyl group is particularly preferable from the viewpoint of crack resistance. A phenyl group is particularly preferable from the viewpoint of easiness of manufacture.

The following will show specific examples of preferred structures of the binder resin. These specific examples are those given by way of illustration and it is possible to use any known binder resins unless they are contrary to the spirit of the invention.

[Chem 20]

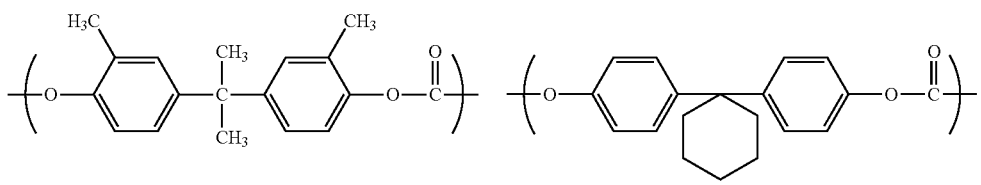

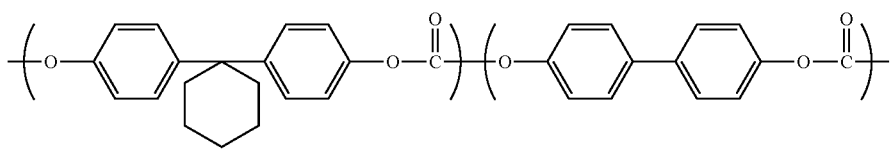

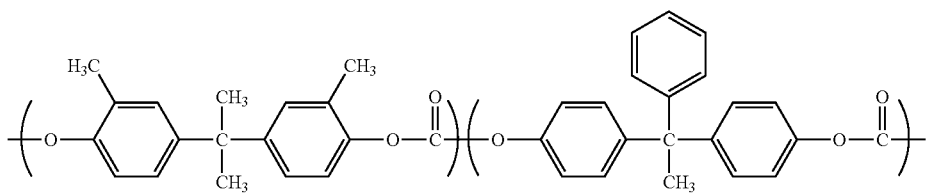

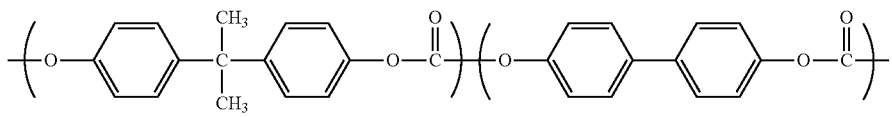

The viscosity-average molecular weight of the binder resin to be used in the invention is not limited unless it significantly impairs the effects of the invention but is preferably 10,000 or more, more preferably 20,000 or more and, from the viewpoint of printing durability, is further preferably 50,000 or more. Moreover, the upper limit is preferably 150,000 or less, more preferably 120,000 or less, and, from the viewpoint of coating ability, it is desirable that the molecular weight is further preferably 100,000 or less. In the case of using the charge transport substance of the invention, even when a resin having such a high average molecular weight as 70,000 or more, the resin is easily dispersed and high electrical properties are obtained.

In addition to the above polyester resin and polycarbonate resin, the other binder resin as described above may be used in combination in the range where the effects of the invention are not impaired.

With respect to the ratio of the binder resin to the charge transport substance, the charge transport substance may be used in a proportion of usually 10 parts by mass or more per 100 parts by mass of the binder resin. In particular, the proportion is preferably 20 parts by mass or more from the viewpoint of reducing the residual potential, and is more preferably 30 parts by mass or more from the viewpoints of stability and charge mobility during repeated use. On the other hand, from the viewpoint of the thermal stability of the photosensitive layer, the charge transport substance is used in a proportion of usually 120 parts by mass or less. In particular, the proportion is preferably 100 parts by mass or less from the viewpoint of compatibility between the charge transport substance and the binder resin, more preferably 80 parts by mass or less from the viewpoint of printing durability, and most preferably 60 parts by mass or less from the viewpoint of scratch resistance.

The thickness of the charge transport layer is not particularly limited. However, from the viewpoints of long life and image stability and further from the viewpoint of charging stability, the thickness is usually 5 μm or more, preferably 10 μm or more, but is usually 50 μm or less, preferably 45 μm or less, more preferably 40 μm or less. From the viewpoint of achieving high resolution, the thickness is particularly preferably 35 μm or less.

<Single-Layer Type Photosensitive Layer>

The single-layer type photosensitive layer is formed using a binder resin in order to ensure film strength, in addition to a charge generation substance and a charge transport substance, in the same manner as in the charge transport layer of the multilayer type photoreceptor. Specifically, the single-layer type photosensitive layer can be obtained by dissolving or dispersing a charge generation substance, a charge transport substance, and any of various binder resins in a solvent to produce a coating fluid, applying the coating fluid on a electroconductive support (or on an undercoat layer when the undercoat layer has been disposed), and drying the coating fluid applied.

The kinds of the charge transport substance and binder resin and the proportion of these ingredients to be used are the same as explained above with regard to the charge transport layer of the multilayer type photoreceptor. A charge generation material is further dispersed in a charge transport medium including the charge transport substance and the binder resin.

As the charge generation material, the same charge generation materials as those explained above with regard to the charge generation layer of the multilayer type photoreceptor can be used. In the case of the photosensitive layer of the single-layer type photoreceptor, however, it is necessary to regulate the charge generation material so as to have a sufficiently reduced particle diameter. Specifically, the particle diameter is regulated to the range of usually 1 μm or less, preferably 0.5 μm or less.

With respect to the proportion of the binder resin and charge generation material used in the single-layer type photosensitive layer, the proportion of the charge generation material per 100 parts by mass of the binder resin is usually 0.1 part by mass or more, preferably 1 part by mass or more, and is usually 30 parts by mass or less, preferably 10 parts by mass or less.

The thickness of the single-layer type photosensitive layer is usually 5 μM or more, preferably 10 μm or more, and is usually 100 μm or less, preferably 50 μm or less.

<Other Functional Layers>

Known additives, e.g., an antioxidant, a plasticizer, an ultraviolet absorber, an electron-attracting compound, a leveling agent, and a visible-light-shielding agent, may be incorporated into the photosensitive layer of each of the multilayer type photoreceptor and the single-layer type photoreceptor or into the layers constituting the photosensitive layer, for the purpose of improving film-forming properties, flexibility, applicability, non-fouling properties, gas resistance, light resistance, etc.

In either the multilayer type photoreceptor or the single-layer type photoreceptor, the photosensitive layer formed in the manner described above may be the uppermost layer, i.e., the surface layer thereof. It is, however, possible to further dispose another layer thereon as a surface layer. For example, a protective layer may be disposed for the purpose of preventing the photosensitive layer from being damaged or wearing or of preventing or lessening the deterioration of the photosensitive layer caused by, for example, discharge products generated from the charging device, etc.

The protective layer has an electrical resistance usually in the range of $10^9$ Ω·cm or more and $10^{14}$ Ω·cm or less. When the electrical resistance thereof is higher than the range, the photoreceptor has an elevated residual potential to give fogged images. On the other hand, when the electrical resistance thereof is lower than the range, there is a possibility of resulting in image blurring and a decrease in resolution. The protective layer must be configured so that this layer does not substantially prevent the light irradiated for image-wise exposure from passing therethrough.

A fluororesin, a silicone resin, a polyethylene resin, particles of any of these resins, particles of an inorganic compound such as silica or alumina, or the like may be incorporated into the surface layer for the purposes of reducing the frictional resistance and wear of the photoreceptor surface, heightening the efficiency of toner transfer from the photoreceptor to a transfer belt and to paper, etc. Alternatively, a layer containing any of these resins or such particles may be newly formed as a surface layer.

<Method for Forming Each Layer>

The layers constituting the photoreceptor are formed by repeating the following application/drying steps for each layer, the steps comprising dissolving or dispersing the materials to be incorporated in a solvent to obtain a coating fluid, successively applying the coating fluid on a electroconductive support by a known technique, such as dip coating, spray coating, nozzle coating, bar coating, roll coating, or blade coating, and drying.

The solvent or dispersion medium to be used for producing the coating fluids is not particularly limited. However, specific examples thereof include alcohols such as methanol, ethanol, propanol, and 2-methoxyethanol; ethers such as tetrahydrofuran, 1,4-dioxane, and dimethoxyethane; esters such as methyl formate and ethyl acetate; ketones such as acetone, methyl ethyl ketone, cyclohexanone, and 4-methoxy-4-methyl-2-pentanone; aromatic hydrocarbons such as benzene, toluene, and xylene; chlorinated hydrocarbons such as dichloromethane, chloroform, 1,2-dichloroethane, 1,1,2-trichloroethane, 1,1,1-trichloroethane, tetrachloroethane, 1,2-dichloropropane, and trichloroethylene; nitrogen-containing compounds such as n-butylamine, isopropanolamine, diethylamine, triethanolamine, ethylenediamine, and triethylenediamine; aprotic polar solvents such as acetonitrile, N-methylpyrrolidone, N,N-dimethylformamide, and dimethyl sulfoxide; and the like. One of these compounds may be used alone, or two or more compounds of any desired combination and any desired kinds may be used in combination.

The amount of the solvent or dispersion medium to be used is not particularly limited. It is, however, preferable to suitably regulate the amount thereof so that the physical properties of the coating fluid, such as solid concentration and viscosity, fall within desired ranges, while taking account of the purpose of each layer and the nature of the selected solvent or dispersion medium.

For example, in the case of the single-layer type photoreceptor and of the charge transport layer of the function-separated type photoreceptor, the solid concentration of each coating fluid is usually 5% by mass or more, preferably 10% by mass or more, and is usually 40% by mass or less, preferably 35% by mass or less.

Furthermore, the viscosity of the coating fluid, as measured at the temperature at which the coating fluid is used, is usually 10 mPa·s or more, preferably 50 mPa·s or more, and is usually 500 mPa·s or less, preferably 400 mPa·s or less.

In the case of the charge generation layer of the multilayer type photoreceptor, the solid concentration of the coating fluid is usually 0.1% by mass or more, preferably 1% by mass or more, and is usually 15% by mass or less, preferably 10% by mass or less.

The viscosity of the coating fluid, as measured at the temperature at which the coating fluid is used, is usually 0.01 mPa·s or more, preferably 0.1 mPa·s or more, and is usually 20 mPa·s or less, preferably 10 mPa·s or less.

As methods for applying the coating fluids, there may be mentioned a dip coating method, a spray coating method, a spinner coating method, a bead coating, a wire bar coating method, a blade coating method, a roller coating method, an air-knife coating method, and a curtain coating method. It is also possible to use other known coating methods.

For drying each coating fluid, the coating fluid is dried at room temperature until the coating film becomes dry to the touch, and is thereafter dried with heating at a temperature range of 30° C. or higher and 200° C. or lower for a period of 1 minute to 2 hours, stationarily or with air blowing. The heating temperature may be constant, or the heating may be conducted while changing the temperature during drying.

<<Image-Forming Apparatus>>

Next, embodiments of the image-forming apparatus (image-forming apparatus of the invention) which employs the electrophotographic photoreceptor of the invention are explained with reference to FIG. 1, which illustrates the configuration of important parts of the apparatus. It is, however, noted that the embodiments are not limited to the following explanations and can be arbitrarily modified unless the modifications depart from the spirit of the invention.

As shown in FIG. 1, the image-forming apparatus is configured so as to be equipped with an electrophotographic photoreceptor 1, a charging device 2, an exposure device 3, and a developing device 4. The apparatus is further equipped with a transfer device 5, a cleaner 6, and a fixing device 7 according to need.

The electrophotographic photoreceptor 1 is not particularly limited so long as it is the electrophotographic photoreceptor of the invention described above. FIG. 1 shows, as an example thereof, a drum-shaped photoreceptor obtained by forming the aforementioned photosensitive layer on the surface of a cylindrical electroconductive support. The charging device 2, exposure device 3, developing device 4, transfer device 5, and cleaner 6 have been disposed along the peripheral surface of this electrophotographic photoreceptor 1.

The charging device 2 serves to charge the electrophotographic photoreceptor 1. This device evenly charges the surface of the electrophotographic photoreceptor 1 to a given potential. As the charging device, there are frequently used a corona charging device, such as a corotron or a scorotron, a direct charging device in which a direct charging member to which a voltage is being applied is brought into contact with the photoreceptor surface to charge the surface (contact type charging device), and the like. Examples of the direct charging device include charging rollers, charging brushes, and the like. FIG. 1 shows a roller type charging device (charging roller) as an example of the charging device 2. As a means for the direct charging, it is possible to perform either charging which involves aerial discharge or injection charging which does not involve aerial discharge. As the voltage to be applied for the charging, a direct-current voltage alone can be used or an alternating current superimposed on a direct current is also usable.

The exposure device 3 is not particularly limited in the kind thereof so long as the device can illuminate the electrophotographic photoreceptor 1 and thereby form an electrostatic latent image on the photosensitive surface of the electrophotographic photoreceptor 1. Specific examples thereof include halogen lamps, fluorescent lamps, lasers such as semiconductor lasers and He—Ne lasers, LEDs, and the like. It is also possible to conduct exposure by the technique of internal photoreceptor exposure. Any desired light may be used for exposure. For example, monochromatic light having a wavelength of 780 nm, monochromatic light having a slightly short wavelength of 600 nm to 700 nm, monochromatic light having a short wavelength of 380 nm to 500 nm, or the like may be used to conduct exposure.

The developing device 4 is not particularly limited in the kind thereof, and any desired device can be used, for example, a device operated by a dry development technique such as cascade development, development with one-component insulating toner, development with one-component conductive toner, or two-component magnetic-brush development, or by a wet development technique or the like. In FIG. 1, the developing device 4 includes a developing vessel 41, agitators 42, a feed roller 43, a developing roller 44, and a control member 45. This device has been configured so that a toner T is stored in the developing vessel 41. According to need, the developing device 4 may be equipped with a replenishing device (not shown) for replenishing the toner T. This replenishing device is configured so that the toner T can be replenished from a container, e.g., a bottle or a cartridge.

The feed roller 43 is made of a conductive sponge or the like. The developing roller 44 is composed of, for example, a metallic roll made of iron, stainless steel, aluminum, nickel, or the like or a resinous roll obtained by coating such a metallic roll with a silicone resin, urethane resin, fluororesin, or the like. The surface of this developing roller 44 may be subjected to surface-smoothing processing or surface-roughening processing according to need.

The developing roller 44 is disposed between the electrophotographic photoreceptor 1 and the feed roller 43, and is in contact with both the electrophotographic photoreceptor 1 and the feed roller 43.

The feed roller 43 and the developing roller 44 are rotated by a rotation driving mechanism (not shown). The feed roller 43 holds the toner T stored and supplies the toner T to the developing roller 44. The developing roller 44 holds the toner T supplied by the feed roller 43 and brings the toner T into contact with the surface of the electrophotographic photoreceptor 1.

The control member 45 is formed from a resinous blade made of a silicone resin, a urethane resin, or the like, a metallic blade made of stainless steel, aluminum, copper, brass, phosphor bronze, or the like, a blade obtained by coating such the metallic blade with a resin, or the like. This control member 45 is in contact with the developing roller 44, and is pushed against the developing roller 44 with springs or the like at a given force (the linear blade pressure is generally 5 to 500 g/cm). According to need, this control member 45 may be made to have the function of charging the toner T based on electrification caused by friction with the toner T.

The agitators 42 are each rotated by the rotation driving mechanism. The agitators 42 agitate the toner T and also convey the toner T to the feed roller 43 side. A plurality of agitators 42 differing in blade shape, size, etc. may be disposed.

The kind of the toner T is not limited, and a chemical toner or the like obtained by suspension polymerization, emulsion polymerization, or the like can be used besides a pulverized toner. Especially, when a chemical toner is used, this toner preferably is one including toner particles having a small particle diameter of about 4 to 8 µm. The toner particles to be used can have any of various shapes ranging from a shape close to sphere to a shape which is not spherical, such as a potato shape. A chemical toner is excellent in terms of evenness of charging and transferability and are suitably used for image quality improvement.

The transfer device 5 is not particularly limited in the kind thereof, and there can be used a device operated by any desired technique, for example, an electrostatic transfer technique, a pressure transfer technique, an adhesive transfer technique, and the like, such as corona transfer, roller transfer, and belt transfer. Here, the transfer device 5 is a device composed of a transfer charger, a transfer roller, a transfer belt, and the like disposed so as to face the electrophotographic photoreceptor 1.

A given voltage (transfer voltage) which has the polarity opposite to that of the charge potential of the toner T is applied to the transfer device 5, and this transfer device 5 thus serves to transfer the toner image formed on the electrophotographic photoreceptor 1 to recording paper (paper or medium) P.

There are no particular limitations on the cleaner 6, and any desired cleaner can be used, such as a brush cleaner, a magnetic brush cleaner, an electrostatic brush cleaner, a magnetic roller cleaner, or a blade cleaner. The cleaner 6 serves to scrape off the residual toner adherent to the electrophotographic photoreceptor 1 with a cleaning member and thus recover the residual toner. However, when there is little or substantially no toner remaining on the surface of the photoreceptor, the cleaner 6 may be omitted.

The fixing device 7 is composed of an upper fixing member (fixing roller) 71 and a lower fixing member (fixing roller) 72. The fixing members 71 and/or 72 are equipped with a heater 73 inside. FIG. 1 shows an example in which the upper fixing member 71 is equipped with a heater 73 inside.

As each of the upper and lower fixing members 71 and 72, there can be used a known heat-fixing member such as a fixing roll obtained by coating a metallic tube made of stainless steel, aluminum, or the like with a silicone rubber, a fixing roll obtained by further coating that fixing roll with a Teflon (registered trademark) resin, or a fixing sheet. Furthermore, the fixing members 71 and 72 may be configured so that a release agent such as a silicone oil is supplied thereto in order to improve releasability, or may be configured so that the members are forcedly pressed against each other with springs or the like.

The toner which has been transferred to the recording paper P passes between the upper fixing member 71 and lower fixing member 72 heated at a given temperature, during which the toner is heated to a molten state. After the passing, the toner is cooled and fixed to the recording paper P.

The fixing device also is not particularly limited in the kind thereof. Any fixing device which is operated by any desired fixing technique, such as heated-roller fixing, flash fixing, oven fixing, or pressure fixing, can be disposed besides the fixing device used here.

In the electrophotographic apparatus having the configuration described above, image recording is conducted in the following manner. Namely, first, the surface (photosensitive surface) of the electrophotographic photoreceptor 1 is charged to a given potential (e.g., −600 V) by the charging device 2. On this occasion, the charging may be conducted with a direct-current voltage or with a direct-current voltage on which an alternating-current voltage has been superimposed.

Subsequently, the charged photosensitive surface of the photoreceptor 1 is exposed to light by the exposure device 3 according to the image to be recorded. Thus, an electrostatic latent image is formed on the photosensitive surface. This electrostatic latent image formed on the photosensitive surface of the photoreceptor 1 is developed by the developing device 4.

In the developing device 4, toner T fed by the feed roller 43 is spread into a thin layer with the control member (developing blade) 45 and, simultaneously therewith, frictionally charged so as to have given polarity (here, the toner is charged so as to have negative polarity, which is the same as the polarity of the charge potential of the photoreceptor 1). The toner T is conveyed while being held by the developing roller 44 and is brought into contact with the surface of the photoreceptor 1.

When the toner T charged based on electrification held on the developing roller 44 comes into contact with the surface of the photoreceptor 1, a toner image corresponding to the electrostatic latent image is formed on the photosensitive surface of the photoreceptor 1. This toner image is transferred to recording paper P by the transfer device 5. Thereafter, the toner which has not been transferred and remains on the photosensitive surface of the photoreceptor 1 is removed by the cleaner 6.

After the transfer of the toner image to the recording paper P, the recording paper P is passed through the fixing device 7 to thermally fix the toner image to the recording paper P. Thereby, a finished image is obtained.

Incidentally, the image-forming apparatus may be configured so that an erase step, for example, can be conducted, besides the configuration described above. The erase step is a step in which the electrophotographic photoreceptor is exposure to light to thereby remove the residual charges from the electrophotographic photoreceptor. As an eraser, a fluorescent lamp, LED, or the like may be used. The light to be used in the erase step, in many cases, is light having such an intensity that the exposure energy thereof is at least 3 times that of the exposure light.

Moreover, the configuration of the image-forming apparatus may be further modified. For example, the apparatus may be configured so that steps such as a pre-exposure step and an auxiliary charging step can be conducted therein, or may be configured so that offset printing is conducted therein. Furthermore, the apparatus may have a full-color tandem configuration in which a plurality of toners are used.

Incidentally, the electrophotographic photoreceptor 1 may be combined with at least one device selected from the charging device 2, the exposure device 3, and the developing device 4 to constitute an integrated cartridge (hereinafter suitably referred to as "electrophotographic photoreceptor cartridge"). This electrophotographic photoreceptor cartridge may have a configuration in which the cartridge is detachably mounted on the main body of an electrophotographic apparatus such as a copier or a laser beam printer. In this case, when the electrophotographic photoreceptor 1 or another member has deteriorated, this electrophotographic photoreceptor cartridge is detached from the main body of the image-forming apparatus and a fresh electrophotographic photoreceptor cartridge is mounted on the main body of the image-forming apparatus. Thereby, maintenance and management of the image-forming apparatus is facilitated.

EXAMPLES

The embodiment of the present invention will be described in greater detail below with reference to Examples. However, the following Examples are given for explaining the invention in detail, and the invention is not limited to Examples shown below but can be performed by arbitrarily making modifications therein unless they depart from the gist of the invention. In the following Examples and Comparative Examples, unless otherwise indicated, the "parts" indicates "parts by mass".

Manufacture of Charge Transport Substances Represented by Formula (1)

Manufacture Example 1

CTM1

A charge transport substance having a structural formula represented by the following formula (CTM1) was manufactured according to the following scheme A. Detailed conditions are as follows.

Scheme A

[Chem 21]

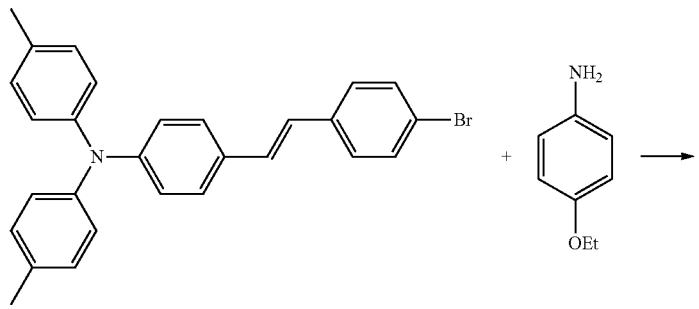

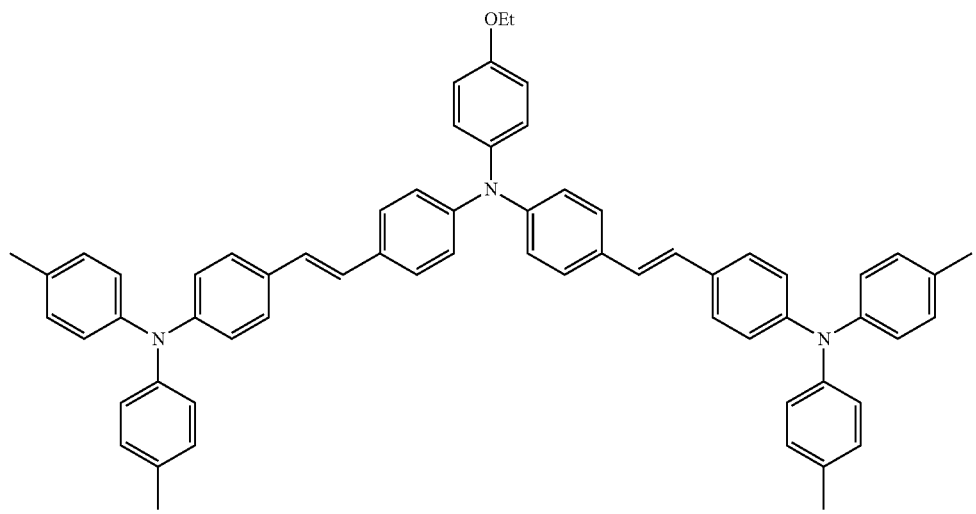

CTM 1

Compound A

Figure 3:
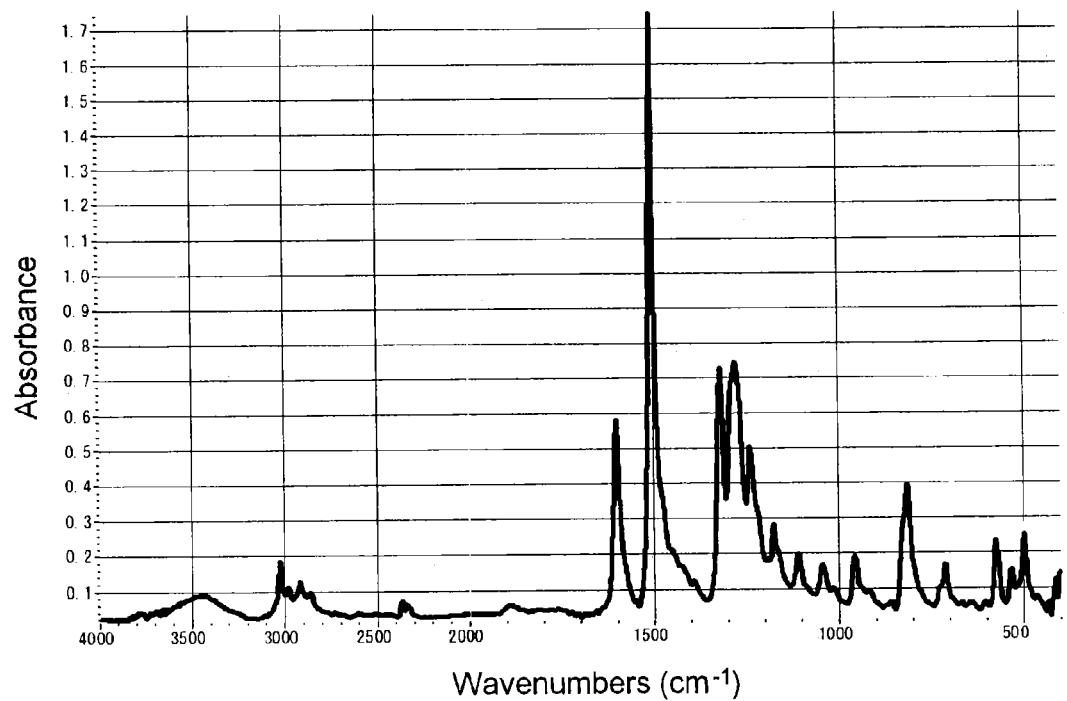
FIG. 3 is an IR chart of the charge transport substance CTM1 obtained in Manufacture Example 1.

Into 100 ml of xylene were charged 4.7 g of the compound A that is a triphenylamine derivative, 0.69 g of p-phenetidine, 2.12 g of sodium t-butoxide, 100 mg of palladium acetate, and 4 ml of a 0.6 mmol/ml toluene solution of tricyclohexylphosphine, and the temperature was elevated until reflux occur. After elevation of the temperature, the whole was stirred for 3 hours and allowed to react. After completion of the reaction, the reaction solution was cooled to room temperature and 50 ml of water was added, followed by stirring for 30 minutes. After stirring, the aqueous layer was separated, the organic layer was concentrated, and the concentration residue was purified by silica gel chromatography to give 3.2 g of the charge transport substance CTM1 as a target material (yield: 72.4%). An IR spectrum of the compound obtained is as shown in FIG. 3.

Manufacture Example 2

CTM2

Figure 4:
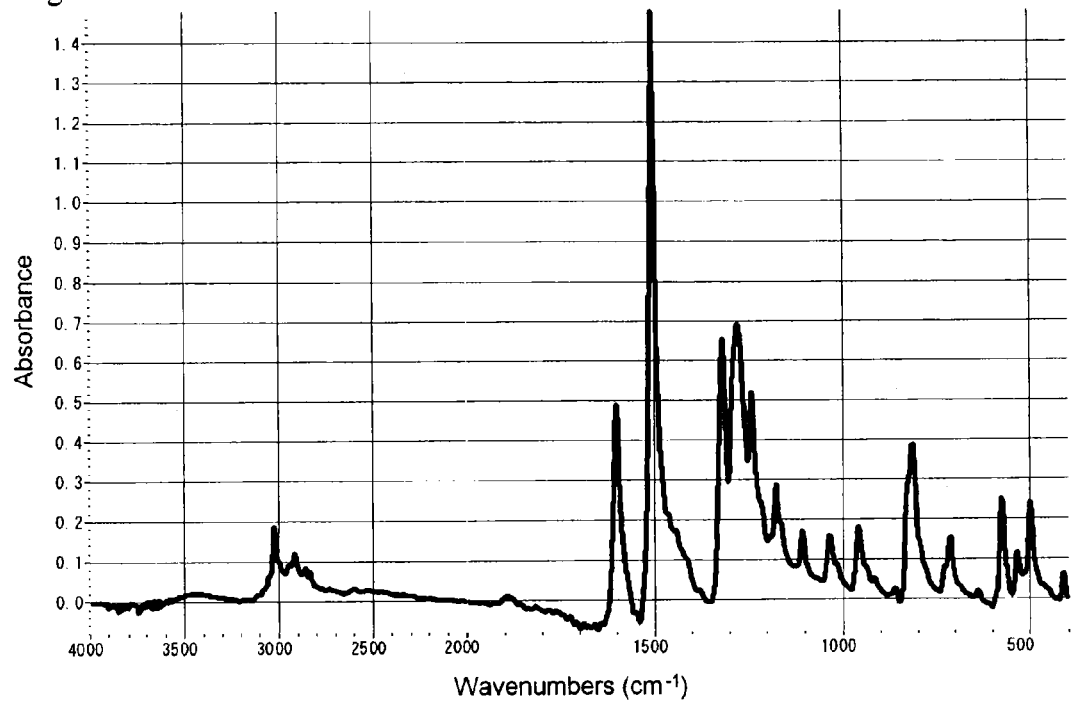
FIG. 4 is an IR chart of the charge transport substance CTM2 obtained in Manufacture Example 2.

A charge transport substance having a structure represented by the following formula (CTM2) that is a target charge transport substance was obtained in an amount of 3.4 g by performing the same operations as in Manufacture Example 1 except that p-phenetidine used in Manufacture Example 1 was changed to 0.62 g of 4-anisidine (yield: 78.2%). An IR spectrum of the compound obtained is as shown in FIG. 4.

[Chem 22]

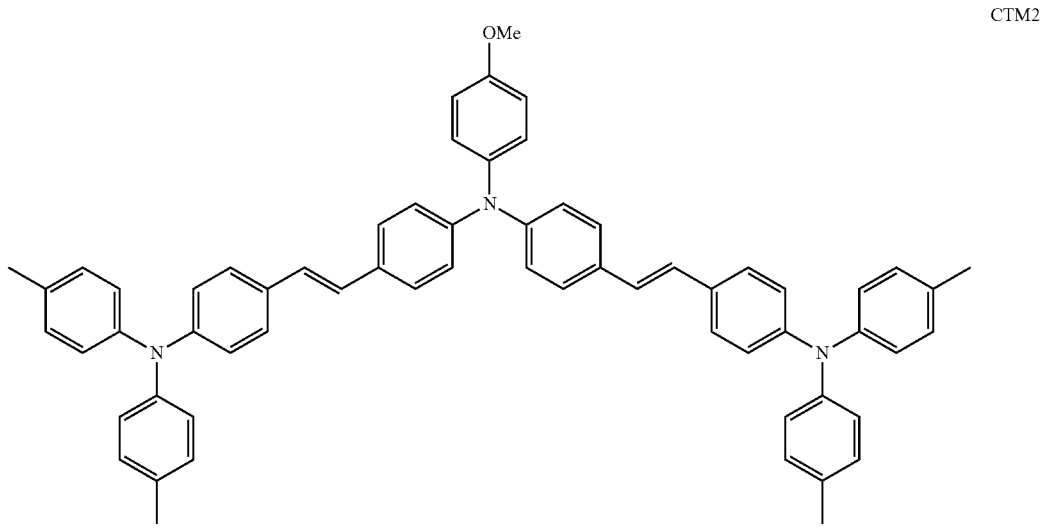

CTM2

Manufacture Example 3

CTM3

A charge transport substance having a structural formula represented by the following formula (CTM3) was manufactured according to the following scheme B. Detailed conditions are as follows.

Scheme B

[Chem 23]

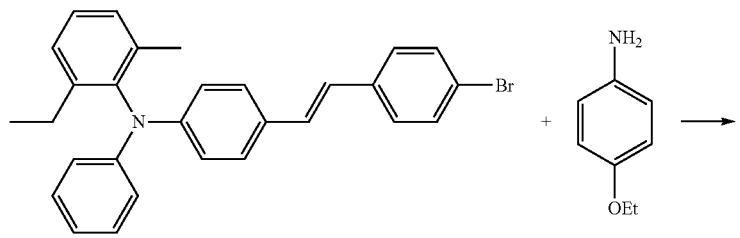

-continued

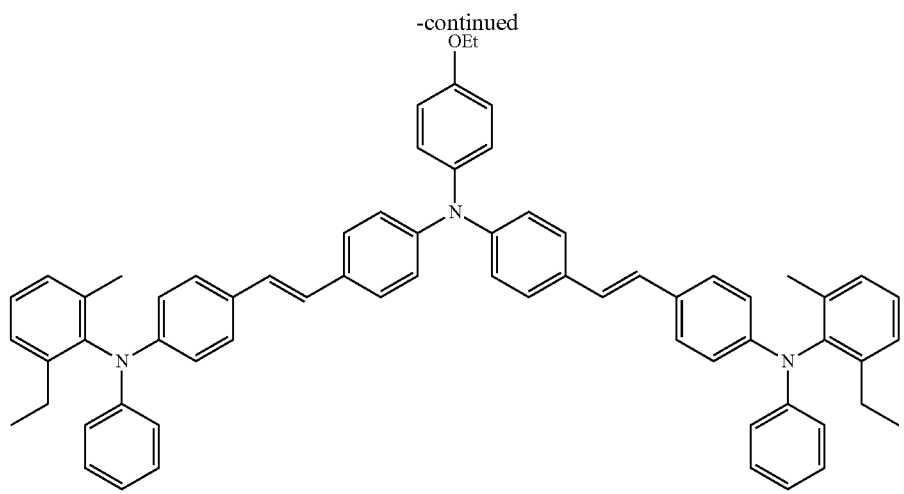

CTM 3

Compound B

Figure 5:
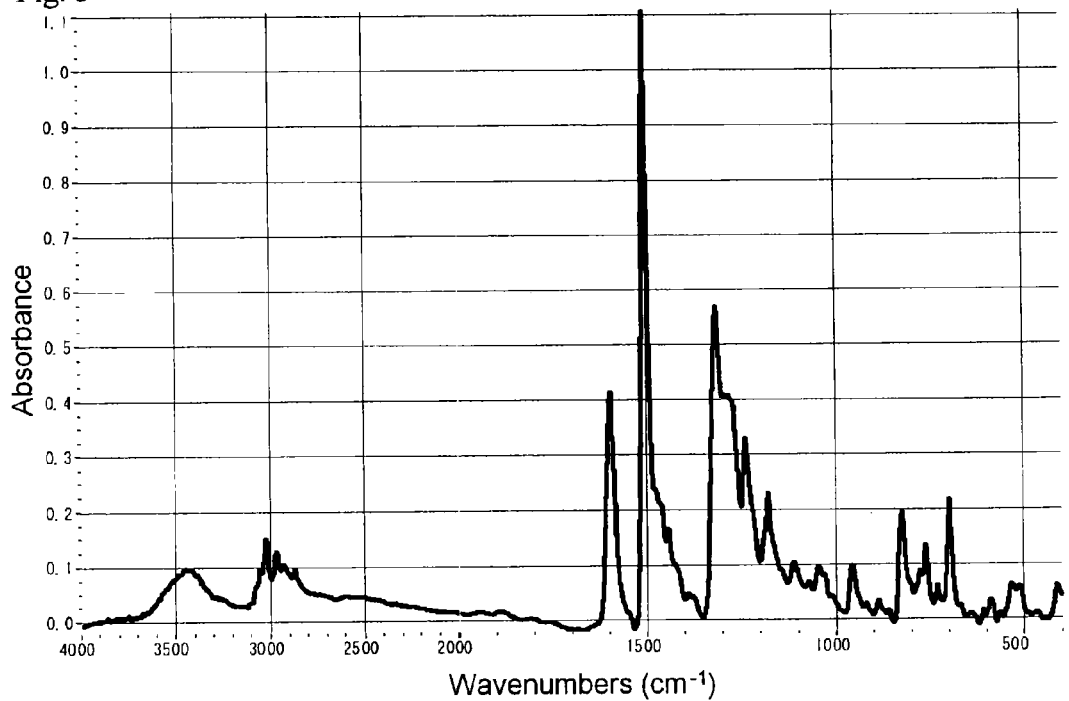
FIG. 5 is an IR chart of the charge transport substance CTM3 obtained in Manufacture Example 3.

Into 100 ml of xylene were charged 3.0 g of the compound B that is a triphenylamine derivative, 0.42 g of p-phenetidine, 1.3 g of sodium t-butoxide, 100 mg of palladium acetate, and 4 ml of a 0.6 mmol/ml toluene solution of tricyclohexylphosphine, and the temperature was elevated until reflux occur. After elevation of the temperature, the whole was stirred for 4.5 hours and allowed to react. After completion of the reaction, the reaction solution was cooled to room temperature and 25 ml of water was added, followed by stirring for 30 minutes. After stirring, the aqueous layer was separated, the organic layer was concentrated, and the concentration residue was purified by silica gel chromatography to give 1.9 g of the charge transport substance CTM3 as a target material (yield: 67.9%). An IR spectrum of the compound obtained is as shown in FIG. 5.

<Method for Producing Electrophotographic Photoreceptor>

A electroconductive support obtained by forming a vapor-deposited aluminum film (thickness: 70 μm) on a surface of a biaxially stretched polyethylene terephthalate resin film (thickness: 75 μm) was used. The following dispersion for undercoat layer formation was applied to the vapor-deposited layer of the support with a bar coater so as to be a thickness of 1.25 μM after drying, and the dispersion applied was dried to form an undercoat layer.

Rutile-form titanium oxide having an average primary-particle diameter of 40 nm ("TTO55N", manufactured by Ishihara Sanyo Kaisha, Ltd.) and 3% by mass, per 100% by mass the titanium oxide, of methyldimethoxysilane ("TSL 8117", manufactured by Toshiba Silicone Co., Ltd.) were charged into a high-speed flow type mixing kneader ("SMG 300", manufactured by KAWATA MFG Co., Ltd.). The ingredients were mixed at a high rotational peripheral speed of 34.5 m/second to obtain surface-treated titanium oxide. This surface-treated titanium oxide was dispersed in methanol/1-propanol with a ball mill to thereby form a dispersion slurry of the hydrophobized titanium oxide. The dispersion slurry and a mixed solvent of methanol/1-propanol/toluene were stirred and mixed, with heating, together with pellets of a copolyamide having a composition in which the molar ratio of ε-caprolactam represented by the following formula (A)/bis(4-amino-3-methylcyclohexyl)methane represented by the following formula (B)/hexamethylenediamine represented by the following formula (C)/decamethylenedicarboxylic acid represented by the following formula (D)/octadecamethylenedicarboxylic acid represented by the following formula (E) was 75%/9.5%/3%/9.5%/3%. After the polyamide pellets were dissolved, the mixture was subjected to an ultrasonic dispersion treatment. Thus, a dispersion for undercoat layer formation which had a mass ratio of methanol/1-propanol/toluene of 7/1/2, contained the hydrophobized titanium oxide and the copolyamide in a mass ratio of 3/1, and had a solid concentration of 18.0% was obtained.

[Chem 24]

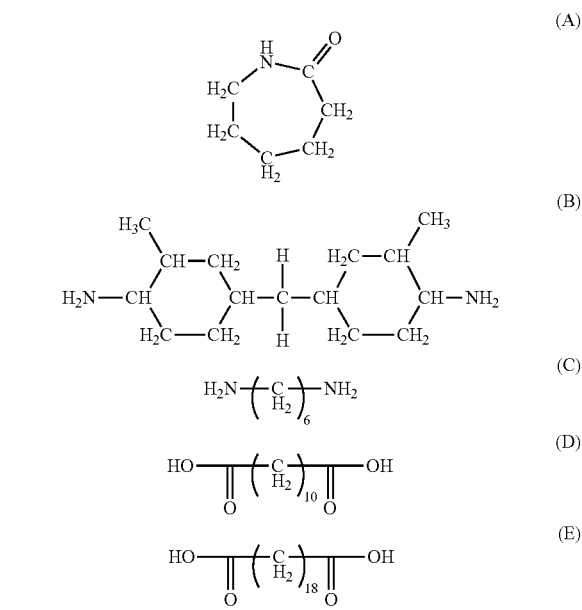

(Formation of Charge Generation Layer)

Figure 2:
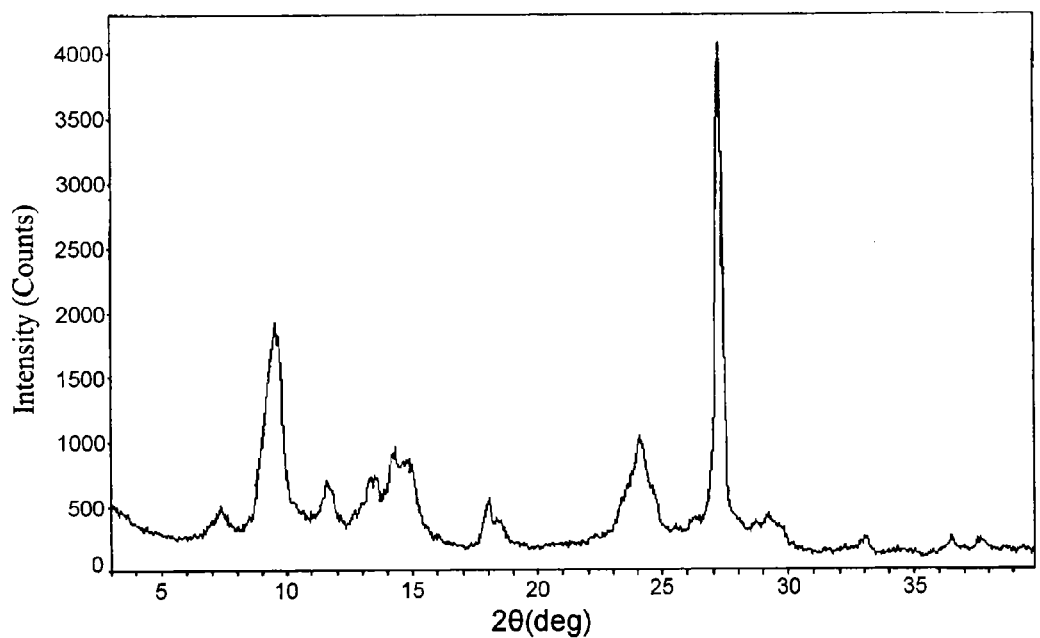
FIG. 2 is an X-ray diffraction pattern of the oxytitanium phthalocyanine used in Examples.

As a charge generation material were used oxytitanium phthalocyanine crystals. The oxytitanium phthalocyanine crystals used show main diffraction peaks at Bragg angles (2θ±0.2°) of 24.1° and 27.2° in an X-ray diffraction spectrum for a CuKα characteristic X-ray as shown in FIG. 2. The oxytitanium phthalocyanine crystals were used in an amount of 20 parts by mass and were mixed with 280 parts by mass of 1,2-dimethoxyethane. This mixture was subjected to a pulverization/dispersion treatment in which the crystals were pulverized with a sand grinding mill for 2 hours to obtain a fine dispersion.

Meanwhile, 10 parts by mass of polyvinyl butyral (trade name "Denka Butyral" #6000C, manufactured by Denki Kagaku Kogyo K.K.) was dissolved in 253 parts by mass of 1,2-dimethoxyethane and 85 parts by mass of 4-methoxy-4-methyl-2-pentanone to prepare a binder solution.

The fine dispersion obtained by the pulverization/dispersion treatment described above was mixed with the binder solution and 230 parts by mass of 1,2-dimethoxyethane to prepare a coating fluid for charge generation layer formation. This coating fluid for charge generation layer formation was applied on the undercoat layer of the electroconductive support with a bar coater so as to be a thickness of 0.4 μm after drying, and was dried to form a charge generation layer.

<Formation of Charge Transport Layer>

As a binder resin was used a polycarbonate resin (Mv=30,500) that was composed of 51% by mole of a repeating unit (unit represented by the following formula (PA)) for which 2,2-bis(4-hydroxy-3-methylphenyl)propane had been used as the aromatic diol ingredient and 49% by mole of a repeating unit (unit represented by the following formula (PB)) for which 1,1-bis(4-hydroxyphenyl)-1-phenylethane had been used as the aromatic diol ingredient, as shown below, and that had an end structure derived from p-t-butylphenol. Fifty parts by mass of the charge transport substance, 100 parts by mass of the binder resin, 8 parts by mass of the antioxidant having the structure of the following formula (AOX1), and 0.03 parts by mass of a silicone oil as a leveling agent were dissolved in 640 parts by mass of a mixed solvent of tetrahydrofuran/toluene (mass ratio: 8/2) to prepare a coating fluid for charge transport layer formation.

[Chem 25]

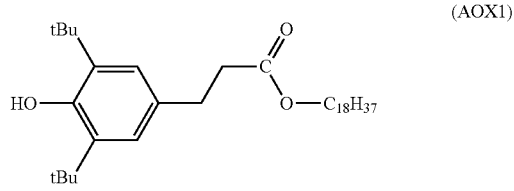
(AOX1)

[Chem 26]

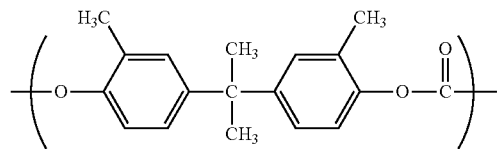
(PA)

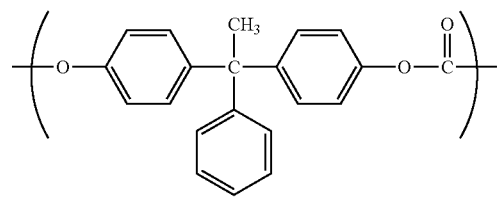
(PB)

The coating fluid for charge transport layer formation thus obtained was applied on the aforementioned charge generation layer so as to be a thickness of 25 μm after drying. Thus, an electrophotographic photoreceptor having a multilayer type photosensitive layer was obtained.

Through the steps described above, electrophotographic photoreceptors (photoreceptor numbers: photoreceptors A to I and photoreceptors RA to RO), which had a multilayer type photosensitive layer, were each produced. Details of the charge transport substance used in each electrophotographic photoreceptor are as follows.

(Photoreceptor A)

A photoreceptor A containing a charge transport substance having the compound represented by the following structural formula (CTM1), which was obtained by the above Manufacture Example 1, was produced in accordance with the above procedure and was regarded as an electrophotographic photoreceptor according to Example 1.

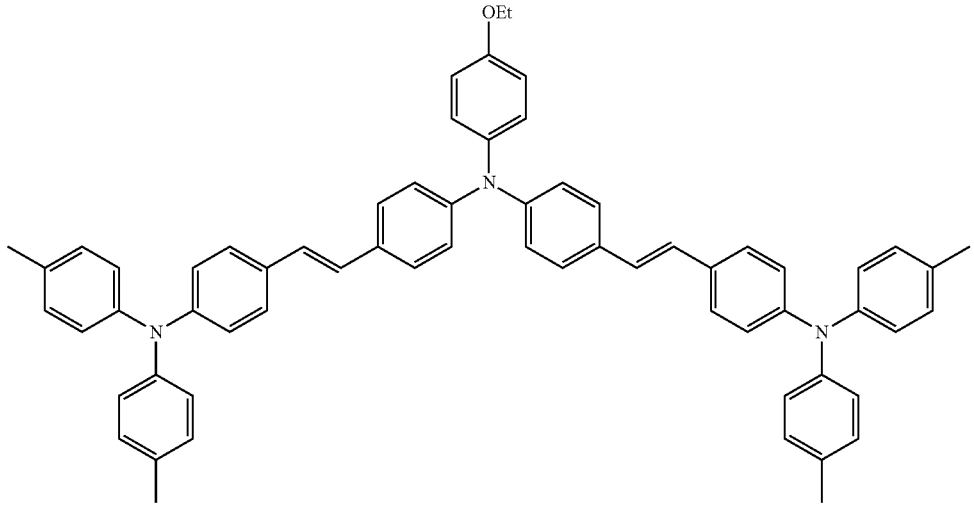
(CTM1)

(Photoreceptor B)

A photoreceptor B containing a charge transport substance having the compound represented by the following structural formula (CTM2), which was obtained by the above Manufacture Example 2, was produced in accordance with the above procedure and was regarded as an electrophotographic photoreceptor according to Example 2.

[Chem 27]

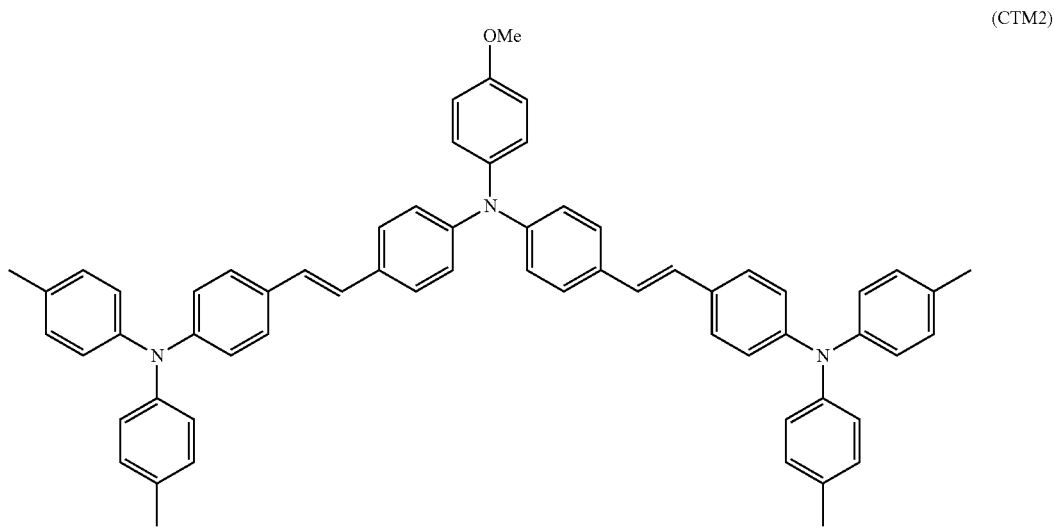

(CTM2)

(Photoreceptor C)

A photoreceptor C containing a charge transport substance having the compound represented by the following structural formula (CTM3), which was obtained by the above Manufacture Example 3, was produced in accordance with the above procedure and was regarded as an electrophotographic photoreceptor according to Example 3.

[Chem 28]

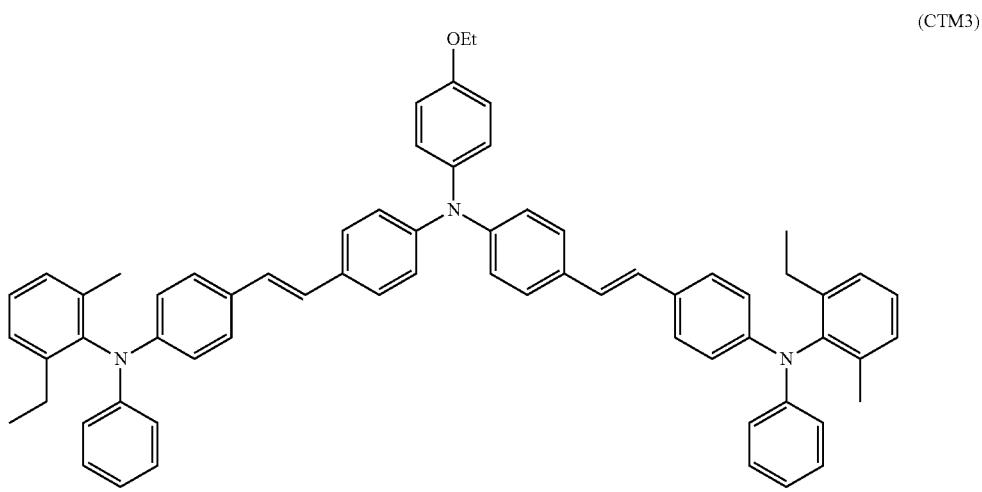

(CTM3)

(Photoreceptor RA)

A photoreceptor RA containing a charge transport substance having the compound represented by the following structural formula (RCTM1), which was used in Example 19 of JP-A-9-292724, was produced in accordance with the above procedure and was regarded as an electrophotographic photoreceptor according to Comparative Example 1.

[Chem 29]

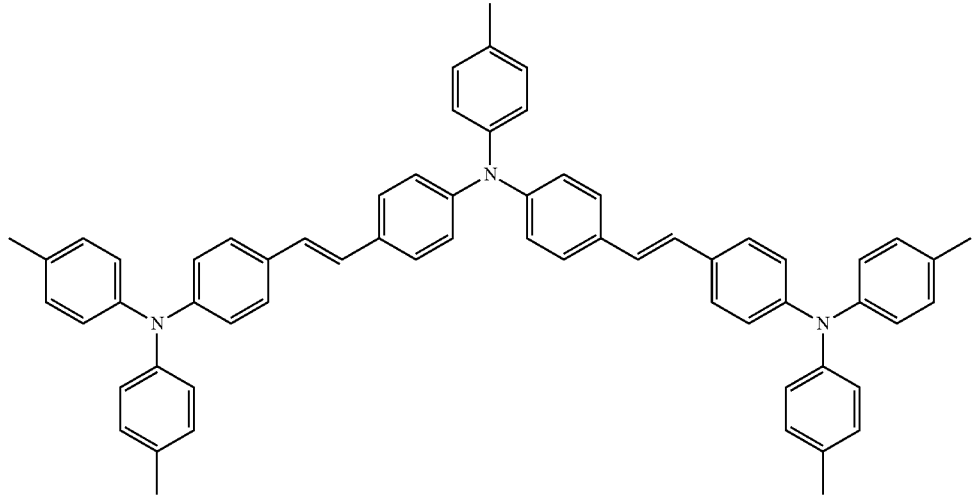

(RCTM1)

(Photoreceptor RB)

A photoreceptor RB containing a charge transport substance having the compound represented by the following structural formula (RCTM2), which was used in Example 17 of JP-A-9-292724, was produced in accordance with the above procedure and was regarded as an electrophotographic photoreceptor according to Comparative Example 2.

[Chem 30]

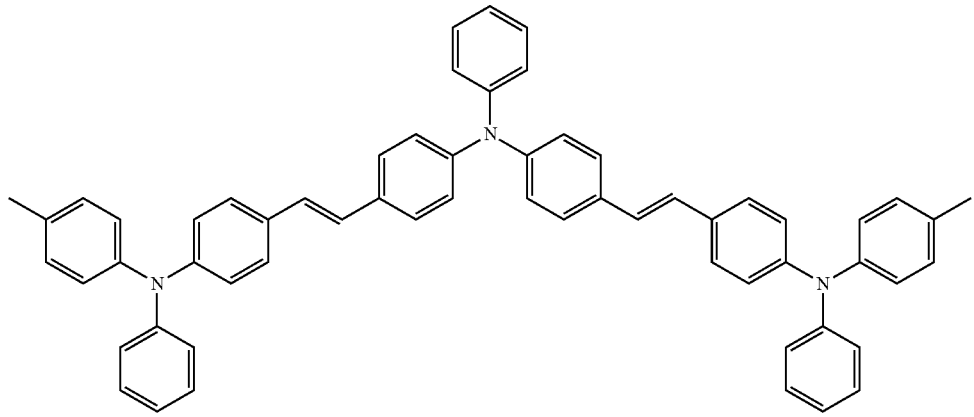

(RCTM2)

(Photoreceptor RC)

A photoreceptor RC containing a charge transport substance having the compound represented by the following structural formula (RCTM3), which was used in Example 22 of JP-A-9-292724, was produced in accordance with the above procedure and was regarded as an electrophotographic photoreceptor according to Comparative Example 3.

[Chem 31]

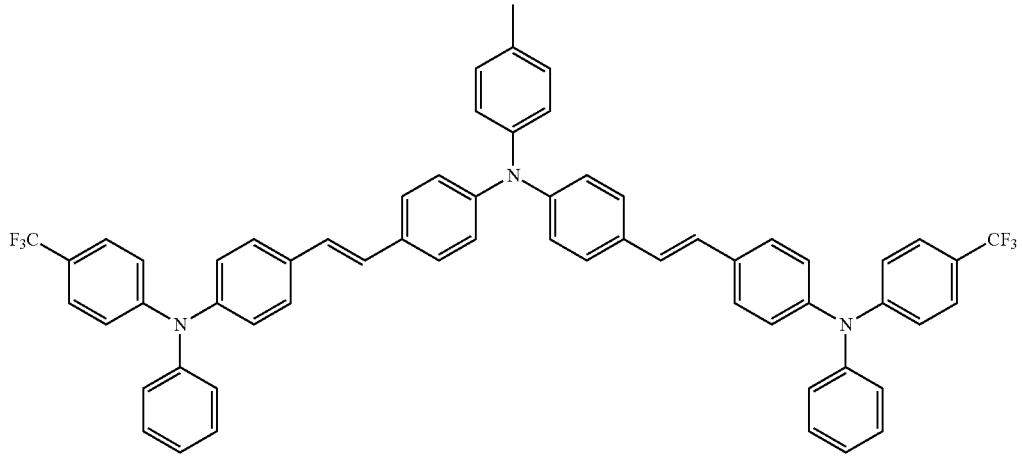

(RCTM3)

(Photoreceptor RD)

A photoreceptor RD containing a charge transport substance having the compound represented by the following structural formula (RCTM4), which was used in Manufacture Example 2 of JP-A-2008-70591, was produced in accordance with the above procedure and was regarded as an electrophotographic photoreceptor according to Comparative Example 4.

[Chem 32]

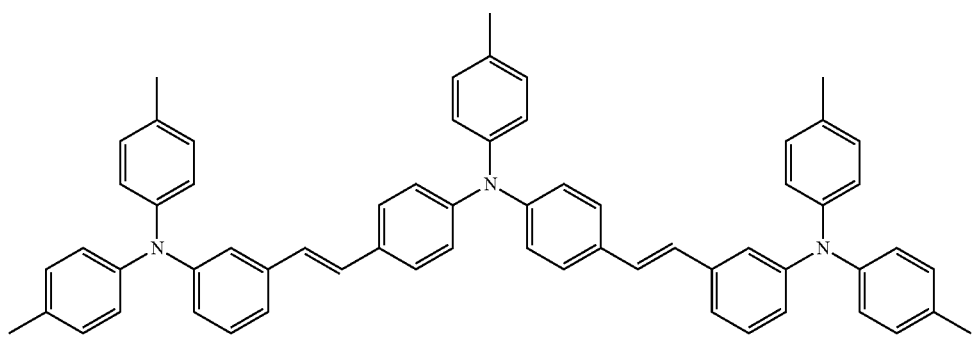

(RCTM4)

(Photoreceptor RE)

A photoreceptor RE containing a charge transport substance having the compound represented by the following structural formula (RCTM5), which was synthesized by the same operations as in Manufacture Example 1 of JP-A-2008-70591, was produced in accordance with the above procedure and was regarded as an electrophotographic photoreceptor according to Comparative Example 5.

[Chem 33]

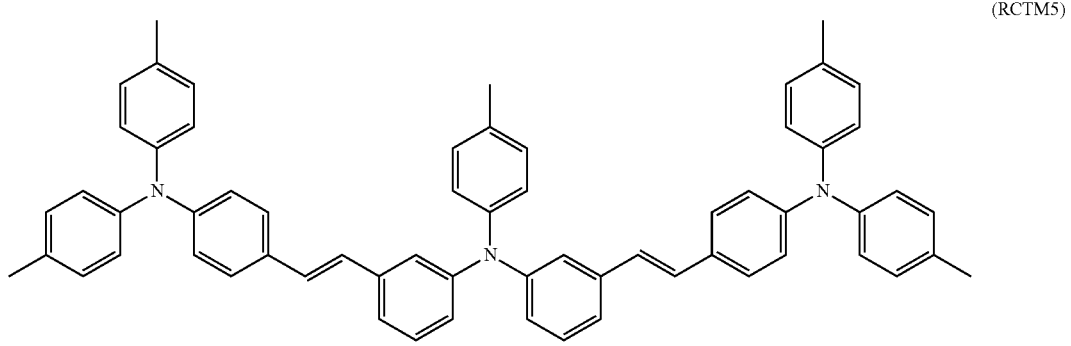

(RCTM5)

(Photoreceptor D)

A photoreceptor D was manufactured by performing the same operations as in Example 1 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Example 4.

[Chem 34]

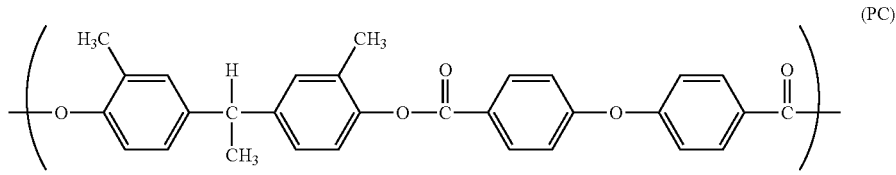

(PC)

(Photoreceptor E)

A photoreceptor E was manufactured by performing the same operations as in Example 2 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Example 5.

(Photoreceptor F)

A photoreceptor F was manufactured by performing the same operations as in Example 3 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Example 6.

(Photoreceptor RF)

A photoreceptor RF was manufactured by performing the same operations as in Comparative Example 1 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 6.

(Photoreceptor RG)

A photoreceptor RG was manufactured by performing the same operations as in Comparative Example 2 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 7.

(Photoreceptor RH)

A photoreceptor RH was manufactured by performing the same operations as in Comparative Example 3 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 8.

(Photoreceptor RI)

A photoreceptor RI was manufactured by performing the same operations as in Comparative Example 4 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 9.

(Photoreceptor RJ)

A photoreceptor RJ was manufactured by performing the same operations as in Comparative Example 5 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 10.

(Photoreceptor G)

A photoreceptor G was manufactured by performing the same operations as in Example 1 except that the binder resin of the coating fluid for charge transport layer in the above <Method for Producing Electrophotographic Photoreceptor> was changed to a polycarbonate resin (Mv=39,200) having a repeating unit represented by the following structural formula (PD), and was regarded as an electrophotographic photoreceptor according to Example 7.

[Chem 35]

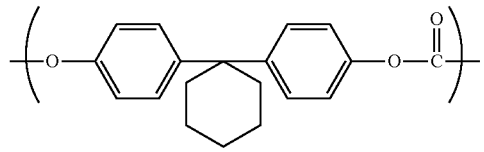

(PD)

(Photoreceptor H)

A photoreceptor H was manufactured by performing the same operations as in Example 2 except that the binder resin of the coating fluid for charge transport layer in the above <Method for Producing Electrophotographic Photoreceptor> was changed to a polycarbonate resin (Mv=39,200) having a repeating unit represented by the following structural formula (PD), and was regarded as an electrophotographic photoreceptor according to Example 8.

(Photoreceptor I)

A photoreceptor I was manufactured by performing the same operations as in Example 3 except that the binder resin of the coating fluid for charge transport layer in the above <Method for Producing Electrophotographic Photoreceptor> was changed to a polycarbonate resin (Mv=39,200) having a repeating unit represented by the following structural formula (PD), and was regarded as an electrophotographic photoreceptor according to Example 9.

(Photoreceptor RK)

A photoreceptor RK was manufactured by performing the same operations as in Comparative Example 1 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 11.

(Photoreceptor RL)

A photoreceptor RL was manufactured by performing the same operations as in Comparative Example 2 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 12.

(Photoreceptor RM)

A photoreceptor RM was manufactured by performing the same operations as in Comparative Example 3 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 13.

(Photoreceptor RN)

A photoreceptor RN was manufactured by performing the same operations as in Comparative Example 4 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 14.

(Photoreceptor RO)

A photoreceptor RO was manufactured by performing the same operations as in Comparative Example 5 except that the binder resin of the coating fluid for charge transport layer in the above <Method for Producing Electrophotographic Photoreceptor> was changed to a polyarylate resin (Mv=42,500) having a repeating unit represented by the following structural formula (PC), and was regarded as an electrophotographic photoreceptor according to Comparative Example 15.

<Evaluation of Electrophotographic Photoreceptors>

The electrophotographic photoreceptors of Examples 1 to 9 and Comparative Examples 1 to 15 were each mounted on an apparatus for evaluating electrophotographic characteristics manufactured in accordance with the standards of The Society of Electrophotography of Japan (described in Zoku Denshi Shashin Gijutsu No Kiso To Oyo (Basic and Application of Electrophotographic Technology, Part II), edited by The Society of Electrophotography of Japan, Corona Publishing Co., Ltd., pp. 404-405), and a cycle composed of charging, exposure, potential measurement, and erase was conducted in the following manner to thereby evaluate the electrical properties thereof.

Under the conditions of a temperature of 25° C. and a humidity of 50%, the photoreceptor was charged to an initial surface potential of −700 V, and was irradiated with 780-nm monochromatic light obtained by passing the light of a halogen lamp through an interference filter. The irradiation energy required for the surface potential to become −350 V (half-decay exposure energy) was measured as sensitivity (unit: μJ/cm$^2$). Furthermore, each photoreceptor was charged to an initial surface potential of −700 V and subsequently exposed to light at an irradiation energy of 0.6 μJ/cm$^2$, and the resultant surface potential (unit: −V) was measured and taken as residual potential. Moreover, each photoreceptor charged to an initial surface potential of −700 V was allowed to stand in the dark for 5 seconds, and then surface potential thereof was measured; the difference between these potential values was taken as dark decay (unit: V).

The results of the measurements are shown in Table-1 to Table-3.

TABLE 1

| | Photoreceptor | Charge transport substance | Binder | Sensitivity ($\mu$J/cm$^2$) | Residual potential (−V) | Dark decay (V) |
|---|---|---|---|---|---|---|
| Example 1 | Photoreceptor A | CTM1 | PA/PB | 0.088 | 10 | 25 |
| Example 2 | Photoreceptor B | CTM3 | PA/PB | 0.089 | 9 | 27 |
| Example 3 | Photoreceptor C | CTM4 | PA/PB | 0.089 | 10 | 27 |
| Comparative Example 1 | Photoreceptor RA | RCTM1 | PA/PB | 0.088 | 10 | 27 |
| Comparative Example 2 | Photoreceptor RB | RCTM2 | PA/PB | 0.089 | 20 | 28 |
| Comparative Example 3 | Photoreceptor RC | RCTM3 | PA/PB | 0.089 | 37 | 35 |
| Comparative Example 4 | Photoreceptor RD | RCTM4 | PA/PB | 0.089 | 58 | 32 |
| Comparative Example 5 | Photoreceptor RE | RCTM5 | PA/PB | 0.089 | 50 | 35 |

TABLE 2

| | Photoreceptor | Charge transport substance | Binder | Sensitivity ($\mu$J/cm$^2$) | Residual potential (−V) | Dark decay (V) |
|---|---|---|---|---|---|---|
| Example 4 | Photoreceptor D | CTM1 | PC | 0.096 | 16 | 28 |
| Example 5 | Photoreceptor E | CTM3 | PC | 0.098 | 15 | 30 |
| Example 6 | Photoreceptor F | CTM4 | PC | 0.098 | 17 | 30 |
| Comparative Example 6 | Photoreceptor RF | RCTM1 | PC | 0.097 | 15 | 29 |
| Comparative Example 7 | Photoreceptor RG | RCTM2 | PC | 0.100 | 43 | 31 |
| Comparative Example 8 | Photoreceptor RH | RCTM3 | PC | 0.098 | 79 | 42 |
| Comparative Example 9 | Photoreceptor RI | RCTM4 | PC | 0.106 | 110 | 38 |
| Comparative Example 10 | Photoreceptor RJ | RCTM5 | PC | 0.107 | 115 | 43 |

TABLE 3

| | Photoreceptor | Charge transport substance | Binder | Sensitivity ($\mu$J/cm$^2$) | Residual potential (−V) | Dark decay (V) |
|---|---|---|---|---|---|---|
| Example 7 | Photoreceptor G | CTM1 | PD | 0.092 | 12 | 25 |
| Example 8 | Photoreceptor H | CTM2 | PD | 0.093 | 13 | 23 |
| Example 9 | Photoreceptor I | CTM4 | PD | 0.093 | 14 | 25 |
| Comparative Example 11 | Photoreceptor RK | RCTM1 | PD | 0.097 | 12 | 24 |
| Comparative Example 12 | Photoreceptor RL | RCTM2 | PD | 0.100 | 27 | 25 |
| Comparative Example 13 | Photoreceptor RM | RCTM3 | PD | 0.098 | 46 | 31 |
| Comparative Example 14 | Photoreceptor RN | RCTM4 | PD | 0.095 | 64 | 34 |
| Comparative Example 15 | Photoreceptor RO | RCTM5 | PD | 0.096 | 57 | 32 |

From the results given in Table-1 to Table-3, in the case where the charge transport substances falling within the scope of the invention are used, high sensitivity and also low residual potential are shown as compared with the cases of the known tetrabenzidine derivatives. Moreover, as compared with the cases of the known charge transport substances having a similar structure, it is realized that it is possible to provide highly functional photoreceptors which have equal or higher sensitivity and also show low residual potential, irrespective of the binder resin used in the charge transport layer.

For further comparison of CTM1 and CTM2 with RCTM1 that are charge transport substances obviously showing the same degree of sensitivity and residual potential in the above evaluation, evaluation was carried out by the following methods.

<Abrasion Resistance>

Each of the above photoreceptor sheets was cut into a circular shape having a diameter of 10 cm and wear evaluation was performed using a Taber wear tester (manufactured by Taber Co., Ltd.). The amount of wear after rotation of 1,000 times was measured by comparing mass before and after the test under test conditions of 23° C., an atmosphere of RH 50% using the wear wheel CS-10F with no load (self weight of the wear wheel). The results of the measurement are shown in Table-4.

TABLE 4

| Photoreceptor | | Amount of wear | Number of peeled portions |
| --- | --- | --- | --- |
| Example 10 | G | 4.6 | 18 |
| Comparative Example 16 | RK | 5.1 | 54 |

From the results of Table-4, when the charge transport substance of the invention is used, it is realized that a good photoreceptor being resistant to wear and showing little peeling and good adhesiveness of the photosensitive layer is obtained.

<Solubility Test>

The charge transport substance obtained was added in a sufficient amount into 100 g of tetrahydrofuran, the solution was warmed to 60° C., and the temperature of the solution was kept at 60° C. with stirring for 1 hour. Thus, the charge transport substance was thoroughly dissolved in the solvent. Thereafter, the solution was allowed to stand in a 25° C. atmosphere for 24 hours to prepare a 25° C. saturated solution where an insoluble residue precipitated.

The solution containing the charge transport substance dissolved therein, which had been subjected to the above operations, was filtered using a filter paper for quantitative analysis of 5 class C as defined in JIS P3801 (1995). Then, 100 g of the filtrate was taken up in a container and drying was performed using a vacuum drier until the solvent is well evaporated. A remaining one after drying was weighed and the solubility (g/g) in the solvent was determined by dividing the weight of residual one after drying by 100 g that is an amount of the initially used solution. The solubility for the charge transport substance obtained is shown in Table-5 when the above measurement method was repeated three times.

TABLE 5

| | Charge transport substance | Solubility (g/g) |
| --- | --- | --- |
| Example 11 | CTM1 | 25.7 |
| Comparative Example 17 | RCTM1 | 12.2 |

From Table-5, it is realized that the solubility is very high for tetrahydrofuran most commonly used as a photosensitive layer coating solvent of the electrophotographic photoreceptor of the charge transport substance of the invention. It is considered that this high solubility is attributable to the fact that it has an oxygen atom having high polarity in the vicinity of the symmetry center of the structure.

The results of solubility is one of the indicators particularly showing the storage stability of the photosensitive layer coating fluid of the electrophotographic photoreceptor and it is suggested that possibility of crystallization decreases as the solubility increases, dispersibility becomes high, and thus high solubility is suitable for a series of the photoreceptor manufacturing process of production of electrophotographic photoreceptor coating fluid—coating fluid storage—photosensitive layer coating.

<Storage Stability Test>

As the binder resin, the polycarbonate resin (Mv=39,200) having a repeating unit represented by the structural formula (PD) was used. Then, 60 parts by mass of the charge transport substance, 100 parts by mass of the binder resin, 2 parts by mass of an antioxidant having a structure represented by the following formula (AOX2), and 0.05 parts by mass of a silicone oil as a leveling agent were dissolved in 540 parts by mass of a mixed solvent of tetrahydrofuran/toluene (mass ratio: 8/2) to prepare a charge transport layer coating fluid for coating fluid storage stability test.

The coating fluid obtained was placed in a glass sealed bottle and stored under the condition of −5 to 0° C. for 2 months. Then, it was checked whether turbidity or the like occurred or not in the coating fluid after storage, thereby evaluating the coating fluid storage stability.

The charge transport substances used in evaluation, the results of stability evaluation, and the criteria for the coating fluid stability are shown in the following Table-6.

[Chem 36]

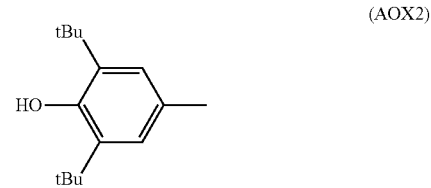

(AOX2)

TABLE 6

| | Charge transport substance | Storage stability |
| --- | --- | --- |
| Example 12 | CTM1 | Excellent |
| Comparative Example 18 | RCTM1 | Bad |

Criteria for storage stability:
Excellent: Turbidity or the like derived from crystal precipitation is not present even after storage of coating fluid
Bad: Turbidity or the like derived from precipitation of the charge transport substance is present after storage of coating fluid From Table-6, it is realized that the charge transport substance of the invention shows good compatibility with not only the coating solvent but also the binder resin used as a coating fluid and the coating fluid stability is very high. It is considered that this result is attributable to the fact that it has an oxygen atom having high polarity in the vicinity of the symmetry center of the structure. It is suggested that, as the storage stability increases, coating defects of the photosensitive layer resulting from crystal precipitation can be prevented and a homogeneous film having high dispersibility can be produced.

Example 13

By anodizing a cylinder made of an aluminum alloy having an outer diameter of 30 mm, a length of 246 mm and a wall thickness of 0.75 mm, the surface of which had been roughly cut, and subsequently carrying out a sealing treatment thereof with a sealing agent containing nickel acetate as a main ingredient, an anodized film (alumite film) of about 6 μm was formed.

Subsequently, as a charge generating material, there was used oxytitanium phthalocyanine crystals showing main diffraction peaks at Bragg angles (2θ±0.2°) of 24.1° and 27.2° in the X-ray diffraction spectrum for a CuKα characteristic X-ray, as shown in FIG. 2. Using 20 parts by mass of the oxytitanium phthalocyanine crystals, this crystals were mixed with 280 parts by mass of 1,2-dimethoxyethane and the mixture was ground for 1 hour with a sand grinding mill to perform a pulverization/dispersion treatment, thereby giving a fine dispersion. Moreover, 20 parts by mass of polyvinyl butyral (trade name "Denka Butyral" #6000C, manufactured by Denki Kagaku Kogyo K.K.) was dissolved in a mixed solution of 253 parts by mass of 1,2-dimethoxyethane and 85 parts by mass of 4-methoxy-4-methyl-2-pentanone to prepare a binder solution.

The fine dispersion obtained by the aforementioned pulverization/dispersion treatment, the aforementioned binder solution, and 230 parts by mass of 1,2-dimethoxyethane were mixed to prepare a coating fluid for charge generation layer. The cylinder was dip-coated with the coating fluid for charge generation layer to form a charge generation layer so as to be a thickness of 0.4 μm after drying.

Next, 100 parts by mass of a polyarylate resin (Mv=72,000) composed of a repeating unit represented by the above formula (PC), 40 parts by mass of a charge transport substance having a structure represented by the formula (CTM1), 4 parts by mass of an antioxidant represented by the above formula (AOX1), 0.1 part by mass of a compound represented by the following formula (AOX3), 0.5 parts by mass of a compound represented by the following formula (A1), 0.05 parts by mass of a silicone oil as a leveling agent were mixed with 1,060 parts by mass of a mixed solvent of tetrahydrofuran and toluene (tetrahydrofuran: 80% by mass, toluene: 20% by mass) to prepare a coating fluid for charge transport layer. The previously prepared cylinder having the charge generation layer formed thereon was dip-coated with the coating fluid for charge transport layer to provide a charge transport layer having a thickness of 18 μm after drying, thereby preparing a photoreceptor J.

[Chem 37]

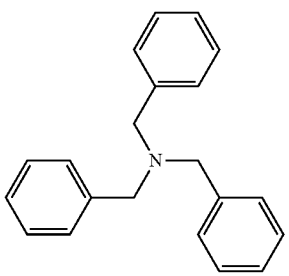

(AOX3)

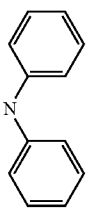

(A1)

Example 14

A photoreceptor K was manufactured by performing the same operations as in Example 13 except that the charge transport substance was changed to a compound represented by the above formula (CTM2).

Comparative Example 19

A photoreceptor RP was manufactured by performing the same operations as in Example 13 except that the charge transport substance was changed to a compound represented by the above formula (RCTM1).

<Printing Durability Evaluation Test>

Each of the electrophotographic photoreceptor obtained in Examples 13 and 14 and Comparative Example 19 was mounted on a drum cartridge for an A4 tandem full-color printer [COREFIDO C711dn manufactured by Oki Data Corporation (Printing speed: Color 34 rpm, Resolution: 600 dpi, Exposure source: LED)] and the cartridge was set in the printer. The printer was placed under conditions of low temperature and low humidity atmosphere and, as an input of print, a vertically and horizontally symmetrical pattern having a print ratio of 5% and composed of solid images and line images was sent from a personal computer to the printer to print the pattern on 12,500 sheets with a one-sheet intermittent mode.

The status of deposit on the drum surface after long-term printing was confirmed by checking the drum surface after the long-term printing using a manual non-contact image measuring instrument "TESA-VISIO 300" manufactured by TESA Co.

Figure 6:
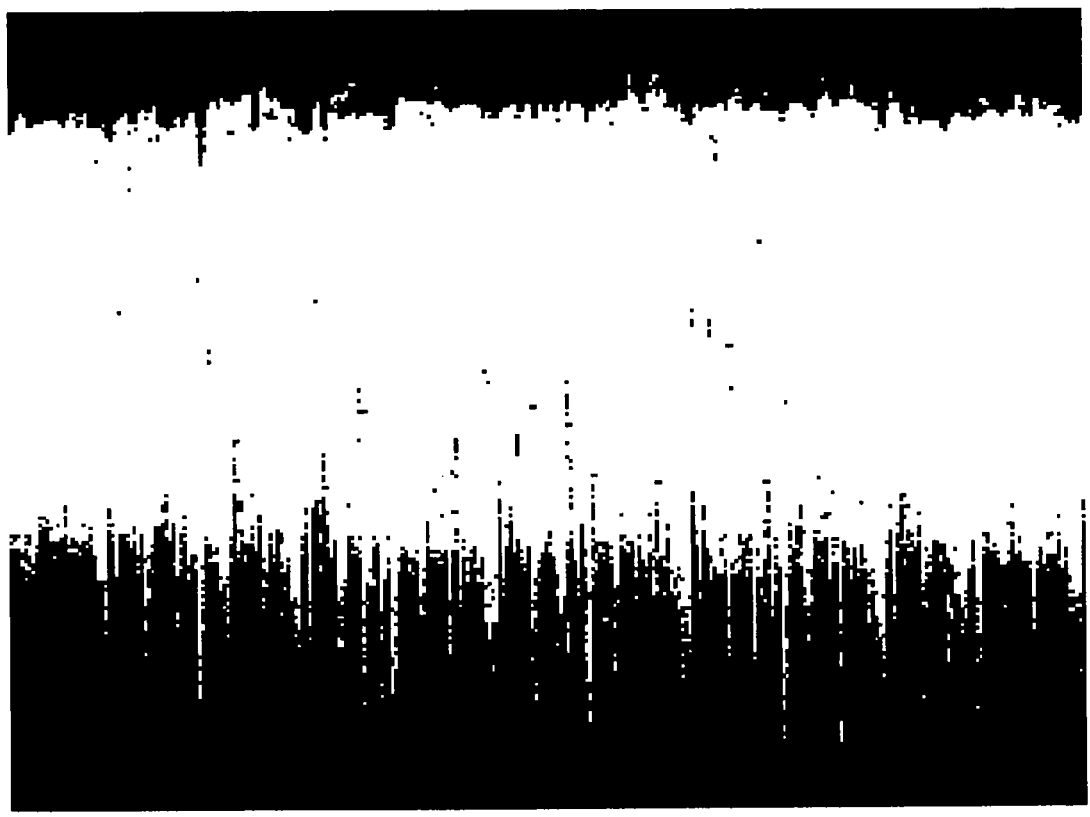
FIG. 6 is a surface photograph of a photoreceptor of Example.
Figure 7:
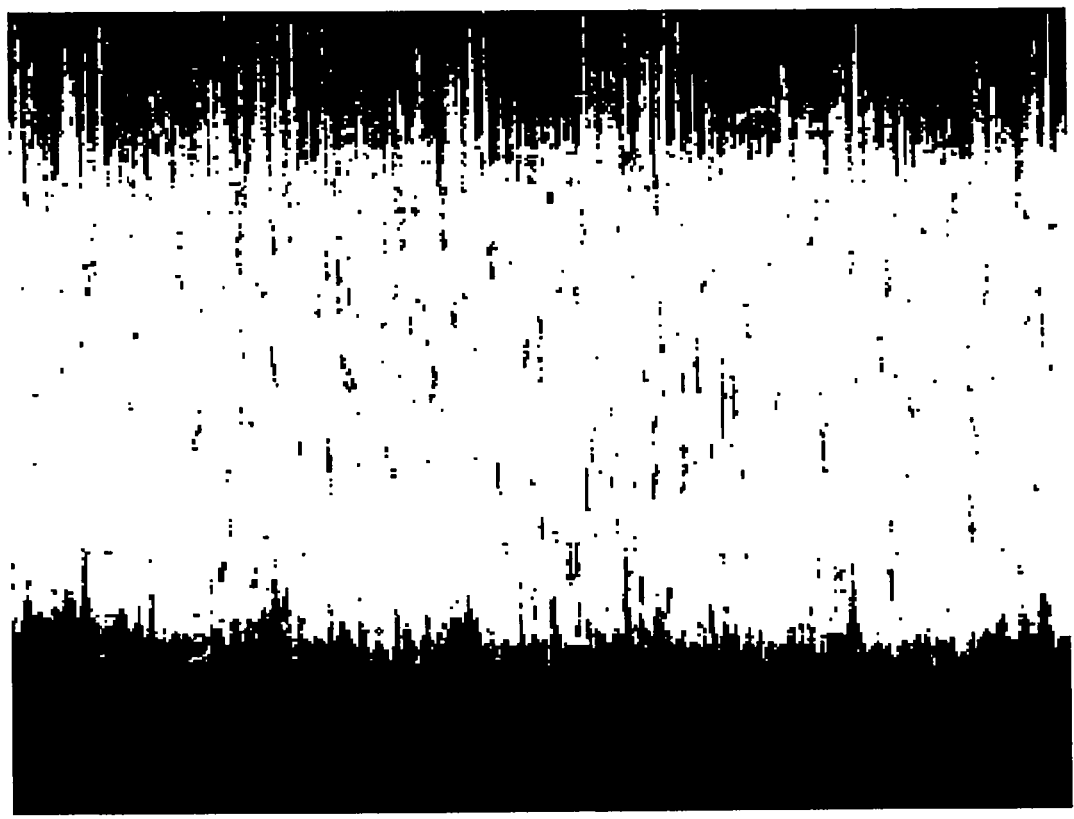
FIG. 7 is a surface photograph of a photoreceptor of Comparative Example.

The confirmation results of the deposit state of the surface of the drum after long-term printing and criteria for judging the deposit amount on the drum are shown in Table-7. Also, FIG. 6 shows a drum surface photograph after long-term printing in the photoreceptor according to Example 13 and FIG. 7 shows a drum surface photograph after long-term printing in the photoreceptor according to Comparative Example 19. They were observed by means of a monitor attached to "TESA-VISIO 300". In FIGS. 6 and 7, when black lines or dots are more frequently observed in the white portion, it can be judged that filming (deposits) more often occurs.

TABLE 7

| Photoreceptor | | Charge transport substance | Deposit amount on drum after long-term printing |
|---|---|---|---|
| Example 13 | Photoreceptor J | CTM1 | Excellent |
| Example 14 | Photoreceptor K | CTM2 | Good |
| Comparative Example 19 | Photoreceptor RP | RCTM1 | Moderate |

Criteria for deposit amount:
Excellent: a level where deposit is hardly present and no image defect is observed on a printed image after long-term printing.
Good: a level where deposits are present a little and image defects are hardly observed on a printed image after long-term printing.
Moderate: a level where deposits are present slightly much and image defects are observed slightly on a printed image after long-term printing.
Bad: a level where deposits are present much and image defects are remarkably observed on a printed image after long-term printing.

From the results shown in Table-7, in the case of using a charge transport substance falling within the scope of the invention, as compared with known charge transport substances having a similar structure, it is realized that it is possible to provide a highly functional photoreceptor which results in a small amount of deposits remaining on the photoreceptor surface even after the photoreceptor was mounted on the printer and many sheets were printed out and is highly resistant to filming while exhibiting high sensitivity and low residual potential. Also, comparing FIGS. 6 and 7, it is realized that the photoreceptor using the charge transport substance of the invention apparently results in a small amount of deposits remaining on the photoreceptor surface even after many sheets were printed out and has stronger resistance to filming.

<Evaluation of Transfer Memory>
<Manufacture of Coating Fluid for Charge Transport Layer Formation>

A polycarbonate resin (Mv=39,200) having a repeating unit represented by the above structural formula (PD) was used as a binder resin. Then, 50 parts by mass of a charge transport substance, 100 parts by mass of the binder resin, 2 parts by mass of an antioxidant having a structure of the above formula (AOX2), and 0.05 parts of a silicone oil were dissolved in 640 parts by mass of a mixed solvent of tetrahydrofuran/toluene (mass ratio: 8/2) to prepare a charge transport layer coating fluid for coating fluid storage stability test.

<Manufacture of Photoreceptor>

On a polyethylene terephthalate sheet having aluminum deposited on the surface thereof, the coating fluid for undercoat layer formation used in Example 1 was applied by means of a wire bar so as to be a thickness of about 1.3 μm after drying and dried at room temperature to provide an undercoat layer. Subsequently, on the undercoat layer, the coating fluid for charge generation layer formation used in Example 1 was applied by means of a wire bar so as to be a thickness of about 0.4 μm after drying and dried at room temperature to provide a charge generation layer. Successively, on the charge generation layer, the coating fluid for charge transport layer formation obtained as above was applied by means of an applicator so as to be a thickness of about 25 μm after drying and dried at 125° C. for 20 minutes to produce a photoreceptor L (Example 15).

Also, a photoreceptor RQ (Comparative Example 20) was produced in the same manner as in the case of the photoreceptor L except that the charge transport substance was changed to the compound represented by the above formula (RCTM1).

[Transfer Memory Test]

Using an apparatus for evaluating electrophotographic characteristics manufactured in accordance with the standards of The Society of Electrophotography of Japan (described in Zoku Denshi Shashin Gijutsu no Kiso to Oyo (Basic and Application of Electrophotographic Technology, Part II), edited by The Society of Electrophotography of Japan, Corona Publishing Co., Ltd., 1996, pp. 404-405), the above sheet-like photoreceptor was wound around an aluminum-made cylinder having a diameter of 80 mm and, after grounding it, charged so as to give an initial surface potential of about −750 V (the initial surface potential on this occasion is referred to as "V0"). After charging, the light of a halogen lamp was converted into 780-nm monochromatic light by means of an interference filter, and the surface potential (light potential; referred to as "VL") when exposed to the monochromatic light at 0.8 μJ/cm² was determined. The time from exposure to potential measurement was set to 60 ms. After the exposure to the monochromatic light, erase was performed by red LED light. The measurement was performed in an environment of 25° C. and 50% RH. The results obtained by the evaluation were regarded as results of initial electrical property test before a cycle of charging-exposure-transfer load was performed.

After performing the initial electrical property test, the erase part was removed and instead, a corotron to which +6.5 kV is applied was provided so as to simulate transfer load. In this state, the cycle of charging-exposure-transfer load was repeated 4,000 times and thereafter, VL and V0 were again measured and the differences ΔVL and ΔV0 from the initial VL and V0 were each determined. The measurement was performed in an environment of 25° C. and 50% RH. The results of the transfer memory test using the photoreceptor L and the photoreceptor RQ are shown in Table-8. In Table-8, smaller absolute values of both of ΔVL and ΔV0 indicate smaller variation of potential against transfer load and the transfer memory is better.

TABLE 8

| | Photoreceptor | Charge transport substance | ΔVL | ΔV0 |
|---|---|---|---|---|
| Example 15 | Photoreceptor L | CTM1 | 8 | −36 |
| Comparative Example 20 | Photoreceptor RQ | RCTM1 | 13 | −65 |

From the evaluation results, the electrophotographic photoreceptor of the invention shows small values of ΔVL and ΔV0 against the cycle of charging-exposure-load transfer, so that it is realized that it is possible to provide a highly functional photoreceptor which is highly resistant to transfer load and shows a good transfer memory.

Although the mechanism of exhibiting the effects of the invention is not clear, it is assumed that, by adopting such a structure as described above as the structure of the substituent possessed by the charge transport substance, the compatibility between the charge transport substance and the binder resin used in the charge transport layer is improved, and the transfer memory is good and the photoreceptor surface has high mechanical properties without impairing the performance of the sensitivity and residual potential which are basic characteristics as an electrophotographic photoreceptor.

While the invention has been described in detail and with reference to specific embodiments thereof, it will be apparent to one skilled in the art that various changes and modifications can be made therein without departing from the spirit and scope thereof.

The present application is based on Japanese Patent Application No. 2012-170115 filed on Jul. 31, 2012 and Japanese Patent Application No. 2012-215002 filed on Sep. 27, 2012, and the contents are incorporated herein by reference.

DESCRIPTION OF REFERENCE NUMERALS AND SIGNS

1 Electrophotographic photoreceptor
2 Charging device
3 Exposure device
4 Developing device
5 Transfer device
6 Cleaner
7 Fixing device
41 Developing vessel
42 Agitator
43 Feed roller
44 Developing roller
45 Control member
71 Upper fixing member (fixing roller)
72 Lower fixing member (fixing roller)
73 Heater
T Toner
P Recording paper (paper, medium)

The invention claimed is:

1. A compound represented by the formula (1):

[Chem 4]

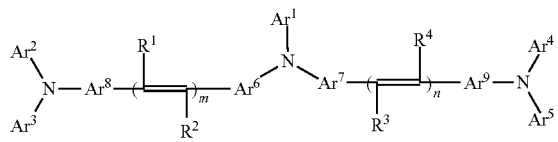

wherein $Ar^1$ represents an aryl group having an alkoxy group, an aryloxy group, or an aralkyloxy group as a substituent, $Ar^2$ to $Ar^5$ each independently represent an aryl group which may have a substituent, $Ar^6$ to $Ar^9$ each independently represent a 1,4-phenylene group which may have a substituent; $R^1$ to $R^4$ each independently represent a hydrogen atom or an alkyl group; m and n each independently represent an integer of 1 or more and 3 or less; in the case where m or n is 2 or more, plurally existing $R^1$s to $R^4$s each may be the same or different from each other.

2. The compound according to claim 1, wherein, in the above formula (1), $Ar^1$ is a phenyl group having an alkoxy group having 8 or less carbon atoms, $Ar^2$ to $Ar^5$ each independently are a phenyl group which may have an alkyl group having 1 to 6 carbon atoms or an alkoxy group having 1 to 6 carbon atoms as a substituent, $Ar^6$ to $Ar^9$ each independently are a 1,4-phenylene group which may have an alkyl group having 1 to 6 carbon atoms, $R^1$ to $R^4$ are a hydrogen atom, and m and n are both 1.

3. The compound according to claim 2, wherein, in the above formula (1), $Ar^2$ to $Ar^5$ each independently are a phenyl group which may have an alkyl group having 1 to 6 carbon atoms and $Ar^6$ to $Ar^9$ are a 1,4-phenylene group.

4. An electrophotographic photoreceptor comprising an electroconductive support and at least a photosensitive layer formed on the support, wherein the photosensitive layer contains a charge transport substance represented by the following formula (1):

[Chem 1]

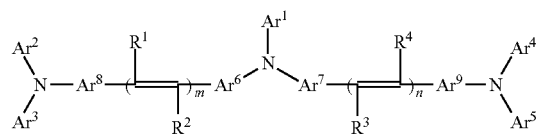

wherein $Ar^1$ represents an aryl group having an alkoxy group, an aryloxy group, or an aralkyloxy group as a substituent, $Ar^2$ to $Ar^5$ each independently represent an aryl group which may have a substituent, $Ar^6$ to $Ar^9$ each independently represent a 1,4-phenylene group which may have a substituent; $R^1$ to $R^4$ each independently represent a hydrogen atom or an alkyl group; m and n each independently represent an integer of 1 or more and 3 or less; in the case where m or n is 2 or more, plurally existing $R^1$s to $R^4$s each may be the same or different from each other.

5. The electrophotographic photoreceptor according to claim 1, wherein the photosensitive layer contains oxytitanium phthalocyanine of crystal form which shows a diffraction peak at Bragg angles (2θ±0.2°) of at least 24.1° and 27.2° in a powder X-ray diffraction spectrum with a CuKα characteristic X-ray.

6. The electrophotographic photoreceptor according to claim 1, wherein the photosensitive layer further contains at least either one of a polyarylate resin and a polycarbonate resin.

7. The electrophotographic photoreceptor according to claim 1, wherein the photosensitive layer comprises a charge transport layer and a charge generation layer and the charge transport layer contains a charge transport substance represented by the above formula (1) and at least either one of a polyarylate resin having a structural unit represented by the formula (α) and a polycarbonate resin having a structural unit represented by the formula (β):

[Chem 2]

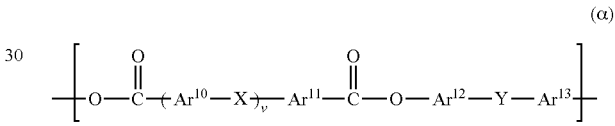

(α)

wherein $Ar^{10}$ to $Ar^{13}$ each independently represent an arylene group which may have a substituent, X represents a single bond, an oxygen atom, a sulfur atom, or an alkylene group; v represents an integer of 0 or more and 2 or less; and Y represents a single bond, an oxygen atom, a sulfur atom, or an alkylene group,

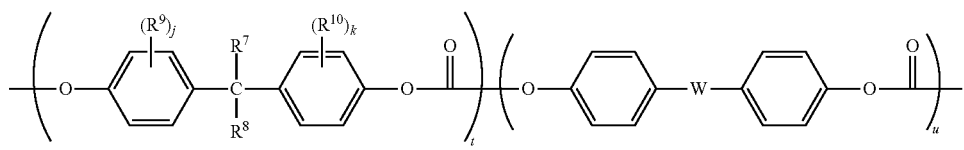

(β)

wherein $R^7$ and $R^8$ each independently represent a hydrogen atom, an aryl group, or an alkyl group having 1 to 10 carbon atoms and the $R^7$ and $R^8$ groups may be combined to form a ring; $R^9$ and $R^{10}$ each independently represent a hydrogen atom or an alkyl group having 1 to 10 carbon atoms and j and k each independently represent an integer of 0 to 4; W represents a single bond, an oxygen atom, or —$CR^{11}R^{12}$— and the $R^{11}$ and $R^{12}$ groups each independently represent a hydrogen atom, an alkyl group having 1 to 10 carbon atoms, or a phenyl group; t and u each independently represent a numeral of 0 to 100; provided that the units represented by t and u have different structures and there is no case of t=u=0.

8. An electrophotographic photoreceptor cartridge comprising: the electrophotographic photoreceptor according to claim 4; and at least one device selected from the group consisting of a charging device which charges the electrophotographic photoreceptor, an exposure device which exposes the charged electrophotographic photoreceptor to form an electrostatic latent image, and a developing device which develops the electrostatic latent image formed on the electrophotographic photoreceptor.

9. An image-forming apparatus comprising: the electrophotographic photoreceptor according to claim 1; a charging device which charges the electrophotographic photoreceptor; an exposure device which exposes the charged electrophotographic photoreceptor to form an electrostatic latent image; and a developing device which develops the electrostatic latent image formed on the electrophotographic photoreceptor.

* * * * *